United States Patent
Dezube et al.

Patent Number: 6,096,885
Date of Patent: Aug. 1, 2000

[54] OXOAZEPINE DERIVATIVES

[75] Inventors: Milana Dezube, Chapel Hill, N.C.; Gavin Charles Hirst, Marlboro, Mass.; Ronald George Sherrill, Cary, N.C.; Elizabeth Ellen Sugg, Durham, N.C.; Jerzy Ryszard Szewczyk, Chapel Hill, N.C.; Timothy Mark Willson, Durham, N.C.

[73] Assignee: Glaxo Wellcome Inc., Research Triangle Park, N.C.

[21] Appl. No.: 08/817,363

[22] PCT Filed: Oct. 12, 1995

[86] PCT No.: PCT/EP95/04026

§ 371 Date: Apr. 8, 1999

§ 102(e) Date: Apr. 8, 1999

[87] PCT Pub. No.: WO96/11940

PCT Pub. Date: Apr. 25, 1996

[30] Foreign Application Priority Data

Oct. 14, 1994 [GB] United Kingdom .................. 9420763

[51] Int. Cl.[7] .......................... C07D 223/16; A61K 31/53
[52] U.S. Cl. ........................... 540/527; 540/523; 514/213
[58] Field of Search .................................... 540/523, 527; 514/213

[56] References Cited

U.S. PATENT DOCUMENTS 5,484,917  1/1996  Lowe, III ................................. 540/523

FOREIGN PATENT DOCUMENTS

| 0 397 556 | 11/1990 | European Pat. Off. . |
| 0 487 207 | 5/1992 | European Pat. Off. . |
| 0487207 | 5/1992 | European Pat. Off. .......... C07K 5/06 |
| 9113907 | 9/1991 | WIPO .............................. C07K 5/06 |
| WOA91 13907 | 9/1991 | WIPO . |
| 9401421 | 1/1994 | WIPO .......................... C07D 267/14 |
| WOA94 01421 | 1/1994 | WIPO . |
| 9424149 | 10/1994 | WIPO .............................. C07K 5/02 |
| WOA94 24149 | 10/1994 | WIPO . |

OTHER PUBLICATIONS

Lowe et al., (CA 122:150846, Bioorg. Med. Chem. Lett. (1994), 4(24), 2877–82).
Iizuka, Hiriyuki (CA 120:231825, JP 05150415).
Lowe III et al., (J. Med. Chem., 1994, 37, 3789–3811).

Primary Examiner—Jose' G. Dees
Assistant Examiner—Sabiha N. Oazi
Attorney, Agent, or Firm—Robert H. Brink

[57] ABSTRACT

This invention relates to novel oxoazepine derivatives of Formula (I), $$R^1R^2NCOCH_2N(R^3)COR^4 \qquad (I)$$

to processes for their preparation, to pharmaceutical compositions containing them and to their use in medicine. More particularly, it relates to compounds which exhibit agonist activity for CCK-A receptors thereby enabling them to modulate the hormones gastrin and cholecystokinin (CCK) in mammals.

8 Claims, No Drawings

OXOAZEPINE DERIVATIVES

This application is filed pursuant to 35 U.S.C. § 371 as a United States National Phase Application of International Application No. PCT/EP95/04026 filed Oct. 12, 1995 which claims priority from GB 9420763.6 filed Oct. 14, 1994.

This invention relates to novel acetamide derivatives, to processes for their preparation, to pharmaceutical compositions containing them and to their use in medicine. More particularly, it relates to compounds which exhibit agonist activity for CCK-A receptors thereby enabling them to modulate the hormones gastrin and cholecystokinin (CCK) in mammals.

Cholecystokinins (CCK) and gastrin are structurally related peptides which exist in gastrointestinal tissue and in the central nervous system. Cholecystokinins include CCK-33, a neuropeptide of thirty-three amino acids in its originally isolated form, its carboxyl terminal octapeptide, CCK-8 (also a naturally occurring neuropeptide), and 39- and 12-amino acid forms. Gastrin occurs in 34-, 17- and 14-amino acid forms, with the minimum active sequence being the C-terminal tetrapeptide, Trp-Met-Asp-Phe-$NH_2$ (CCK4) which is the common structural element shared by both CCK and gastrin.

CCK and gastrin are gastrointestinal hormones and neurotransmitters in the neural and peripheral systems and perform their respective biological roles by binding to particular receptors located at various sites throughout the body. There are at least two subtypes of cholecystokinin receptors termed CCK-A and CCK-B and both are found in the periphery and in the central nervous system.

The CCK-A receptor, commonly referred to as the "peripheral-type" receptor, is primarily found in the pancreas, gallbladder, ileum, pyloric sphincter and on vagal afferent nerve fibers. Type-A CCK receptors are also found in the brain in discrete regions and serve to provide a number of CNS effects. Due to the ability of CCK-8 and Type-A CCK-selective agonists to suppress food intake in several animal species, considerable interest has been generated toward the development of new substances which function as Type-A receptor-selective CCK agonists in order to serve as anorectic agents.

The CCK-B or gastrin receptors are found in peripheral neurons, gastrointestinal smooth muscle and gastrointestinal mucosa, most notably in parietal cells, ECL cells, D cells and chief cells. CCK-B receptors also predominate in the brain and have been implicated in the regulation of anxiety, arousal and the action of neuroleptic agents.

U.S. Pat. No. 4,988,692, to Gasc, et al. describes a group of 3-acylamino 1-alkyl-5-phenyl 1,5-benzodiazepine derivatives which behave as cholecystokinin antagonists to reverse or block the effects of the endogenous hormone at its receptors.

U.S. Pat. No. 4,490,304 and PTC applications No's WO90/06937 and WO91/19733 describe peptide derivatives that exhibit CCK-A agonist activity. Such compounds have been disclosed for appetite regulation as well as the treatment and/or prevention of gastrointestinal disorders or disorders of the central nervous in animals and, more particularly, humans.

U.S. Pat. No. 5,187,154 which is incorporated herein by reference describes the use of the neuropeptide cholecystokinin (CCK) to control gastric emptying in patients having an early non-insulin-dependent diabetic condition and exhibiting rapid gastric emptying. Further the specification teaches that compounds which inhibit gastric emptying may be useful to alleviate or eliminate symptoms associated with early or pre-diabetes. Particular symptoms include elevated blood glucose and insulin levels, insulin resistance, increased susceptibility to infection or glycosuria while also maintaining gastric emptying within normal levels.

We have now discovered a novel group of acetamide derivatives compounds which exhibit a agonist activity for the CCK-A receptor thereby enabling them to modulate the hormones gastrin and cholecystokinin (CCK) in mammals. Certain of these compounds also exhibit antagonist activity at CCK-B receptors.

The present invention thus provides compounds of the general Formula (I)

and physiologically acceptable salts thereof wherein $R^1$ is independently $C_{3-6}$alkyl, $C_{3-6}$cycloalkyl, $C_{3-6}$alkenyl, phenyl, —$(CH_2)_p CN$ or —$(CH_2)_p COO$ ($C_{1-4}$alkyl) and $R^2$ is independently $C_{3-6}$alkyl, $C_{3-6}$cycloalkyl, $C_{3-6}$alkenyl, benzyl, phenyl or phenyl mono- or disubstituted independently with $C_{1-3}$alkyl, cyano, hydroxy, dimethylamino, —$O(C_{1-4}$alkyl), —$O(CH_2C_6H_5)$, —$NH(C_{1-4}$alkyl), —$COO(C_{1-4}$alkyl), —$N(C_{1-4}$alkyl)$_2$ pyrrolidino, morpholino, halogen or $C_{1-3}$alkyl substituted by one or more fluorine atoms or $R^1$ is $C_{1-2}$alkyl and $R^2$ is phenyl substituted at the 2- or 4-position with chloro, methyl, methoxy or methoxycarbonyl;

or $R^1$ and $R^2$ together with the nitrogen atom to which they are attached represent the group of formula (II)

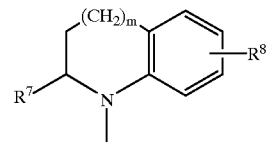

wherein $R^7$ is hydrogen or methyl, $R^8$ represents hydrogen, hydroxy, fluoro dimethylamino, $C_{1-4}$alkoxy or benzyloxy, and m is zero, 1 or 2;

$R^3$ represents a group selected from $C_{1-6}$alkyl; phenyl or phenyl substituted by one or two groups independently selected from $C_{1-3}$alkyl, $C_{1-4}$alkoxy or halogen; or thiophenyl;

$R^4$ is a group of formula (III) or (IV)

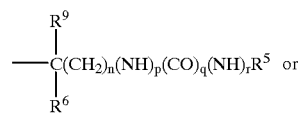

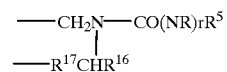

when n is zero or an integer selected from the group of 1, 2 or 3.

p is the integer 0 or 1;

q is the integer 0 or 1;

r is the integer 0 or 1, provided that when q is 0 then r is 0;

$R^9$ is selected from the group consisting of hydrogen or $C_{1-6}$alkyl;

$R^5$ is selected from the group consisting of, $C_{1-6}$alkyl, $C_{3-6}$cycloalkyl, phenyl, phenyl mono-, di or trisubstituted independently with $C_{1-4}$alkyl, hydroxy, $C_{1-6}$alkoxy, halogen, amino, mono- or di($C_{1-6}$alkyl) amino, nitro, carboxy, —COO($C_{1-4}$alkyl), carboxy$C_{1-6}$alkoxy, carboxy$C_{1-4}$alkyl, carboxymethylthio, heteroaryl, mono- or di($C_{1-6}$alkyl)aminoalkyl, or trifluoromethyl, trifluoromethoxy, $C_{1-4}$alkylthio, —SO$_v$($C_{1-4}$alkyl), —SO$_v$NH($C_{1-4}$alkyl), —SO$_v$CF$_3$ or —SO$_v$C$_6$H$_5$, —(CH$_2$)$_v$NO$_2$, —(CH$_2$)$_v$CN, —(CH$_2$)$_v$COOH, —(CH$_2$)$_v$COO($C_{1-4}$alkyl), —(CH$_2$)$_v$SCH$_3$, —(CH$_2$)$_v$ SOCH$_3$, —(CH$_2$)$_v$SO$_3$H, CH($C_{1-3}$alkyl) SO$_3$H, CH($C_{1-3}$alkyl)CO$_2$H, (CH$_2$)$_v$SO$_2$CH$_3$, —(CH$_2$)$_v$ CONH$_2$, —SCH$_2$COOH, —CONH (SO$_2$CH$_3$), —CONH(SO$_2$CF$_3$)—(CH$_2$)$_v$N(C$_{1-4}$alkyl)$_2$, —(CH$_2$)$_v$ NH(SO$_2$CF$_3$) —CH$_2$)$_v$N(SO$_2$CF$_3$) ($C_{1-4}$alkyl), —(CH$_2$)$_v$SO$_2$N(HCOC$_{1-4}$alkyl)—(CH$_2$)$_v$ SO$_2$N($C_{1-4}$alkyl), CO($C_{1-4}$alkyl), —(CH$_2$)$_v$ CONHSO$_2$($C_{1-4}$alkyl), —(CH$_2$)$_v$CON($C_{1-4}$alkyl) SO$_2$($C_{1-4}$alkyl), —(CH$_2$)$_v$NHR$^{10}$ or (CH$_2$)$_v$OR$^{11}$ substituents; heteroaryl (provided when $R^5$ is oxadiazole then $R^9$ is not hydrogen), heteroaryl substituted with halogen, $C_{1-6}$alkyl, hydroxy, nitro, cyano, carboxy, $C_{1-6}$alkoxy, benzoxy, —COO($C_{1-4}$alkyl), amino, mono- or di($C_{1-6}$alkyl)amino, phenyl or benzyl substituents; naphthyl; bicycloheteroaryl or bicycloheteroaryl N-substituted independently with hydroxy, carboxyalkyl, phenyl, heteroaryl, $C_{1-4}$alkoxy or cyano substituents, further provided when n is 1, p is 0, q is 0 and r is 0 then heteroaryl, substituted heteroaryl, bicycloheteroaryl and substituted bicycloheteroaryl are bound at the 3 position, still further provided that when n is 0, p is 1, q is 1 and r is 0 then heteraryl, substituted heteroaryl, bicycloheteroaryl and substituted bicycloheteroaryl are bound at the 2 position;

$R^{10}$ is hydrogen acetyl, $C_{1-4}$alkyl, SO$_3$H, —SO$_2$CH$_3$, —SO$_2$CF$_3$, —SO$_2$C$_6$H$_5$, $C_{1-4}$alkoxycarbonyl $R^{11}$ is hydrogen, $C_{1-6}$alkyl, $C_{3-6}$cycloalkyl, —CH$_2$C$_6$H$_5$, —CH$_2$COOH, —CH$_2$CONH$_2$, —CH$_2$CONH($C_{1-4}$alkyl), —CH$_2$CON($C_{1-4}$alkyl)$_2$ or

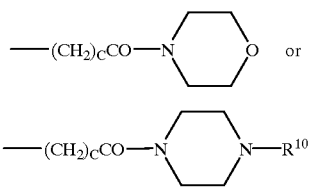

v is a integer selected from the group 0, 1 or 2;
c is zero or 1
$R^6$ represents a group selected from hydrogen, $C_{1-3}$alkyl optionally substituted by a group selected from hydroxy, carboxy, $C_{1-4}$alkoxycarbonyl, aminocarbonyl, hydroxyphenyl, phenyl, methoxy, thiomethyl or benzyloxyphenyl;
or $R^3$ and $R^6$ together form a linking chain selected from

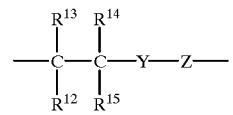

wherein the group Z is linked to the rest of the molecule at the carbon atom substituted by the group $R^9$ and
wherein Z is a group selected from, CH$_2$, C(CH$_3$)$_2$, =C(CH$_3$) or CO, Y is a group selected from NR$^{20}$, N=, S, SO, SO$_2$, CO or CH$_2$, R$^{12}$, R$^{13}$, R$^{14}$ and R$^{15}$ each represent hydrogen, or R$^{13}$ and R$^{14}$ together form a double bond and R$^{12}$ and R$^{15}$ are both hydrogen or the groups R$^{12}$, R$^{13}$, R$^{14}$ and R$^{15}$ and the two carbon atoms to which they are attached form a phenyl ring which may optionally carry additional substituents selected from halogen, trifluoromethyl, $C_{1-3}$alkyl, $C_{1-4}$alkylthio, or $C_{1-4}$alkoxy, with the proviso that when n is an integer selected from 1, 2 or 3 then Y is NR$^{20}$ and Z is CO or YZ represents the group —N=C(CH$_3$)—;

R$^{16}$ and R$^{20}$ independently represents a group selected from $C_{1-6}$alkyl, $C_{3-8}$cyclolaky, phenyl (optionally substituted by halogen), pyridyl, pyrimidinyl or thiophenyl.

R$^{17}$ together with R$^3$ form an ortho disubstituted phenyl ring which may be optionally substituted by halogen, trifluoromethyl, $C_{1-3}$alkyl, $C_{1-4}$alkylthio or $C_{1-4}$alkoxy.

The term heteroaryl preferably refers to a 5, or 6 membered aromatic ring which contains, 1, 2, 3 or 4 heteroatoms selected from N, S or O with the proviso that any two O or S atoms are not bonded together. The term bicycloheteroaryl preferably refers to a 5, or 6 ring membered heteroaryl group fused to a phenyl ring and which phenyl ring may also be substituted.

When n is zero p is 1, q is 1 and r is zero, the group $R^5$ is conveniently
(1) a heterocycle linked at its 2- position and selected from pyrrole, tetrahydropyrrole, indole, benzofuran, thiophene, benzothiophene, indoline, quinoline or 4-oxobenzopyran and wherein said pyrrole, tetrahydropyrrole, indole or indoline may optionally be substituted on the ring nitrogen thereof by the group R$^{18}$ as defined hereunder and said indole, indoline, quinoline, benzofuran, benzothiophene or 4-oxobenzopyran may optionally be substituted in the benzo ring thereof by the group R$^{19}$ as defined hereunder or
(2) phenyl or phenyl mono- or disubstituted independently with halogen, hydroxy, cyano, carboxy, —O(C$_{1-4}$alkyl), —O(CH$_2$C$_6$H$_5$), —COO(C$_{1-4}$alkyl), amino, dimethylamino, —NHR$^{10}$, 1-pyrrolidinyl or tetrazolyl; or
(3) pyridine or pyridinyl mono- or disubstituted independently with halogen, methyl, hydroxy, nitro, cyano, carboxy, —O(C$_{1-4}$ alkyl), —O(CH$_2$C$_6$H$_5$), —COO (C$_{1-4}$ alkyl), amino or dimethylamino;
R$^{18}$ is —(CH$_2$)$_b$COOH, wherein b is 0, 1, 2 or 3
R$^{19}$ is methyl, chloro, nitro, hydroxy, methoxy or —NHR$^{10}$;
When n is zero and p, q and r represent 1, $R^5$ conveniently is phenyl or phenyl mono- or disubstituted independently with fluorine, trifluoromethoxy, $C_{1-4}$alkylthio, $-(CH_2)_v COOH$, $-(CH_2)_v COO(C_{1-4}$ alkyl), $-(CH_2)_v SCH_3$, $-(CH_2)_v SO_3H$, $(CH_2)_v SOCH_3$, $-(CH_2)_v SO_2CH_3$, $-(CH_2)_v CONH_2$, $-SCH_2COOH$, $-CONH(SO_2CH_3)$, $-CONH(SO_2CF_3)$, $-(CH_2)_v N(C_{1-4}alkyl)_2$, $-(CH_2)_v NH(SO_2CF_3)$, $-(CH_2)_v N(SO_2CF_3)(C_{1-4}alkyl)$, $-(CH_2)_v SO_2NHCO(C_{1-4}alkyl)$, $-(CH_2)_v SO_2N(C_{1-4}alkyl)CO(C_{1-4}alkyl)$, $-(CH_2)_v CONHSO_2(C_{1-4}alkyl)$, $-(CH_2)_v CON(C_{1-4}alkyl)SO_2(C_{1-4}alkyl)$, $-(CH_2)_v OR^{11}$ $-(CH_2)_v NHR^{10}$, or phenyl mono-substituted with $-(CH_2)v(tetrazolyl)$, $-(CH_2)_v(carboxamidotetrazolyl)$ or $-(CH_2)_v(pyrrolidinyl)$ or $R^5$ is selected from pyridine or pyridinyl mono- or disubstituted independently with halogen, methyl, hydroxy, nitro, cyano, carboxy, $-O(C_{1-4}$ alkyl), amino, dimethylamino, $-NHR^{10}$; or $R^5$ is a 7-indazolyl group carrying a group $R^{10}$ at the N−1 position.

A preferred class of compounds of the invention include those wherein n is zero, p is 1 q is 1 and r is zero or 1.

A further preferred class of compounds are those wherein n is 1 and p, q and r are zero.

When n is 1 and p, q and r are zero, $R^5$ is conveniently a heteroaryl or bicycloheteroaryl linked at the 3-position in the heteroaryl ring. Examples of suitable heteroaryl rings include furan, thiophene or pyrrole which groups may be substituted by 1 or 2 alkyl group. Examples of suitable bicyclic heteroaral rings include benzofuran, benzothiophene, indole or indazole. Preferably the group $R^5$ is 3-indazolyl.

Compounds of formula (I) wherein $R^1$ represents $C_{3-6}$alkyl e.g. isopropyl, and $R^2$ represents phenyl optionally substituted in the para position e.g. by hydroxy or methoxy, or trifluoromethyl represent a further preferred class of compounds of the invention.

A preferred group of compounds of formula (I) include those where $R^1$ represents $C_{3-6}$alkyl e.g. isopropyl, $R^2$ represents phenyl optionally substituted in the para position by methoxy or hydroxy, $R^3$ represents $C_{1-6}$alkyl or phenyl optionally substituted by halogen e.g. chlorine, $R^6$ represents hydrogen, or alkyl substituted by hydroxy e.g. hydroxymethyl, alkyl e.g. methyl (substituted by phenyl, hydroxyphenyl or benzyloxphenyl), alkyl e.g. ethyl (substituted by carboxy or alkoxycarbonyl e.g. methoxycarbonyl), $R^9$ represents hydrogen, n is zero, p is 1, q is 1 and r is zero or 1 and $R^5$ represents optionally substituted phenyl e.g. phenyl, 3-rboxyphenyl or 3-methylthiophenyl or n is zero, p is 1, q is 1, r is zero and $R^5$ is 2-indolyl.

A further preferred class of compounds of formula (I) are those wherein $R^1$ is $C_{3-6}$alkyl e.g. isopropyl, $R^2$ is phenyl optionally substituted in the 4 position by methoxy, X is $NR^{20}$ (wherein $R^{20}$ is phenyl) or $CH_2$, Y is CO or $CH_2$ and $R^{12}$, $R^{13}$, $R^{14}$ and $R^{15}$ each represent hydrogen or $R^{13}$ and $R^{14}$ together form a double bond and $R^{12}$ and $R^{15}$ are hydrogen, n is zero, p is 1, q is 1, r is 1 and $R^5$ is optionally substituted phenyl e.g. phenyl or phenyl substituted by carboxy, or n is zero, p is 1, q is 1, r is zero and $R^5$ is 2-indolyl optionally substituted at the 1-position by the group $(CH_2)bCO_2H$ wherein b is 1, 2 or 3 or n is 1, p,q and r are zero and $R^5$ is 3-indazolyl.

Yet a further preferred class of compounds of formula (I) are those wherein $R^1$ is $C_{3-6}$alkyl e.g. isopropyl, $R^2$ is phenyl or 4-methoxyphenyl, n is zero, p is 1, q is 1, r is 1 and $R^5$ is phenyl optionally substituted by carboxy or fluoro, or n is zero, p and q are 1, r is zero and $R^5$ is 2-indolyl optionally substituted at the 1-position by the group $CH_2CO_2H$, X is S, SO or $SO_2$, $CH_2$ or CO and Y is $CH_2$ or $C(CH_3)_2$ or X Y is the group $-N=C(CH_3)-$.

Those skilled in the art will recognize that stereocenters exist in compounds of Formula (I). Accordingly, the present invention includes all possible stereoisomers and geometric isomers of Formula (I) and includes not only racemic compounds but also the optically active isomers as well. When a compound of Formula (I) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Additionally, in situations where tautomers of the compounds of Formula (I) are possible, the present invention is intended to include all tautomeric forms of the compounds.

It will also be appreciated by those skilled in the art that the compounds of the present invention may also be utilized in the form of a pharmaceutically acceptable salt or solvate thereof. The physiologically acceptable salts of the compounds of Formula (I) include conventional salts formed from pharmaceutically acceptable inorganic or organic acids as well as quaternary ammonium acid addition salts. More specific examples of suitable salts include hydrochloric, hydrobromic, sulphuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulphonic, methanesulphonic, naphthalene-2-sulphonic, benzenesulphonic and the like. Other acids such as oxalic, while not in themselves pharmaceutically acceptable, may be useful in the preparation of salts useful as intermediates in obtaining the compounds of the invention and their pharmaceutically acceptable salts. References hereinafter to a compound according to the invention include both compounds of Formula (I) and their pharmaceutically acceptable salts and solvates.

The compounds of the present invention exhibit CCK-A agonist activity and can be considered full or partial cholecystokinin agonists in that they bind to CCK-A receptors and either fully or partially stimulate gallbladder contraction and/or reduce feeding in animal paradigms. They also inhibit gastric emptying.

As agonists of CCK-A receptors, the compounds of the present invention are useful anorectic agents advantageous in the treatment of obesity as well as related pathologies, such as diabetes or hypertension. Moreover, the compounds disclosed herein provide for new approaches for inducing satiety, providing for appetite regulation and modifying food intake in mammals, especially humans, to regulate appetite, treat obesity and maintain weight loss. The compounds are also useful for the treatment of non-insulin dependent diabetic conditions associated with rapid gastric emptying.

Additionally, certain compounds of the present invention may also exhibit some antagonist activity at particular site-specific CCK-B and gastrin receptors as demonstrated by their inhibition of CCK-4 stimulated contraction of isolated guinea-pig ileum longitudinal muscle-myenteric plexus and pentagastrin-stimulated acid secretion in rat isolated gastric mucosa using the procedures described by M. Patel and C. F. Spraggs in Br. J. Pharmac., (1992), 106, 275–282 and by J. J. Reeves and R. Stables in Br. J. Pharmac., (1985), 86, 677–684.

The relative affinities of compounds of the invention for the CCK-A and CCK-B receptors may be determined using known conventional procedures such as described by Fomos et al J. Pharmacol Exp. Ther., 1992 261, 1056–1063.

The ability of compounds of the invention to inhibit gastric acid secretion, such as pentagastrin stimulated acid secretion may be determined in the conscious gastric fistula rat using methods described by Hedges and Parsons Journal of Physiology 1977, 267191–194.

The compounds of formula (I) inhibit or delay gastric emptying and this may be determined using standard tests. Thus for example rats deprived for food for 18 hr may be pretreated with the test compound administered i.p at a pre-set time (20 mins) before being given a methyl cellulose meal which is administered by the gavage route. The meal contains a marker element such as Phenol Red. After specific predetermined time intervals the rats are sacrificed and the amount of the meal in the stomach is determined by measuring the concentration of the marker substance present. This value is then compared with a control animal which was not pre-treated with the test compound.

The ability of compounds of the invention to inhibit gastric emptying may be determined using conventional procedures.

In a further aspect the invention provides a compound of Formula (I) or a pharmaceutically acceptable salt or solvate thereof for use in therapy, and in particular, in human medicine.

According to another aspect, the present invention provides the use of a compound of Formula (I) or a pharmaceutically acceptable salt or solvate thereof for the manufacture of a medicament for the treatment of conditions where modification of the effects of CCK and/or gastrin is of therapeutic benefit.

According to a further aspect of the present invention, there is provided herein a method for the treatment of a mammal, including man, in particular in the treatment conditions where modification of the effects of CCK and/or gastrin is of therapeutic benefit, the method comprising administering to the patient an therapeutically effective amount of a compound of Formula (I) or a pharmaceutically acceptable salt or solvate thereof.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, e.g., 1–1500 mg per day. The desired dose may conveniently be presented in a single dose or as divided doses administered at appropriate intervals, for example as two, three, four or more sub-doses per day.

While it is possible that compounds of the present invention may be therapeutically administered as the raw chemical, it is preferable to present the active ingredient as a pharmaceutical formulation. Accordingly, the present invention further provides for a pharmaceutical formulation comprising a compound of Formula (I) or a pharmaceutically acceptable salt thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Formulations of the present invention include those especially formulated for oral, buccal, parenteral, implant, or rectal administration, however, oral administration is preferred. For buccal administration, the composition may take the form of tablets or lozenges formulated in conventional manner. Tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulphate. The tablets may be coated according to methods well-known in the art. Suitable tablet coatings include conventional enteric coatings.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

For oral administration the compounds of the invention are conveniently administered as enteric coated tablets or capsules made from enteric materials or coated with an enteric film.

Additionally, compositions the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile, pyrogen-free water) before use.

The composition according to the invention may also be formulated as a depot preparation. Such long acting formulations may be administered by implantation (for example, subcutaneously or intramuscularly) or by intramuscular injection. Accordingly, the compounds of the invention may be formulated with suitable polymeric or hydrophobic materials (as an emulsion in an acceptable oil, for example), ion exchange resins or as sparingly soluble derivatives as a sparingly soluble salt, for example.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description the groups $R^1$, $R^2$, $R^3$ and $R^4$ are as defined for the compounds of formula (I) unless otherwise defined.

According to a first general process A compounds of formula (I) wherein $R^4$ is the group of formula (III), p is 1 and q is 1, or the group of formula (IV) may be prepared by reaction of an amine of formula (V) wherein $R^1$, $R^2$, $R^3$, $R^6$ and $R^9$ have the meaning defined in formula (I) or are groups convertible thereto, or the amine (VI) wherein $R^1$, $R^2$, $R^3$, $R^{16}$ and $R^{17}$ have the meanings defined in formula (I) or are groups convertible thereto.

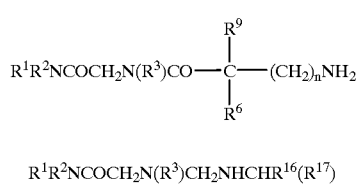

(V)

$R^1R^2NCOCH_2N(R^3)CH_2NHCHR^{16}(R^{17})$ (VI)

with an acylating agent capable of introducing the group $CO(NH)_rR^5$.

Thus in one embodiment of this process compounds of formula (I) wherein r is 1 may be prepared by reaction with a compound $R^5$W (VII) wherein W is the group —NCO, HNCOCl or $NHCOR_a$ where $R_a$ is nitro substituted phenoxy group or a 1-imidazole group.

The reaction conveniently takes place in the presence of a suitable solvent such as a halohydrocarbon (e.g. dichloromethane), an ether (e.g. tetrahydrofuran) or nitrile (e.g. acetonitrile) or a mixture thereof at a temperature in the range of 0°–80° C.

Compounds of formula (VII) wherein W is —NCO may be purchased or prepared by the reaction of an amine $H_2N—R^5$ with phosgene or triphosgene in a suitable solvent such as methylene chloride. Compounds of formula (VII) wherein W is NHCOCl are also prepared by the reaction of amines $H_2NR^5$ with phosgene or triphosgene in a suitable solvent such as methylene chloride. Compounds of formula (VII) wherein W is $NHCOR_a$ and $R_a$ is a 1-imidazole group are prepared by treatment of amines $H_2N—R^5$ with carbonyl diimidazole in a suitable solvent (dichloromethane, ether, tetrahydrofuran) at a temperature ranging from 0–80° C. (conveniently at room temperature). Compounds of formula (VII) wherein W is $HNCOR_a$ and $R_a$ is a nitro substituted phenoxy group are prepared by the reaction of amines $H_2N—R^5$ with the appropriate chloroformate $R_aCOCl$ in the presence of a base (pyridine, triethylamine) in a suitable solvent (dichloromethane) and at a temperature of 0–50° C.

In a second embodiment of this process compounds of formula (I) wherein r is zero may be prepared by reaction of the amine (V) or (VI) with the carboxylic acid $R^5CO_2H$ (VIII)

Thus reaction of the intermediates of formulae (V) or (VI) with the acid of formula (VIII) may be carried out in the presence of a suitable dehydrating agent such as dicyclohexylcarbodiimide (DCC), 1-(3-dimethylaminopropyl)-3-ethylcarbodiimide hydrochloride (EDC) or bis(2-oxo-3-oxazolidinyl)phosphinic chloride (BOP), or hydroxybenzotriazole (HOBT)

Alternatively, compounds of general Formula (I) may be obtained by reaction of the intermediates of Formula (V) or (VI) with an activated derivative of the acid (VIII) such as an acid chloride or anhydride thereof, including mixed anhydrides.

Suitable solvents for this process embodiment include N,N-dimethylformamide or dichloromethane. And the reaction is Preferably carried out at temperatures between 0–60° C. Conveniently the reaction is carried out in the presence of a base such as triethylamine or N,N-dimethylaminopyridene (DAMP).

According to a further general process B, compounds of formula (I) wherein r is 1 may be prepared by reaction of an intermediate of formula (IX) or (X).

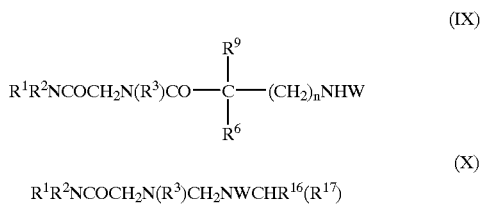

$R^1R^2NCOCH_2N(R^3)CH_2NWCHR^{16}(R^{17})$ (X)

wherein W is the group —NCO, —NHCOCl or $NHCOR_a$ wherein $R_a$ is a nitro substituted phenoxy group or a 1-imidazole group with an amine (XI)

$NH_2R^5$ (XI)

and optionally in the presence of a base such as a tertiary amine (e.g. triethylamine).

The reaction conveniently takes place in a suitable solvent such as a halogenated hydrocarbon (e.g. dichloromethane) or an ether (e.g. tetrahydrofuran) or an amide (e.g. N,N-dimethyl formamide) optionally at a temperature ranging from room temperature to the reflux temperature of the solvent.

Conveniently the compounds of formula (IX) or (X) are prepared in situ from the corresponding amines of formula (V) or (VI).

In a particular aspect of the process (B) when W is the group $NHCOR_a$ and $R_a$ is a 1-imidazole group, the imidazolide (IX) or (X) may be formed in situ in which case the amine of formula (XI) may be mixed with the compounds of formula (V) or (VI) in the presence of carbonyldiimidazole under the aforementioned conditions.

For process B when W is the group $NHCOR_a$ and $R_a$ is a nitro substituted phenoxy group the reaction with the primary amine (XI) is preferably carried out in the presence of a base such as a tertiary amine e.g. triethylamine.

For process B when W is the isocyanate group —N=C=O the reaction with the primary amine (XII) is preferably carried out in an aprotic solvent such as a halohydrocarbon e.g. methylene chloride. Conveniently the isocyanate is generated in situ prior to the addition of the primary amine (XI).

The compounds of formula (IX) or (X) wherein $R_a$ is an optionally substituted phenoxy group may be prepared from the primary amine (V) or (VI) by reaction with the corresponding nitro substituted phenyl chloroformate in the presence of a base such as pyridine. The reaction may be carried out in a solvent such as a halohydrocabon e.g. dichloromethane and at a temperature from 0–50°.

Compounds of formula (IX) or (X) wherein $R_a$ is a 1-imidazole group may be prepared by reacting a compound of formula (V) or (VI) with carbonyldiimidazole in the presence of a suitable solvent such as a halogenated hydrocarbon (e.g. dichloromethane) or an ether (e.g. tetrahydrofuran) at a temperature ranging from 0° to 80° (conveniently at room temperature).

Compounds of formula (IX) or (X) wherein W is the isocyanate grouping —N=C=O or carbamoyl chloride —NHCOCl may be prepared from the primary amine (V) or (VI) by reaction with phosgene ($COCl_2$) or triphosgene in a suitable solvent such as methylene chloride.

According to a further general process C compounds of formula (I) wherein $R^3$ and $R^6$ or $R^3$ and $R^{17}$ together form part of a cyclic structure may also be prepared by a reaction of the compound of formula

$$HN(R^3)COR^4 \qquad (XII)$$

with an acetylbromide or chloride having the formula (XIII)

$$R^1R^2NCOCH_2hal \qquad (XIII)$$

wherein hal=Cl or Br.

The reaction is conveniently carried out by treating the compound of formula (XII) with a strong base such as sodium hydride in a polar aprotic solvent such as N,N-dimethylformamide followed by reaction with the acetyl halide (XIII).

The acetyl halide (XIII) is prepared by the reaction of the amine $R^1R^2NH$ with corresponding haloacetyl bromide in dichloromethane at 0° C., with a suitable base, such as triethylamine.

The amines $R^1R^2NH$, may be prepared by the reductive alkylation of the amine $H_2N-R^2$ with an appropriate aldehyde or ketone.

According to a general process D compounds of formula (I) wherein $R^4$ is a group of formula (III) and n is 1, 2 or 3 and p and r are zero may be prepared by reaction of the compound (XIV) wherein $R^1$, $R^2$, $R^3$, $R^6$ and $R^9$ have the meanings defined in formula (I) or are groups convertible thereto.

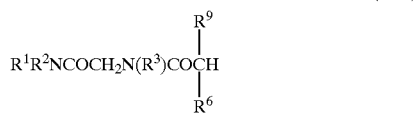
(XIV)

with an halide (XV) wherein $R^5$ has the meanings defined in formula (I) q is zero or 1 n is 1, 2 or 3 and hal is Br Cl or I.

$$R^5(CO)_q(CH_2)_nhal \qquad (XV)$$

The reaction is carried out in the presence of a base such as an alkali metal alkoxide, alkali metal hydride, alkyl lithium or alkali disilylazide. The reaction is preferably carried in a solvent such as tetrahydrofuran, dichloromethane or N,N-dimethylamamide and conveniently at a temperature within the range −80° to 25° C.

According to a general process E compounds of formula (I) wherein $R^4$ is a group of formula (III) and p is zero, q is 1 and r is I may be prepared by reaction of the compound of formula (XVI) wherein $R^1$, $R^2$, $R^3$, $R^6$ and $R^9$ have the meanings defined above or are groups convertible thereto.

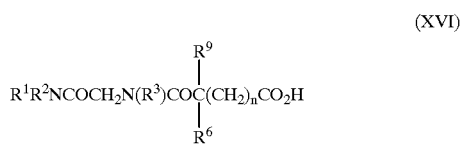
(XVI)

with the amine $R^5NH_2$ (XI) in the presence of a suitable dehydrating agent such as DCC,EDC, BOP or bromo-tris-pyrrolidino phosphonium hexfluorophosphate Py Brop) is a solvent such as N, N-dimethylformamide or dichloromethene.

Conveniently the reaction is carried out in the presence of a tertiary organic base such as triethylamine N-methylmorpholino or N,N-dimethylaminopyridine.

According to another process F compounds of formula (I) wherein $R^4$ is a group of formula (III) $R^{12}$ and $R^{15}$ represent a double bond and $R^{13}$ and $R^{14}$ are hydrogen may be prepared by cyclisation of a compound of formula (XVII) wherein $R^1$, $R^2$, $R^5$, $R^9$ and $R^{20}$ have the meanings defined in formula (I) or are groups convertible thereto.

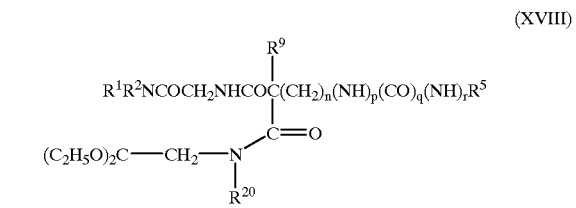
(XVIII)

by reaction with p-toluene sulphone acid in a suitable solvent such as a hydrocarbon e.g. toluene. Conveniently the reaction is carried out with heating.

Compounds of the invention may also be converted into other compounds of the invention. Thus compounds wherein the groups $R^5$ or $R^6$ contain an alkoxycarbonyl grouping may be converted into the corresponding carboxyl groupings by conventional hydrolysis procedures e.g. reaction with hydrochloric acid in a suitable solvent such as dioxan, or with trifluoroacetic acid.

Alternatively the hydrolysis may be carried out using any alkali metal hydroxide or alkali metal carbonate in a suitable solvent.

Compounds of formula (I) wherein $R^5$ is heteroaryl group e.g. indolyl substituted on the nitrogen atom therein with a carboxyalkyl group may be prepared by reaction of the corresponding compound of formula (I) containing the required NH grouping with a $C_{1-4}$alkoxycarbonylakyl halide e.g. bromide in the presence of a strong base such as sodium hydride and in an aprotic solvent, followed by conversion of the alkoxycarbonyl group into the carboxyl group by conventional acid or alkaline hydrolysis.

Compounds of formula (I) wherein Y is the group SO or $SO_2$ may be prepared by oxidation of the corresponding compound of formula (I) wherein Y is S. Thus compounds of formula (I) wherein Y is SO may be prepared by reaction of the corresponding compound wherein Y is S with a periodate e.g. sodium periodate in a solvent such as an aqueous alkanol e.g. aqueous methanol. Compounds of formula (I) where Y is SO may be prepared by oxidation of the corresponding compound wherein Y is S or SO. This oxidation is conveniently carried out using a peracid such as metachloroperbenzoic acid in a solvent such as dichloromethane.

The amine intermediates (V) and (VI) are either known compounds or may be prepared by analogous methods described for structurally similar or related compounds. Thus compounds of formula (V) wherein the groups $R^3$ and $R^6$ do not link together to form a chain may be prepared by the application of standard peptide chemistry to the appropriate α-amino acids or protected derivatives thereof. For example compound (V) may be prepared by condensation of the amine (XIX)

(XIX)
$$R^1R^2NCOCH_2NHR^3$$

-continued

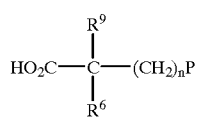

(XX)

with the carboxylic acid (XX) wherein P is a protected amino group followed by removal of the protecting group. Alternatively the amide (XXI)

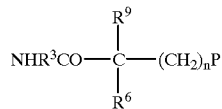

(XXI)

may be reacted with the haloamide $R^1R^2NCOCH_2Hal$ (XXII) in the presence of a strong base such as sodium hydride followed by removal of the amino protecting group.

The compounds of formula (XIX), (XX), (XXI) and (XXII) may be prepared by conventional procedures.

Compounds of formula (V) wherein $R^3$ and $R^6$ are linked to form a cyclic structure may also be prepared by conventional procedures. Thus for example compounds of formula (V) wherein Y is sulphur and Z is $CH_2$ may be prepared using procedures such as described in J Med. Chem. 1985, 28, 1517. Compounds of formula (V) wherein Y and Z are both $CH_2$ may be prepared using procedures described in Tetrahedron Letters 1994, 35, 3239. Compounds of formula (I) where Y is CO and Z is $CH_2$ may be prepared using the general procedures described in Australian J. Chem. 1978, 31,39 and 1980, 33, 633.

Compounds of formula (V) wherein Y is the group —N=CCH$_3$— may be prepared using the general procedures described khim Geterotsiki Soedin 1978, 1558.

Compounds of formula (XII) may be prepared from the corresponding amine (XXIII)

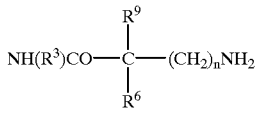

(XXIII)

using the general procedures described above for preparing compounds of formula (I) from the amine (V). More specific procedures for preparing the intermediates required for the synthesis of compounds of formula (I) are described in the specific examples given below.

In order that the invention may be more fully understood the following examples are given by way of illustration only. In the intermediates and examples unless otherwise stated.

All chemicals and solvents are reagent grade unless otherwise specified. The following have been addreviated: (AIBN), 2,2'-Azobis(2-methylpropionitrile); (Boc), tert-butoxycarbonyl; (BOP), Benzotriazol-1-yloxy-tris (dimethylamino)phosphonium hexafluorophosphate; (Cbz), benzyloxycarbonyl; (CDI), 1,1-Carbonyidiimdazole; (mCPBA) m-chloroperbenzoic acid; (DCM), Dichloromethane; (DMAP), 4-Dimethylaminopyridine; (DMF), dimethylformamide; (DMAP), p-Dimethylaminopyridine; (DMF), Dimethyl formamide; (EDC), 1-(3-Dimethylaminopropyl)-3-ethylcarbodiimide hydrochloride; (EtOAc), Ethyl acetate; (Et$_2$O), Diethyl ether; (HOBT), Hydroxybenztriazole; (NBS), N-Bromosuccinimide; (rt), Room temperature; (RP-HPLC), Reverse phase preparative HPLC; (TEA), Triethylamine; (TFA),Trifluoroacetic acid; (THF), Tetrahydrofuran. RP-HPLC was conducted using a Waters Model 3000 Delta Prep equipped with a Delta-pak radial compression cartridge (C18, 300 A, 15 $\mu$, 47 mm×300 mm) as the stationary phase unless otherwise specified. The mobile phase employed 0.1% aqueous TFA with acetonitrile (Burdick and Jackson) as the organic modifier. Linear gradients were used in all cases and the flow rate was 100 ml/min (to=5 min). Analytical purity was assessed by RP-HPLC using a Waters 600E system equipped with a Waters 990 dioda array spectrometer ($\lambda$ range 200–400 nm). The stationary phase was a Vydac C18 column (5 $\mu$, 4.6 mm×200 mm). The mobile phase employed 0.1% aqueous TFA with acetonitrile (Burdick and Jackson) as the organic modifier. Linear gradients were used in all cases and the flow rate was 1.5 ml/min (to=2.8 min).

EXAMPLE 1

(R)-4-{[Isopropyl-(4-methoxy-phenyl)-carbamoylmethyl]-phenyl-carbamoyl}-4-(3-phenyl-ureido)-butyric acid.

Intermediate 1A

A solution of N-Boc-D-glutamic acid gamma tert-butyl ester (2.00 g), BOP (2.13 g), HOBT (902 mg), DMAP (773 mg) and aniline (613 mg) in DMF (5 mL) was stirred at rt overnight. The reaction mixture was diluted with ethyl acetate (50 mL) and extracted into 1N aqueous sodium hydroxide solution (2×20 mL), water (20 mL), 1N hydrochloric acid (2×20 mL), water (2×20 mL), brine (20 mL), dried (MgSO$_4$) and concentrated in vacuo to afford the titled product (1.71 g) as a colorless glassy foam. $^1$H NMR (300 MHz, CDCl$_3$) d 1.4 (s, 18H), 1.95 (m, 1H), 2.12 (m, 1H), 2.37(m, 1H), 2.51 (m, 1H), 4.22 (br, 1H), 5.40 (d, J=6.0 Hz, 1H), 7.09 (t, J=7.0 Hz, 1H), 7.29 (t, J=7.0 Hz, 2H), 7.50 (d, J=7.0 Hz, 2H), 8.55 (s, 1H).

Intermediate 1B

Sodium hydride (60% in oil, 74.5 mg, 1.78 mmol) was added to a 0° C. solution of Intermediate 1A (673 mg, 1.78 mmol) in DMF (5 mL) and the resultant mixture stirred at 0° C. for 4 min prior to the addition of 2-bromo-N-isopropyl-N-(4-methoxyphenyl) acetamide (509 mg, 1.78 mmol) and the resultant mixture was stirred at rt overnight. The reaction mixture was diluted with ethyl acetate (50 mL) and extracted into water (3×20 mL), washed with brine (20 mL), dried (MgSO$_4$) and concentrated in vacuo to afford the titled product (901 mg) as a colorless glass. TLC (30% ethyl acetate/hexane) R$_f$=0.18. $^1$H NMR (300 MHz, CDCl$_3$) d 0.87 (2×d, J=7.0 Hz, 6H), 1.22 (2×s, 18H), 1.58 (m, 1H), 1.72 (m, 1H), 1.97(m, 2H), 3.60 (d, J=15.8 Hz, 1H), 3.68 (s, 3H) 3.95 (d, J=15.8 Hz, 1H), 4.21 (br, 1H), 4.80 (sept, J=6.0 Hz, 1H), 5.12 (d, J=5.0 Hz, 1H), 7.0–7.5 (m, 9H).

Intermediate 1C

A mixture of Intermediate 1B (900 mg, 1.54 mmol) and 4N HCl in dioxane (10 mL) was stirred at rt for 2 h. Diethyl ether (80 mL) was added and the solvent was removed from the resultant precipitate by decanting. The residue was triturated with diethyl ether (3×80 mL) to afford the crude product (600 mg, 84%) as a colorless foam. $^1$H NMR (300 MHz, CDCl$_3$) d 0.97 (2×d, J=7.0 Hz, 6H), 1.62 (m, 1H), 1.78(m, 1H), 2.24(m, 2H), 3.64 (d, J=16.2 Hz, 1H), 3.78 (s, 3H), 3.90 (br, 1H), 4.05 (d, J=16.2 Hz, 1H), 4.80 (sept, J=6.0 Hz, 1H), 7.0–7.5 (m, 9H), 8.40 (br, 2H).

EXAMPLE 1

(R)-4-{[Isopropyl-(4-methoxy-phenyl)-carbamoylmethyl]-phenyl-carbamoyl}-4-(3-phenyl-ureido)-butyric acid.

A solution of phenyl isocyanate (51.5 mg, 0.414 mmol) in dichloromethane (2.0 mL) was added to a solution of Intermediate 1C (192 mg, 0.414 mmol) and triethylamine (0.142 mL) in dichloromethane (4.0 mL) and the resultant mixture stirred at rt for 4 h. The solvents were removed in vacuo and the residue partitioned between ethyl acetate (30 mL) and 1N hydrochloric acid (20 mL). The organics were washed with water (3×20 mL), brine (20 mL), dried (MgSO$_4$) and concentrated in vacuo to afford the crude product (212 mg) as a colorless glassy foam. RP-HPLC (48% to 64%, 30 min) gave the titled product (86.7 mg) as a white lyophile. (45% to 64%, 30 min) T$_r$=16.40 min. $^1$H NMR (300 MHz, CDCl$_3$) d 0.87 (2×d, J=7.0 Hz, 6H), 1.82 (m, 1H), 1.98(m, 2H), 2.24(m, 1H), 3.29(d, J=16.8 Hz, 1H), 3.52 (s, 3H), 4.20 (d, J=16.8 Hz, 1H), 4.54 (m, 1H), 4.95 (sept, J=6.0 Hz, 1H), 6.25 (d, J=7.0 Hz, 1H), 6.62 (m, 2H), 6.85–7.40 (m, 11H), 8.20 (br, 1H). C$_{30}$H$_{34}$N$_4$O$_6$ requires m/z 546.6233; found 546.6254

EXAMPLE 2

(R)-4-{[Isopropyl-(4-hydroxy-phenyl)-carbamoylmethyl]-phenyl-carbamoyl}-4-(3-phenyl-ureido)-butyric acid.

Intermediate 2A

Acetone (14.1 mL) was added to a mixture of p-benzyloxyaniline (18.76 g, 94.2 mmol) and sodium cyanoborohydride (1M in THF, 207 mL, 207 mmol) in methanol (250 mL) and acetic acid (6.5 mL) and the resultant mixture was stirred at room temperature for 16 h. The reaction mixture was diluted with saturated aqueous sodium bicarbonate (50 mL) and then the solvents concentrated in vacuo. The residue was extracted into ethyl acetate (3×100 mL) and then the combined organics washed with brine (100 mL), dried (K$_2$CO$_3$) and then the solvents concentrated in vacuo to afford a black oil. Flash column chromatography (15% ethyl acetate/hexane) gave the titled product (9.64 g) as a pale brown oil. TLC (20% ethyl acetate/hexane) R$_f$=0.78. $^1$H NMR (300 MHz, CDCl$_3$) d 1.04 (d, J=6.9 Hz, 6H), 3.72 (sept, J=6.9 hz, 1H), 4.99 (s, 2H), 6.58 (d, J=8.8 Hz, 2H), 6.86 (d, J=9.0 Hz, 2H), 7.3–7.5 (m, 5H).

Intermediate 2B

Bromoacetyl bromide (0.369 mL) in methylene chloride (5 mL) was added dropwise to a 0° C. solution of intermediate 2A (1.00 g, 4.14 mmol) in methylene chloride (10 mL) and triethylamine (0.582 mL) and the resultant mixture was stirred at 0° C. for 5 h and then allowed to attain rt over 10 h. The reaction mixture was washed with 1N hydrochloric acid (3×30 mL), water (3×20 mL), brine (20 mL), dried (K$_2$CO$_3$) and concentrated in vacuo to afford the titled product (1.46 g) as a brown solid. TLC (20% ethyl acetate/hexane) R$_f$=0.38. $^1$H NMR (300 MHz, CDCl$_3$) d 1.04 (d, J=6.9 Hz, 6H), 3.54 (s, 2H), 5.08 (sept, J=6.9 hz, 1H), 5.29 (s, 2H), 7.0 (d, J=8.8 Hz, 2H), 7.11 (d, J=9.0 Hz, 2H), 7.3–7.5 (m, 5H).

Intermediate 2C

Sodium hydride (60% in oil, 32 mg) was added to a 0° C. solution of Intermediate 1A (287 mg) in DMF (3.00 mL) and the resultant mixture stirred at 0° C. for 4 min prior to the addition of intermediate 2B (264 mg) and the resultant mixture was stirred at rt overnight. The reaction mixture was diluted with ethyl acetate (50 mL) and extracted into water (3×20 mL), washed with brine (20 mL), dried (MgSO$_4$) and concentrated in vacuo to afford the crude product (370 mg) as a colorless glassy foam. Flash column chromatography (30% ethyl acetate/hexane) gave the titled product (230 mg) as a colorless glass. TLC (30% ethyl acetate/hexane) R$_f$=0.26. $^1$H NMR (300 MHz, CDCl$_3$) d 1.04 (2×d, J=7.0 Hz, 6H), 1.36 (2×s, 18H), 1.71 (m, 1H), 1.86 (m, 1H), 2.11 (m, 2H), 3.78 (d, J=16.0 Hz, 1H), 4.10 (d, J=16.0 Hz, 1H), 4.38 (br, 1H), 4.93 (sept, J=6.0 Hz 1H), 5.07 (s, 2H) 5.27 (d, J=7.0 Hz, 1H), 6.95–7.4 (m, 15H).

Intermediate 2D

A mixture of Intermediate 2C (230 mg) and 4N HCl in dioxane (2 mL) was stirred at rt for 3 h. Diethyl ether (30 mL) was added and the solvent was removed from the resultant precipitate by decanting. The residue was triturated with diethyl ether (3×30 mL) to afford the titled product (174 mg) as a white solid. $^1$H NMR (300 MHz, CDCl$_3$) d 0.96 (2×d, J=7.0 Hz, 6H), 1.59 (m, 1H), 1.79 (m, 1H), 2.11 (m, 2H), 3.76 (d, J=16.0 Hz, 1H), 3.90 (br, 1H), 4.04 (d, J=16 Hz, 1H), 4.79 (sept, J=6.0 Hz 1H), 5.07 (s, 2H), 6.95–7.4 (m, 15H), 8.25 (br, 3H).

Intermediate 2E

A solution of phenyl isocyanate (18.4 mg) in dichloromethane (1.0 mL) was added to a solution of Intermediate 2D (50 mg) and triethylamine (0.050 mL) in dichloromethane (1.0 mL) and the resultant mixture stirred at rt for 4 h. The solvents were removed in vacuo and the residue partitioned between ethyl acetate (30 mL) and 1N hydrochloric acid (20 mL). The organics were washed with water (3×20 mL), brine (20 mL), dried (MgSO$_4$), and concentrated in vacuo to afford the desired product (92 mg) as a colorless glassy foam. $^1$H NMR (300 MHz, CDCl$_3$) d 0.96 (2×d, J=7.0 Hz, 6H), 1.92 (m, 1H), 2.02 (m, 1H), 2.21 (m, 1H), 2.42 (m, 1H) 3.36 (d, J=16.6.0 Hz, 1H), 4.37 (d, J=16.6.0 Hz, 1H), 4.71 (m,1H), 4.84 (s, 2H), 5.17 (sept, 1H), 6.33 (d, J=9.0 Hz, 1H), 6.56 (d, J=9.3 Hz, 1H), 6.85–7.40 (m, 15H), 7.60 (d, J=7.1 Hz, 2H) 8.36 (s, 1H).

EXAMPLE 2

(R)-4-{[Isopropyl-(4-hydroxy-phenyl)-carbamoylmethyl]-phenyl-carbamoyl}-4-(3-phenyl-ureido)-butyric acid.

A mixture of Intermediate 2E (80 mg 0.128 mmol), 10% Pd/C (9 mg) and ethanol was stirred under an atmosphere of hydrogen for 18 h. The solids were removed by filtration through celite and the filtrate was was concentrated in vacuo. RP-HPLC (48% to 64%, 30 min) gave the titled product (54 mg) as a white lyophile. (45% to 64%, 30 min) T$_r$=13.31 min. $^1$H NMR (300 MHz, CDCl$_3$) d 1.02 (2×d, J=7.0 Hz, 6H), 1.92 (m, 3H), 2.17 (m, 1H), 3.47 (d, J=16.2 Hz, 1H), 4.24 (d, J=16.2 Hz, 1H), 4.65 (m, 1H) 4.96 (sept 1H), 6.85–7.85 (m, 15H), 8.90 (s, 1H). C$_{29}$H$_{32}$N$_4$O$_6$ requires m/z 532.5964; found 532.6001

EXAMPLE 3

(R)-4-{[(4-Hydroxy-phenyl)-isopropyl-carbamoylmethyl]-phenyl-carbamoyl}-4-[(1H-indole-2-carbonyl )-amino]-butyric acid.

Intermediate 3A

A mixture of indole-2-carboxylic acid (23.8 mg, 0.148 mmol)) and CDI (23.9 mg, 0.148 mmol) in THF (2 mL) was stirred at rt for 16 h. A mixture of Intermediate 2D (80.0 mg, 0.148 mmol) and triethylamine (0.050 mL) in THF (3.0 mL) was added and the resultant solution stirred at rt for 4 h. The solvents were removed in vacuo and the residue partitioned between ethyl acetate (30 mL) and 1N hydrochloric acid (20 mL). The organics were washed with water (3×20 mL), brine (20 mL), dried (MgSO$_4$), and concentrated in vacuo to afford the desired product (42 mg) as a colorless glassy foam. NMR (300 MHz, CDCl$_3$) d 1.0 (2×d, J=7.0 Hz, 6H), 1.88 (m, 1H), 2.0 (m, 1H), 2.21 (m, 1H), 2.42 (m, 1H), 3.71 (d, J=16.0 Hz, 1H), 3.78 (m, 1H), 4.34 (d, J=16.0 Hz, 1H), 5.06 (m 3H), 7.0–7.85 (m, 21H), 9.08 (s, 1H).

EXAMPLE 3

(R)-4-{[(4-Hydroxy-phenyl)-isopropyl-carbamoylmethyl]-phenyl-carbamoyl}-4-[(1H-indole-2-carbonyl)-amino]-butyric acid.

A mixture of Intermediate 3A (42 mg 0.060 mmol), 10% Pd/C (9 mg) and ethanol was stirred under an atmosphere of hydrogen for 16 h. The solids were removed by filtration through celite and the filtrate was was concentrated in vacuo. RP-HPLC (48% to 64%, 30 min) gave the titled product (27.6 mg) as a white lyophile. (45% to 64%, 30 min) $T_r$=10.60 min. $^1$H NMR (300 MHz, CDCl$_3$) d 1.10 (2×d, J=7.0 Hz, 6H), 1.99 (m, 3H), 2.07(m, 1H), 3.77 (d, J=16.1 Hz, 1H), 4.34 (d, J=16.1 Hz, 1H), 4.96 (m 2H), 7.0–7.95 (m, 16H), 10.90 (s, 1H). $C_{31}H_{32}N_4O_6$ requires m/z 556.6184; found 556.6151

EXAMPLE 4

(R)-4-[(Isopropyl-phenyl-carbamoylmethyl)-phenyl-carbamoyl]-4-(3-phenyl-ureido)-butyric acid.

Intermediate 4A

Sodium hydride (60% in oil, 41.6 mg) was added to a 0° C. solution of Intermediate 1A (378 mg) in DMF (4.00 mL) and the resultant mixture stirred at 0° C. for 4 min prior to the addition of 2-bromo-N-isopropyl-N-phenyl acetamide (251 mg) and the resultant mixture was stirred at rt overnight. The reaction mixture was diluted with ethyl acetate (50 mL) and extracted into water (3×20 mL), washed with brine (20 mL), dried (MgSO$_4$) and concentrated in vacuo to afford the crude product (470 mg) as a colorless glassy foam. Flash column chromatography (20% ethyl acetate/hexane) gave the titled product (274 mg) as a colorless glass. $^1$H NMR (300 MHz, CDCl$_3$) d 1.0 (2×d, J=7.0 Hz, 6H), 1.4 (2×s, 18H), 1.68 (m, 1H), 1.92 (m, 1H), 2.07 (m, 2H), 3.70 (d, J=17.0 Hz, 1H), 4.04 (d, J=17.0 Hz, 1H), 4.38 (br, 1H), 4.96 (sept, J=6.0 Hz, 1H), 5.26 (d, J=6.0 Hz, 1H), 7.0–7.5 (m, 10 H).

Intermediate 4B

A mixture of Intermediate 4A (274 mg) and 4N HCl in dioxane (2 mL) was stirred at rt for 3 h. Diethyl ether (30 mL) was added and the solvent was removed from the resultant precipitate by decanting. The residue was triturated with diethyl ether (3×30 mL) to afford the titled product (137 mg) as a white solid. $^1$H NMR (300 MHz, CDCl$_3$) d 1.0 (2×d, J=7.0 Hz, 6H), 1.90 (m, 1H), 2.10 (m, 1H), 2.37(m, 1H), 2.61 (m, 1H), 3.60 (d, J=17.0 Hz, 1H), 4.20 (br, 1H), 4.38 (d, J=17.0 Hz, 1H), 4.96 (sept, J=6.0 Hz, 1H), 7.0–7.5 (m, 10 H), 8.2 (br, 3H).

EXAMPLE 4

(R)-4-[(Isopropyl-phenyl-carbamoylmethyl)-phenyl-carbamoyl]-4-(3-phenyl-ureido)-butyric acid.

A solution of phenyl isocyanate (17.1 mg) in dichloromethane (1.0 mL) was added to a solution of Intermediate 4B (60 mg) and triethylamine (0.047 mL) in dichloromethane (1.0 mL) and the resultant mixture stirred at rt for 4 h. The solvents were removed in vacuo and the residue partitioned between ethyl acetate (30 mL) and 1N hydrochloric acid (20 mL). The organics were washed with water (3×20 mL), brine (20 mL), dried (MgSO$_4$) and concentrated in vacuo to afford the crude product (70 mg) as a colorless glassy foam. RP-HPLC (45% to 64%, 30 min) gave the titled product (54 mg) as a white lyophile. (45% to 64%, 30 min) $T_r$=21.3 min. $^1$H NMR (300 MHz, CDCl$_3$) d 1.0 (2×d, J=7.0 Hz, 6H), 1.90 (m, 1H), 2.07 (m, 1H), 2.20 (m, 1H), 2.41 (m, 1H), 3.40 (d, J=17.2 Hz, 1H), 4.36 (d, J=17.2 Hz, 1H), 4.70 (m, 1H), 5.20 (sept, J=6.0 Hz, 1H), 6.57 (d, J=7.0 Hz, 1H), 6.88 (m, 4H), 7.10 (m, 4H), 7.21 (br, 2H), 7.38 (m, 4H), 7.59 (d, J=7.0 Hz, 2H), 8.30 (s, 1H). $C_{29}H_{32}N_4O_5$ requires m/z 516.5970 found 516.5936

EXAMPLE 5

(R)-4-[(1H-indole-2-carbonyl)-amino]-4-[(isopropyl-phenyl-carbamoylmethyl)-phenyl-carbamoyl]-butyric acid.

A mixture of Indole-2-carboxylic acid (28.5 mg) and CDI (28.6 mg) in THF (2 mL) was stirred at rt overnight and then a mixture of Intermediate 4B (77 mg) and triethylamine (0.060 mL) in THF (3 mL) was added and the resultant mixture was stirred at rt overnight. The solvents were removed in vacuo and the residue partitioned between ethyl acetate (30 mL) and 1N hydrochloric acid (20 mL). The organics were washed with water (3×20 mL), brine (20 mL), dried (MgSO$_4$) and concentrated in vacuo to afford the crude product (90 mg) as a colorless glassy foam. RP-HPLC (48% to 64%, 30 min) gave the titled product (78 mg) as a white lyophile. (45% to 64%, 30 min) $T_r$=21.34 min. $^1$H NMR (300 MHz, CDCl$_3$) d 1.04 (2×d, J=7.0 Hz, 6H), 1.98 (m, 1H), 2.07 (m, 1H), 2.41 (m, 2H), 3.62 (d, J=16.9 Hz, 1H), 4.22 (d, J=16.9 Hz, 1H), 4.97 (m, 2H), 6.95–7.7 (m, 15H) 9.18 (s, 1H), 9.77 (s, 1H). $C_{31}H_{33}N_4O_5$ requires m/z 541.2451; found 541.2453.

EXAMPLE 6

(R)-4-[(Isopropyl-phenyl-carbamoylmethyl)-pentyl-carbamoyl]-4-(3-phenyl-ureido)-butyric acid.

Intermediate 6A 2-bromo-N-isopropyl-N-phenyl acetamide (515 mg) was added to a stirring solution of pentylamine (5.00 g) in methanol (5.0 mL) and the resultant mixture was stirred at rt overnight. The pentylamine was removed in vacuo and the residue was triturated with hexane and the triturant was concentrated in vacuo to afford the titled product (470 mg) as a yellow oil. $^1$H NMR (300 MHz, CDCl$_3$) d 0.82 (m, 5H), 1.04 (2×d, J=7.0 Hz, 6H), 1.2–1.4 (m, 4H), 2.4 (t, J=7.0 Hz, 2H), 2.84 (s, 2H), 4.98 (sept, J=6.0 Hz 1H), 7.03 (br, 2H), 7.42 (br, 3H).

Intermediate 6B

A solution of N-Boc-D-glutamic acid gamma benzyl ester (605 mg), BOP (771 mg), HOBT (245 mg), DMAP (210 mg) and Intermediate 6A (470 mg) in DMF (2 mL) was stirred at rt overnight. The reaction mixture was diluted with ethyl acetate (50 mL) and extracted into 1N aqueous sodium hydroxide solution (2×20 mL), water (20 mL), 1N hydrochloric acid (2×20 mL), water (2×20 mL), brine (20 mL), dried (MgSO$_4$) and concentrated in vacuo to afford the crude product (690 mg). Flash column chromatography (5% methanol in methylene chloride) gave the titled product (390 mg) as a colorless glass. Due to amide rotamers the $^1$H NMR spectrum for this intermediate was difficult to assign.

Intermediate 6C

A mixture of Intermediate 6B (390 mg) and 4N HCl in dioxane (3 mL) was stirred at rt for 3 h. Diethyl ether (30 mL) was added and the solvent was removed from the resultant precipitate by decanting. The residue was triturated with diethyl ether (3×30 mL) to afford the titled product (174 mg) as a brown glass which was used crude in the next step. Due to amide rotamers the $^1$H NMR spectrum for this intermediate was difficult to assign. Clearly assignable peaks were: −3.4 (d, J=16.0 Hz, 1H), 3.79 (d, J=16.0 Hz, 1H), Intermediate 6D A solution of phenyl isocyanate (14.0 mg) in dichloromethane (1.0 mL) was added to a solution of Intermediate 6C (60 mg) and triethylamine (0.0191 mL) in dichloromethane (1.0 mL) and the resultant mixture stirred at rt for 4 h. The solvents were removed in vacuo and the residue partitioned between ethyl acetate (30 mL) and 1N hydrochloric acid (20 mL). The organics were washed with water (3×20 mL), brine (20 mL), dried (MgSO$_4$) and concentrated in vacuo to afford the crude product (65 mg) as a colorless glassy foam. Due to amide rotamers the $^1$H NMR spectrum for this intermediate was difficult to assign. Clearly assignable peaks were: −3.42 (d, J=16.0 Hz, 1H), 3.76 (d, J=16.0 Hz, 1H).

EXAMPLE 6

(R)4-[(Isopropyl-phenyl-carbamoylmethyl)-pentyl-carbamoyl]-4-(3-phenyl-ureido)-butyric acid.

A mixture of Intermediate 6D (54.0 mg) and 10% Pd/C (10 mg) in ethanol was stirred vigorously under an atmosphere of hydrogen for 72 h. The solids were removed by filtration and the filtrate concentrated in vacuo to afford the crude adduct. RP-HPLC (45% to 64%, 30 min) gave the titled product (23 mg) as a white lyophile. (45% to 64%, 30 min) T$_r$=34.5 min. Due to amide rotamers the $^1$H NMR spectrum for this compound was difficult to assign. C$_{28}$H$_{39}$N$_4$O$_5$ requires m/z 511.2920 found 511.2932

EXAMPLE 7

(R)-4-[(1H-indole-2-carbonyl)-amino]-4-[(isopropyl-phenyl-carbamoylmethyl)-pentyl-carbamoyl]-butyric acid.

Intermediate 7A

A solution of Intermediate 6C (126 mg), BOP (102 mg), HOBT (33 mg), DMAP (28 mg) and indole-2-carboxylic acid (39 mg) in DMF (1 mL) was stirred at rt overnight. The reaction mixture was diluted with ethyl acetate (50 mL) and extracted into 1N aqueous sodium hydroxide solution (2×20 mL), water (20 mL), 1N hydrochloric acid (2×20 mL), water (2×20 mL), brine (20 mL), dried (MgSO$_4$) and concentrated in vacuo to afford the titled product (136 mg) as a brown glass which was used crude in the next reaction. Due to amide rotamers the $^1$H NMR spectrum for this intermediate was difficult to assign.

EXAMPLE 7

(R)-4-[(1H-indole-2-carbonyl)-amino]-4-[(isopropyl-phenyl-carbamoylmethyl)-pentyl-carbamoyl]-butyric acid.

A mixture of Intermediate 7A (136 mg), 1N NaOH (0.25 mL), water (1.5 mL) and THF (3.2 mL) was stirred together at rt for 16 h and then the reaction mixture was acidified to pH 3 (2N hydrochloric acid) and the solvents removed in vacuo. The residue was partitioned between ethyl acetate (3×20 mL) and water (20 mL). The organics were washed with water (3×20 mL), brine (20 mL), dried (MgSO$_4$) and concentrated in vacuo to afford the crude product (101 mg) as a glassy foam. RP-HPLC (60% to 68%, 30 min) gave the titled product (43 mg) as a white lyophile. (60% to 68%, 30 min) T$_r$=19.6 min. Due to amide rotamers the $^1$H NMR spectrum for this example was difficult to assign. C$_{30}$H$_{39}$N$_4$O$_5$ requires m/z 535.2920; found 535.2930.

EXAMPLE 8

(R)-3-{3-[(2-Chloro-phenyl)-(isopropyl-phenyl-carbamoylmethyl)-carbamoylmethyl]-ureido}-benzoic acid Intermediate 8A Potassium phthalimide (4.53 g, 24.5 mmol) was added to a solution of (2-chlorophenyl)chloroactamide (5.00 g. 24.5 mmol) in DMF (30 mL) and the resultant mixture was stirred at rt for 16 h. The reaction mixture was poured into water (150 mL) and extracted into ethyl acetate (5×80 mL). The combined organics were washed with water (3×100 mL), brine (100 mL), dried (MgSO$_4$) and concentrated in vacuo to afford the titled product (4.97 g) as a white solid. Note that during the above extraction a precipitate formed which was removed by filtration to afford the titled product also (1.46 g), total yield 83.7%. TLC (30% ethyl acetate in hexane) R$_f$=0.21. $^1$H NMR (300 MHz, CDCl$_3$) d 7.10 (dt, J=6.0,1.0 Hz, 1H), 7.22 (m, 1H), 7.39 (dd, J=6.0, 1.0 Hz, 1H), 7.77 (m, 2H), 7.95 (m, 3H), 8.32 (br, 1H).

Intermediate 8B

Sodium hydride (60% in oil, 142 mg, 3.57 mmol) was added to a 0° C. suspension of Intermediate 8A (1.12 9, 3.57 mmol) in DMF (10 mL) and the resultant mixture stirred at 0° C. for 30 min prior to the addition of 2-bromo-N-isopropyl-N-phenyl acetamide (893 mg, 5.57 mmol) and the resultant mixture was stirred at rt overnight. The reaction mixture was poured into 2N hydrochloric acid (50 mL) and extracted into ethyl acetate (3×50 mL). The combined organics were washed with water (3×30 mL), brine (30 mL), dried (MgSO$_4$) and concentrated in vacuo to afford the crude product (2.67 g). Recrystalisation from ethyl acetate gave the titled product (1.04 g) as a white solid TLC (5% methanol in methylene chloride) R$_f$=0.32. $^1$H NMR (300 MHz, CDCl$_3$) d 1.03 (m, 6H), 3.22 (d, J=17.0 Hz, 1H), 3.92 (d, J=16.8 Hz, 1H), 4.22 (d, J=16.8 Hz, 1H), 4.62 (d, J=17.0 Hz, 1H), 4.97 (sept, J=7.0 Hz, 1H), 7.40 (m, 8H), 7.65 (m, 2H), 7.82 (m, 2H), 8.17 (dd, J=5.0, 0.7.0 Hz, 1H).

Intermediate 8C

A mixture of Intermediate 8B (800 mg, 1.63 mmol) and methyl hydrazine (215 mg) in ethanol (20 mL) was stirred at rt for 16 h. The solvents were removed in vacuo and the residue was partitioned between ethyl acetate (20 mL) and 2N hydrochloric acid (2×10 mL). The combined aqueous phase was extracted into ethyl acetate (10 mL), basified to pH 14 (2N aqueous sodium hydroxide) and extracted into ethyl acetate (3×20 mL). The combined latter organics were dried (K$_2$CO$_3$) and concentrated in vacuo to afford the titled product as a yellow glass (420 mg, 72%). TLC (10% methanol in methylene chloride) R$_f$=0.63. $^1$H NMR (300 MHz, CDCl$_3$) d 1.03 (d, J=7.0 Hz, 3H), 1.13 (d, J=7.0 Hz, 3H), 2.97 (d, J=16.6 Hz, 1H), 3.20 (dd, J=14.2, 2.2 Hz, 2H), 4.62 (d, J=16.6 Hz, 1H), 4.97 (sept, J=7.0 Hz, 1H), 6.95 (br, 2H), 7.40 (m, 9H), 7.92 (m, 1H).

Intermediate 8D

Triphosgene (19.7 mg, 0.070 mmol) was added to a 0° C. solution of $^t$Butyl m-aminobenzoate (38.7 mg, 0.200 mmol) and triethylamine (0.060 mL) and the resultant mixture stirred at 0° C. for 1 h. A solution of Intermediate 8C (72.0 mg, 0.200 mmol) in THF (10 mL) was added and the resultant mixture stirred at rt for 48 h. The solvents were removed in vacuo and the residue dissolved in ethyl acetate (30 mL) and the solution extracted into 1N hydrochloric acid (2×20 mL), washed with 2N aqueous sodium hydrogen carbonate (20 mL), dried (MgSO$_4$) and concentrated in vacuo to afford the crude titled product (104 mg, 91%) as a colorless glass. $^1$H NMR (300 MHz, CDCl$_3$) d 0.98 (2×d, J=6.4 Hz, 6H), 1.55 (s, 9H), 3.25 (d, J=16.5 Hz, 1H), 3.75 (dd, J=17.5, 5.3 Hz, 1H), 3.84 (dd, J=17.5, 4.4 Hz, 1H), 4.61 (d, J=16.5 Hz, 1H), 4.89 (sept, J=6.4 Hz, 1H), 6.10 (t, J=4.9 Hz, 1H), 6.90 (br, 1H), 7.10–7.60 (m, 13H).

EXAMPLE 8

(R)-3-{3-[(2-Chloro-phenyl)-(isopropyl-phenyl-carbamoylmethyl)-carbamoylmethyl]-ureido}-benzoic acid A mixture of Intermediate 8D (103 mg) and 4N HCl in dioxane (2 mL) was stirred at rt for 4 h. The solvent was removed in vacuo and the residue was triturated with hexanes (3×80 mL) to afford the crude product (93 mg). Recrystalisation from ethyl acetate:hexane:methanol (50:50:1) gave the titled product (58 mg) as a white powder. RP-HPLC (48% to 64%, 30 min) gave the titled product (44 mg) as a white lyophile. (45% to 64%, 30 min) T$_r$=19.61 min. $^1$H NMR (300 MHz, DMSO-d$_6$) 0.92 (d, J=7.0 Hz, 3H), 0.97 (d, J=7.0 Hz, 3H), 3.07 (d, J=14.5 Hz, 1H), 3.20 (dd, J=11.5, 0.6.0 Hz, 2H), 4.38 (d, J=14.5 Hz, 1H), 4.89 (sept, J=7.0 Hz, 1H), 6.35 (br, 1H), 7.05–7.60 (m, 13H), 9.03 (s, 1H) C$_{27}$H$_{27}$N$_4$O$_5$Cl requires m/z 522.9880; found 522.9851

EXAMPLE 9

(R)-(2-Chloro-phenyl)-N-(isopropyl-phenyl-carbamoylmethyl)-2-[3-(3-methylsulfamyl-phenyl)-ureido]-acetamide.

A solution of m-thiomethylphenyl isocyanate (18.3 mg, 0.11 mmol) in dichloromethane (1.0 mL) was added to a solution of Intermediate 8C (40 mg, 0.200 mmol) in dichloromethane (1.0 mL) and the resultant mixture stirred at rt for 72 h. The solvents were removed in vacuo to afford the crude product. Recrystalisation from ethyl acetate:hexane (3:1) gave the titled product (44 mg, 81%) as a white powder. RP-HPLC (45% to 64%, 30 min) T$_r$=13.31 min. $^1$H NMR (300 MHz, CDCl$_3$) d 0.98 (2×d, J=6.8 Hz, 6H), 2.44 (s, 3H), 3.23 (d, J=16.6.0 Hz, 1H), 3.68 (dd, J=17.3, 4.6.0 Hz, 1H), 3.84 (dd, J=17.3, 4.4 Hz, 1H), 4.60 (d, J=16.6.0 Hz, 1H), 4.93 (sept, J=6.8 Hz, 1H), 5.92 (t, J=4.9 Hz, 1H), 6.90 (d, J=7.8 Hz, 1H), 7.00–7.50 (m, 13H), 7.89 (m, 1H). C$_{27}$H$_{29}$N$_4$O$_3$CIS requires m/z 525.0711; found 525.0747

EXAMPLE 10

(R)-1H-Indole-2-carboxylic acid[(2-chloro-phenyl)-(isopropyl-phenyl-carbamoylmethyl)-carbamoylmethyl]-amide.

A solution of intermediate 8C (192 mg), BOP (231 mg), HOBT (73.5 mg), and indole-2-carboxylic acid (85.9 mg) in DMF (1 mL) was stirred at rt overnight. The reaction mixture was diluted with ethyl acetate (30 mL) and extracted into 1N aqueous sodium hydroxide solution (2×30 mL), water (30 mL), brine (30 mL), dried (MgSO$_4$) and concentrated in vacuo to afford the crude product (190 mg). RP-HPLC (48% to 64%, 30 min) gave the titled product (104 mg) as a white lyophile. (45% to 64%, 30 min) T$_r$=21.81 min. $^1$H NMR (300 MHz, CDCl$_3$) d 1.02 (d, J=6.8 Hz, 3H), 1.12 (d, J=6.8 Hz, 3H), 3.21 (d, J=16.6.0 Hz, 1H), 3.83 (dd, J=18.3, 4.4 Hz, 1H), 3.84 (dd, J=18.3, 3.8 Hz, 1H), 4.64 (d, J=16.6.0 Hz, 1H), 4.99 (sept, J=6.8 Hz, 1H), 6.94 (s, 2H), 7.00–7.60 (m, 14H), 7.60 (d, J=8.1 Hz, 1H), 7.95 (m, 1H), 9.12 (s, 1H). C$_{28}$H$_{28}$N$_4$O$_3$Cl requires m/z 503.1854; found 503.1850.

EXAMPLE 11

(R)-(2-chloro-phenyl)-N-(isopropyl-phenyl-carbamoylmethyl)-2-(3-phenyl-ureido)-acetamide A solution of phenyl isocyanate (30.5 mg, 0.256 mmol) in dichloromethane (1.0 mL) was added to a solution of Intermediate 8C (92.0 mg, 0.256 mmol) in dichloromethane (1.0 mL) and the resultant mixture stirred at rt for 72 h. The solvents were removed in vacuo to afford the crude product (44 mg) as a colorless glassy foam. RP-HPLC (48% to 64%, 30 min) gave the titled product (19 mg) as a white lyophile. (45% to 64%, 30 min) T$_r$=23.2 min. $^1$H NMR (300 MHz, CDCl$_3$) d 1.03 (2×d, J=7.0 Hz, 6H), 3.17 (d, J=16.6.0 Hz, 1H), 3.90 (ABq, J=41.8, 17.5 Hz, 2H), 4.62 (d, J=16.6.0 Hz, 1H), 4.97 (sept, J=7.0 Hz, 1H), 6.95 (br, 2H), 7.40 (m, 15H), 7.92 (m, 1H). C$_{26}$H$_{27}$N$_4$O$_3$Cl requires m/z 478.9282; found 478.9251

EXAMPLE GH-12

(R)-3-{3-[(isopropyl-phenyl-carbamoylmethyl)-phenyl-carbamoylmethyl]-ureido}-benzoic acid.

Intermediate GH-12A

Bromacetyl bromide (11.0 mL, 125 mmol) in methylene chloride (50 mL) was added dropwise over 30 min to a 0° C. solution of aniline (11.5 mL, 125 mmol) in methylene chloride (50 mL) and triethylamine (17.5 mL, 127 mmol) and the resultant solution was allowed to attain rt over 24 hr. Water (100 mL) was added and the reaction mixture was stirred vigorously and the aqueous phase removed. This was repeated three times. The organics were washed with brine (100 mL), dried (MgSO$_4$) and concentrated in vacuo to afford the titled product (12.2 g) as a dark solid. During the above extraction a precipitate formed which was removed by filtration to afford a white solid (9.40 g), total yield 21.6 g (78%). Both these products were identical. TLC (20% ethyl acetate in hexane) R$_f$=0.18. $^1$H NMR (300 MHz, CDCl$_3$) d 4.02 (s, 2H), 7.16 (t, J=7.0 Hz, 1H), 7.38 (t, J=6.8 Hz, 2H), 7.52 (d, J=7.0 Hz, 2H), 8.20 (br, 1H).

Intermediate 12 B

Potassium phthalimide (4.119, 22.2 mmol) was added to a solution of Intermediate 12 A (5.009, 22.2 mmol) in DMF (25 mL) and the resultant mixture was stirred at rt for 16 h. The reaction mixture was poured into water (150 mL) and extracted into ethyl acetate (5×80 mL). The combined organics were washed with water (3×100 mL), brine (100 mL), dried (MgSO$_4$) and concentrated in vacuo to afford the titled product (4.61 g, 75%) as a white solid. TLC (10% methanol in methylene chloride) R$_f$=0.71. $^1$H NMR (300 MHz, CDCl$_3$) d 4.58 (s, 2H), 7.16 (m, 1H), 7.38 (m, 2H), 7.51 (d, J=7.0 Hz, 2H), 7.60 (br, 1H), 7.80 (m, 2H), 7.90 (m, 2H).

Intermediate 12 C

Sodium hydride (60% in oil, 142 mg, 3.57 mmol) was added to a 0° C. suspension of Intermediate 12 B (1.00 g, 3.57 mmol) in DMF (10 mL) and the resultant mixture stirred at 0° C. for 30 min prior to the addition of 2-bromo-N-isopropyl-N-phenyl acetamide (893 mg, 5.57 mmol) and the resultant mixture was stirred at rt overnight. The reaction mixture was poured into 2N hydrochloric acid (50 mL) and extracted into ethyl acetate (3×50 mL). The combined organics were washed with water (3×30 mL), brine (30 mL), dried (MgSO$_4$) and concentrated in vacuo to afford the crude product (2.30 g). Recrystalisation from ethyl acetate gave the titled product (1.04 g) as a white solid TLC (20% ethyl acetate in hexane) R$_f$=0.32. This was used crude in next reaction.

Intermediate 12 D

A mixture of Intermediate 12 C (520 mg, 1.14 mmol) and methyl hydrazine (150 mg) in ethanol (20 mL) was stirred at rt for 16 h. The solvents were removed in vacuo and the residue was partitioned between ethyl acetate (20 mL) and 2N hydrochloric acid (2×10 mL). The combined aqueous phase was concentrated in vacuo and the water removed by azeotrope with acetonitrile to afford the titled product as a yellow glass (424 mg, 72%). TLC (10% methanol in methylene chloride) R$_f$=0.53. $^1$H NMR (300 MHz, CDCl$_3$) d 1.03 (d, J=7.0 Hz, 6H), 3.20 (br, 2H), 3.90 (br, 2H), 4.97 (sept, J=7.0 Hz, 1H), 7.10–7.60 (m, 12H).

Intermediate 12E

A solution of m-carboxyethyl phenylisocyanate (40.3 mg) in methylene chloride (1.0 mL) was added to a solution of intermediate 12-D (94.0 mg) in methylene chloride (1.0 mL) and triethylamine (0.1 mL) and the resultant solution was stirred at rt for 72 h. The solvents were removed in vacuo to afford the titled product (134 mg) as a yellow glass. $^1$H NMR (300 MHz, CDCl$_3$) d 1.03 (d, J=7.0 Hz, 6H), 1.38 (t, J=7.0 Hz, 3H), 3.83 (d, J=6.0 Hz, 2H), 3.93 (s, 2H), 4.30 (q, J=7.0 Hz, 2H), 4.97 (sept, J=7.0 Hz, 1H), 6.23 (t, J=3.6.0 Hz, 1H), 7.0–7.60 (m, 14H), 7.96 (s, 1H), 8.22 (s, 1H).

EXAMPLE 12

(R)-3-{3-[(isopropyl-phenyl-carbamoylmethyl)-phenyl-carbamoylmethyl]-ureido}-benzoic acid.

A mixture of intermediate 12 E (134.0 mg), 1N aqueous sodium hydroxide (0.26 mL) and methanol (1.0 mL) was stirred at rt for 40 h. 1N aqueous sodium hydroxide (0.13 mL) and methanol (0.25 mL) were added and the mixture stirred at rt for a further 48 h. The reaction mixture was concentrated in vacuo and the residue partitioned between water (5 mL) and ethyl acetate (2×5 mL). The aqueous phase was acidified to pH 4 (1N hydrochloric acid) and extracted into ethyl acetate (2×20 mL). The resultant precipitate was removed by filtration and RP-HPLC (48% to 64%, 30 min) gave the titled product (17.9 mg) as a white lyophile. (45% to 64%, 30 min) T$_r$=17.61 min. $^1$H NMR (300 MHz, CDCl$_3$) d 1.03 (d, J=7.0 Hz, 6H), 3.83 (br, 2H), 3.93 (br, 2H), 4.97 (sept, J=7.0 Hz, 1H), 7.0–7.60 (m, 14H), 8.26 (s, 1H), 8.40 (s, 1H). C$_{27}$H$_{28}$N$_4$O$_5$ requires m/z 488.5433; found 488.5401

EXAMPLE 13

(R)-N-(Isopropyl-phenyl-carbamoylmethyl)-N-phenyl-2-(3-phenyl-ureido)-acetamide.

A solution of phenyl isocyanate (33.0 mg, 0.277 mmol) in dichloromethane (1.0 mL) was added to a solution of Intermediate 12 D (100 mg, 0.277 mmol) and triethylamine (0.084 mL) in dichloromethane (1.0 mL) and the resultant mixture stirred at rt for 14 h. The solvents were removed in vacuo and the residue triturated with ether to afford the crude product. Flash column chromatography (3% methanol in methylene chloride) followed by RP-HPLC (45% to 64%, 30 min) gave the titled product (38 mg) as a white lyophile. (45% to 64%, 30 min) T$_r$=24.5 min. $^1$H NMR (300 MHz, CDCl$_3$) d 1.03 (d, J=7.0 Hz, 6H), 3.80 (br, 2H), 3.90 (d, J=4.0 Hz, 2H), 3.96 (s, 2H), 4.92 (sept, J=7.0 Hz, 1H), 6.18 (t, J=40 Hz) 6.90–7.60 (m, 15H), 8.0 (s, 1H), 8.60 (s,1H). C$_{26}$H$_{28}$N$_4$O$_3$ requires m/z 444.5335; found 444.5372.

EXAMPLE 14

(R)-3-4-Benzyloxy-phenyl)-N-[isopropyl-4-methoxy-phenyl)-carbamoylmethyl]-N-phenyl-2-(3-phenyl-ureido)-propionamide.

Intermediate 14 A

A solution of aniline (930 mg, 10 mol), BOP (4.29 g), HOBT (1.37 g), DMAP (1.17 g) and N-Boc-O-benzyl-D-tyrosine (3.71 g, 10.00 mmol) in DMF (10 mL) was stirred at rt overnight. The reaction mixture was diluted with ethyl acetate (150 mL) and extracted into 1N aqueous sodium hydroxide solution (2×80 mL), water (100 mL), 0.5N hydrochloric acid (2×100 mL), water (2×100 mL), brine (100 mL), dried (MgSO$_4$) and concentrated in vacuo to afford the titled product (3.74 g) as a cream solid. TLC (10% methanol in methylene chloride) R$_f$=0.43. $^1$H NMR (300 MHz, DMSO-d$_6$) d 1.36 (s, 9H), 2.77 (dd,J=7.0, 8.0 Hz, 1H), 2.90 (dd, J=8.0, 2.1 Hz, 1H), 4.21 (m, 1H), 5.04 (s, 2H), 6.90 (d, J=7 Hz, 2H), 7.04–7.40 (m, 10H), 7.60 (d, J=7 Hz, 2H), 10.03 (s, 1H).

Intermediate 14 B

Sodium hydride (60% in oil, 144 mg 3.44 mmol) was added to a 0° C. solution of Intermediate 14 A (1.53 g 3.44 mmol) in DMF (15 mL) and the resultant mixture stirred at 0° C. for 5 min prior to the addition of 2-bromo-N-isopropyl-N-(4-methoxyphenyl) acetamide (984 mg, 3.44 mmol) and the resultant mixture was stirred at rt overnight. The reaction mixture was diluted with ethyl acetate (80 mL) and extracted into water (3×40 mL), washed with brine (40 mL), dried (MgSO$_4$) and concentrated in vacuo to afford the titled product (2.12 g) as a light brown foam. TLC (10% methanol in methylene chloride) R$_f$=0.18. $^1$H NMR (300 MHz, DMSO-d$_6$) d 0.97 (d, J=6.0 Hz, 6H) 1.32 (s, 9H), 2.87 (m, 2H), 3.78 (s, 3H), 4.03 (dd, J=16.0, 6.0 Hz, 2H) 4.21 (m, 1H), 4.84 (sept, J=6.0 Hz, 1H), 4.97 (s, 2H, obscures m, 1H) 6.52 (d, J=9.0 Hz, 2H), 6.72 (d, J=9.0 Hz, 2H), 7.0–7.50 (m, 15H).

Intermediate 14 C

A mixture of Intermediate 14 B (2.12 g, 3.44 mmol) and 4N HCl in dioxane (20 mL) was stirred at rt for 2 h. Diethyl ether (80 mL) was added and the solvent was removed from the resultant precipitate by decanting. The residue was triturated with diethyl ether (3×80 mL) to afford the crude product (1.21 g) as a cream powdery solid. TLC (10% methanol in methylene chloride) R$_f$=0.21. $^1$H NMR (300 MHz, DMSO-$_6$) d 0.97 (d, J=6.0 Hz, 6H), 2.77 (m, 1H), 2.91 (m, 1H) 3.82 (s, 3H, obscures another peak, 1H), 4.81 (sept, J=6.0 Hz, 1H), 5.07 (s, 2H), 6.62 (d, J=9.0 Hz, 2H), 6.82 (d, J=9.0 Hz, 2H), 7.0–7.50 (m, 15H), 8.40 (br, 3H).

EXAMPLE 14

(R)-3-(4-Benzyloxy-phenyl)-N-[isopropyl-(4-methoxy-phenyl)-carbamoylmethyl]-N-phenyl-2-(3-phenyl-ureido)-propionamide.

A solution of phenyl isocyanate (112 mg) in dichloromethane (1.0 mL) was added to a solution of Intermediate 14 C (500 mg) and triethylamine (0.3 mL) in dichloromethane (4.0 mL) and the resultant mixture stirred at rt for 3 h. The solvents were removed in vacuo and the residue partitioned between ethyl acetate (30 mL) and 1N hydrochloric acid (20 mL). The organics were washed with water (3×20 mL), brine (20 mL), dried (MgSO$_4$) and concentrated in vacuo to afford the crude product (500 mg) as a straw glassy foam. TLC (3% methanol in methylene chloride) R$_f$=0.47. $^1$H NMR (300 MHz, CDCl$_3$) d 0.97 (2×d, J=7.0 Hz, 6H), 2.77 (dd, J=14, 8.5 Hz, 1H), 3.03 (dd, J=14, 5.3 Hz, 1H)

3.62 (s, 3H), 3.64 (d, J=16.8 Hz, 1H), 4.14 (d, J=16.8 Hz, 1H) 4.90 (m, 2H), 5.01 (s, 2H), 6.42 (d, J=9.0 Hz, 2H), 6.59 (d, J=9.0 Hz, 2H), 7.0–7.50 (m, 21H). $C_{41}H_{42}N_4O_5$ requires m/z 670.8089 found 670.8111.

EXAMPLE 15

(R)-3-(4-Hydroxy-phenyl)-N-[isopropyl-(4-methoxy-phenyl)-carbamoylmethyl]-N-phenyl-2-(3-phenyl-ureido)-propionamide.

A mixture of Example 14 (475 mg, 0.723 mmol) and 10% Pd/C (50 mg) in ethanol (30 mL) was stirred under an atmosphere of hydrogen for 2 h after which time a further batch of catalyst (50 mg) was added. After 6 h the solids were removed by filtration through celite to afford the crude titled product as a white foam (380 mg). TLC (3% methanol in methylene chloride) $R_f$=0.23. $^1$H NMR (300 MHz, CDCl$_3$) d 0.97 (2xd, J=7.0 Hz, 6H), 2.62 (dd, J=13.0, 6.2 Hz, 1H), 2.97 (dd, J=13.0, 4.1 Hz, 1H), 3.64 (s, 3H), 3.70 (d, J=16.6.0 Hz, 1H), 4.19 (d, J=16.6.0 Hz, 1H) 4.90 (m, 2H), 6.38 (d, J=9.0 Hz, 1H), 6.6–7.6 (m, 20H). $C_{34}H_{36}N_4O_5$ requires m/z 580.6838; found 580.6852.

EXAMPLE 16

(R)-1H-Indole-2-carboxylic acid (2-(4-hydroxy-phenyl)-1-{[(isopropyl-(4-methoxy-phenyl)-carbamoylmethyl]-phenyl-carbamoyl}-ethyl)-amide.

Intermediate 16 A

A solution of Intermediate 14 C (500 mg, 0.89 mmol), BOP (0.38 g), HOBT (122 mg), DMAP (104 mg) and indole-2-carboxylic acid (150 mg, 0.89 mmol) in DMF (1 mL) and triethylamine (0.3 mL) was stirred at rt overnight. The reaction mixture was diluted with ethyl acetate (150 mL) and extracted into 1N aqueous sodium hydroxide solution (2×80 mL), water (100 mL), 0.5N hydrochloric acid (2×100 mL), water (2×100 mL), brine (100 mL), dried (MgSO$_4$) and concentrated in vacuo to afford the titled product (555 mg) as a white glass. TLC (10% methanol in methylene chloride) $R_f$=0.81. $^1$H NMR (300 MHz, CDCl$_3$) d 1.07 (2xd, J=7.0 Hz, 6H), 2.82 (dd, J=13.1, 6.6.0 Hz, 1H), 3.03 (dd, J=13.1, 4.2 Hz, 1H), 3.78 (d, J=17.1 Hz, 1H), 3.82 (s, 3H), 4.14 (d, J=17.1 Hz, 1H), 4.96 (s, 2H), 5.02 (m, 2H), 6.8–7.50 (m, 23H), 7.62 (d, J=7.0 Hz, 1H), 9.22 (s, 1H).

EXAMPLE 16

(R)-1H-lndole-2-carboxylic acid (2-(4-hydroxy-phenyl)-1-{[(isopropyl-(4-methoxy-phenyl)-carbamoylmethyl]-phenyl-carbamoyl}-ethyl)-amide.

A mixture of Intermediate 16 A (475 mg, 0.723 mmol) and 10% Pd/C (50 mg) in ethanol (30 mL) was stirred under an atmosphere of hydrogen for 20 h after which time a further batch of catalyst (50 mg) was added. After a further 6 h the solids were removed by filtration through celite to afford the crude titled product as a white foam (470 mg). Flash column chromatography (3% methanol in methylene chloride) gave the titled product (204 mg) as a white solid which was further purified by RP-HPLC (48% to 64%, 30 min) to give the titled product (182 mg) as a white lyophile. (45% to 64%, 30 min) T$_r$=25.81 min. $^1$H NMR (300 MHz, CDCl$_3$) d 1.07 (2xd, J=7.0 Hz, 6H), 2.82 (dd, J=13.1, 6.6.0 Hz, 1H), 3.03 (dd, J=13.1, 4.2 Hz, 1H), 3.79 (d, J=16.6.0 Hz, 1H) 3.82 (s, 3H), 4.20 (d, J=16.6.0 Hz, 1H), 4.97 (sept, J=7.0 Hz, 1H), 5.12 (m, 1H), 6.57 (d, J=9.0 Hz, 3H), 6.82 (d, J=8.0 Hz, 2H) 6.90–7.40 (m, 14H), 7.62 (d, J=7.0 Hz, 1H), 9.32 (s, 1H). $C_{36}H_{36}N_4O_5$ requires m/z 604.7058 found 604.7102.

EXAMPLE 17

(R)-3-Hydroxy-N-[isopropyl-(4-methoxy-phenyl)-carbamoylmethyl]-N-phenyl-2-(3-phenyl-ureido)-propionamide.

Intermediate 17 A

A solution of aniline (930 mg, 10 mol), BOP (4.29 g), HOBT (1.37 g), DMAP (1.17 g) and N-Boc-O-benzyl-D-serine (2.95 g, 10.00 mmol) in DMF (10 mL) was stirred at rt overnight. The reaction mixture was diluted with ethyl acetate (150 mL) and extracted into 1N aqueous sodium hydroxide solution (2×80 mL), water (100 mL), 0.5N hydrochloric acid (2×100 mL), water (2×100 mL), brine (100 mL), dried (MgSO$_4$) and concentrated in vacuo to afford the titled product (2.80 g) as a yellow glass. TLC (30% ethyl acetate in hexane) $R_f$=0.43. $^1$H NMR (300 MHz, DMSO-d$_6$) d 1.36 (s, 9H), 3.66 (m, 2H), 4.39 (m, 1H), 4.52 (s, 2H), 7.02 (m, 2H), 7.27 (m, 5H), 7.60 (m, 2H), 10.03 (s, 1H).

Intermediate 17 B

Sodium hydride (60% in oil, 144 mg, 3.44 mmol ) was added to a 0° C. solution of Intermediate 17 A (1.27 g, 3.44) in DMF (15 mL) and the resultant mixture stirred at 0° C. for 5 min prior to the addition of 2-bromo-N-isopropyl-N-(4-methoxyphenyl) acetamide (984 mg) and the resultant mixture was stirred at rt overnight. The reaction mixture was diluted with ethyl acetate (50 mL) and extracted into water (3×20 mL), washed with brine (20 mL), dried (MgSO$_4$) and concentrated in vacuo to afford the titled product (1.82 g) as a colorless light brown foam. Flash column chromatography (30% ethyl acetate in hexane) gave the titled product (840 mg, 44%) as a colorless foam. TLC (30% ethyl acetate/hexane) $R_f$=0.21. $^1$H NMR (300 MHz, DMSO-d$_6$) d 1.04 (2xd, J=7.0 Hz, 6H), 1.42 (s, 9H), 3.39 (dd, J=8.0, 3.0 Hz, 1H), 3.57 (dd, J=8, 1.5 Hz, 1H), 3.82 (s, 3H), 3.92 (dd, J=22.0, 10.0 Hz, 2H), 4.39 (dd, J=22.0, 8.0 Hz, 2H) 4.62 (m, 1H), 4.97 (sept, J=7.0 Hz, 1H), 6.40 (m, 1H), 6.90 (d, J=7.0 Hz, 2H) 7.04 (d, J=7.0 Hz, 2H), 7.2–7.40 (m, 10H).

Intermediate 17 C

A mixture of Intermediate 17 B (840 mg) and 4N HCl in dioxane (10 mL) was stirred at rt for 2 h. Diethyl ether (80 mL) was added and the solvent was removed from the resultant precipitate by decanting. The residue was triturated with diethyl ether (3×80 mL) to afford the crude product (610 mg) as a colorless foam. TLC (10% methanol in methylene chloride) $R_f$=0.24. $^1$H NMR (300 MHz, DMSO-d$_6$) d 0.935 (2xd, J=7.0 Hz, 6H), 3.39 (dd, J=10.4, 3.1 Hz, 1H), 3.77 (s, 3H), 3.87 (d, J=7.0 Hz, 1H), 3.92 (dd, J=22.0, 10.0 Hz, 2H), 4.01 (br, 1H), 4.23 (d, J=11.2 Hz, 1H), 4.32 (d, J=11.2 Hz, 1H), 4.74 (sept, J=7.0 Hz, 1H), 6.90–7.51 (m, 14H), 8.40 (br, 3H).

Intermediate 17 D

A solution of phenyl isocyanate (73 mg, 0.586 mmol) in dichloromethane (1.0 mL) was added to a solution of Intermediate 17 C (300 mg, 0.586 mmol) and triethylamine (0.197 mL) in dichloromethane (3.0 mL) and the resultant mixture stirred at rt for 3 h. The solvents were removed in vacuo and the residue partitioned between ethyl acetate (30 mL) and 1N hydrochloric acid (20 mL). The organics were washed with water (3×20 mL), brine (20 mL), dried (MgSO$_4$) and concentrated in vacuo to afford the crude product (303 mg) as a cream foam. TLC (10% methanol in methylene chloride) $R_f$=0.80. $^1$H NMR (300 MHz, CDCl$_3$) d 0.935 (d, J=7.0 Hz, 6H), 3.66 (d, J=6.1 Hz, 2H), 3.68 (s, 3H), 3.81 (d, J=14.0 Hz, 1H), 4.05 (d, J=13.8 Hz, 1H), 4.23 (d, J=12.2 Hz, 1H), 4.32 (d, J=12.2 Hz, 1H), 4.74 (sept, J=7.0 Hz, occludes peak, 2H), 6.58 (d, J=7.8 Hz, 1H), 6.63 (dd, J=8.8, 3.0 Hz, 1H), 6.73 (dd, J=8.6, 2.7 Hz, 1H), 6.90–7.51 (m, 16H), 7.8 (s, 1H).

EXAMPLE 17

(R)-3-Hydroxy-N-[isopropyl-4-methoxy-phenyl)-carbamoylmethyl]-N-phenyl-2-(3-phenyl-ureido)-propionamide.

A mixture of Intermediate 17 D (300 mg, 0.505 mmol) and 10% Pd/C (60 mg) in ethanol (30 mL) was stirred under an atmosphere of hydrogen for 20 h after which time a further batch of catalyst (50 mg) was added. After a further 6 h the solids were removed by filtration through celite to afford the crude titled product as a white foam (203 mg). Flash column chromatography (3% methanol in methylene chloride) gave the titled product (174 mg) as a white solid which was further purified by RP-HPLC (48% to 64%, 30 min) to give the titled product (153 mg) as a white lyophile. (45% to 64%, 30 min) $T_r$=15.53 min. $^1$H NMR (300 MHz, CDCl$_3$) d 0.995 (d, J=7.0 Hz, 6H), 3.48 (d, J=16.6.0 Hz, 1H), 3.62 (d, J=9.5 Hz, 1H), 3.73 (s, 3H), 3.83 (m, 1H), 4.50 (d, J=16.6.0 Hz, 1H), 4.91 (sept, J=7.0 Hz, occludes peak, 2H), 6.63 (dd, J=8.8, 3.0 Hz, 1H), 6.90–7.51 (m, 13H), 7.93 (s, 1H). $C_{28}H_{32}N_4O_5$ requires m/z 504.5860; found 504.5863

(R)-1H-Indole-2-carboxylic acid (2-hydroxy-1-{[(isopropyl-4-methoxy-phenyl)-carbamoylmethyl]-phenyl-carbamoyl}-ethyl)-amide.

Intermediate 18 A

A solution of Intermediate 17 C (310 mg, 0.591 mmol), BOP (0.252 g), HOBT (82 mg), DMAP (70 mg) and indole-2-carboxylic acid (99.6 mg, 0.591 mmol) in DMF (1 mL) and triethylamine (0.3 mL) was stirred at rt overnight. The reaction mixture was diluted with ethyl acetate (150 mL) and extracted into 1N aqueous sodium hydroxide solution (2×80 mL), water (100 mL), 0.5N hydrochloric acid (2×100 mL), water (2×100 mL), brine (100 mL), dried (MgSO$_4$) and concentrated in vacuo to afford the titled product (350 mg) as a cream foam. TLC (3% methanol in methylene chloride) $R_f$=0.51. $^1$H NMR (300 MHz, CDCl$_3$) d 1.02 (2×d, J=7.0 Hz, 6H), 3.54 (dd, J=10.2, 6.1 Hz, 1H), 3.68 (dd, J=10.5, 4.6.0 Hz, 1H), 3.82 (s, 3H), 4.00 (ABq, J=34.2, 16.2 Hz, 2H), 4.00 (ABq, J=37.6, 12.2 Hz, 2H), 4.74 (sept, J=7.0 Hz), 5.1 (br, 1H), 6.90–7.41 (m, 17H), 7.64 (d, J=7.8 Hz, 1H), 9.27 (s, 1H).

EXAMPLE 18

(R)-1H-lndole-2-carboxylic acid (2-hydroxy-1-{[(isopropyl-(4-methoxy-phenyl)-carbamoylmethyl]-phenyl-carbamoyl}-ethyl)-amide.

A mixture of Intermediate 18 A (350 mg, 0.566 mmol) and 10% Pd/C (80 mg) in ethanol (30 mL) was stirred under an atmosphere of hydrogen for 20 h after which time a further batch of catalyst (50 mg) was added. After a further 6 h the solids were removed by filtration through celite to afford the crude titled product as a white foam (287 mg). TLC (3% methanol in methylene chloride) $R_f$=0.28. RP-HPLC (48% to 64%, 30 min) gave the titled product (238 mg) as a white lyophile. (45% to 64%, 30 min) $T_r$=12.65 min. $^1$H NMR (300 MHz, CDCl$_3$) d 1.07 (d, J=6.8 Hz, 6H), 3.48 (d, J=16.8 Hz, 1H), 3.51 (dd, J=9.5, 4.2 Hz, 1H), 3.73 (s, 3H, occludes dd, 1H), 4.61 (d, J=16.8 Hz, 1H), 4.91 (sept, J=7.0 Hz, 1H), 5.1 (br, 1H), 6.90–7.41 (m, 12H), 7.65 (d, J=8.0 Hz, 1H), 9.24 (s, 1H). $C_{30}H_{32}N_4O_5$ requires m/z 528.6080; found 528.6111

EXAMPLE 19

(S)-4-{[Isopropyl-(4-methoxy-phenyl)-carbamoylmethyl]-phenyl-carbamoyl}-4-(3-phenyl-ureido)-butyric acid.

Intermediate 19 A

A solution of aniline (613 mg, 6.59 mmol), BOP (2.83 g), HOBT (902 mg), DMAP (773 mg) and N-Boc-L-glutamic acid gamma tert-butyl ester (2.00 g, 6.59 mmol) in DMF (5 mL) was stirred at rt overnight. The reaction mixture was diluted with ethyl acetate (150 mL) and extracted into 1N aqueous sodium hydroxide solution (2×80 mL), water (100 mL), 0.5N hydrochloric acid (2×100 mL), water (2×100 mL), brine (100 mL), dried (MgSO$_4$) and concentrated in vacuo to afford the titled product (2.16 g) as a colorless glass. $^1$H NMR (300 MHz, CDCl$_3$) d 1.4 (s, 18H), 1.95 (m, 1H), 2.12 (m, 1H), 2.37(m, 1H), 2.51 (m, 1H), 4.22 (br, 1H), 5.40 (d, J=6.0 Hz, 1H), 7.09 (t, J=7.0 Hz, 1H), 7.29 (t, J=7.0 Hz, 2H), 7.50 (d, J=7.0 Hz, 2H), 8.55 (s, 1H).

Intermediate 19-B

Sodium hydride (60% in oil, 74.5 mg, 1.78 mmol) was added to a 0° C. solution of Intermediate 19 A (673 mg, 1.78 mmol) in DMF (5 mL) and the resultant mixture stirred at 0° C. for 4 min prior to the addition of 2-bromo-N-isopropyl-N-(4-methoxyphenyl) acetamide (509 mg, 1.78 mmol) and the resultant mixture was stirred at rt overnight. The reaction mixture was diluted with ethyl acetate (50 mL) and extracted into water (3×20 mL), washed with brine (20 mL), dried (MgSO$_4$) and concentrated in vacuo to afford the crude product. Purification by flash column chromatography (20% ethyl acetate in hexane) gave the titled product (370 mg) as a colorless foam. TLC (20% ethyl acetate/hexane) $R_f$=0.22. H NMR (300 MHz, CDCl$_3$) d 0.87 (2×d, J=7.0 Hz, 6H), 1.22 (2×s, 18H), 1.58 (m, 1H), 1.72 (m, 1H), 1.97 (m, 2H), 3.60 (d, J=16.0 Hz, 1H), 3.68 (s, 3H), 3.95 (d, J=16.0 Hz, 1H), 4.21 (br, 1H), 4.80 (sept, J=6.0 Hz, 1H), 5.12 (d, J=5.0 Hz, 1H), 7.0–7.5 (m, 9 H).

Intermediate 19-C

A mixture of intermediate 19-B (370 mg, 0.63 mmol) and 4N HCl in dioxane (4 mL) was stirred at rt for 3 h. Diethyl ether (80 mL) was added and the solvent was removed from the resultant precipitate by decanting. The residue was triturated with diethyl ether (3×80 mL) to afford the crude product (220 mg, 76%) as a white powder. $^1$H NMR (300 MHz, DMSO-d$_6$) d 0.90 (2×d, J=7.0 Hz, 6H), 1.58 (m, 1H), 1.70(m, 1H), 2.18 (m, 2H), 3.64 (d, J=16.6.0 Hz, 1H), 3.70 (s, 3H), 3.82 (br, 1H), 3.95 (d, J=16.6 Hz, 1H), 4.70 (sept, J=6.0 Hz, 1H), 6.9–7.5 (m, 11H).

EXAMPLE 19

(S)4-{[Isopropyl-(4-methoxy-phenyl)-carbamoylmethyl]-phenyl-carbamoyl}-4-(3-phenyl-ureido)-butyric acid.

A solution of phenyl isocyanate (59.0 mg, 0.475 mmol) in dichloromethane (3.0 mL) was added to a solution of Intermediate 19 C (220 mg, 0.475 mmol) and triethylamine (0.163 mL) in dichloromethane (0.5 mL) and the resultant mixture stirred at rt for 3 days. The solvents were removed in vacuo and the residue partitioned between ethyl acetate (30 mL) and 1N hydrochloric acid (20 mL). The organics were washed with water (3×20 mL), brine (20 mL), dried (MgSO$_4$) and concentrated in vacuo to afford the crude product (248 mg) as a colorless glassy foam. RP-HPLC (45% to 64%, 30 min) gave the titled product (103 mg) as a white lyophile. (45% to 64%, 30 min) $T_r$=16.32 min (co-elutes with Example GH-1). $^1$H NMR (300 MHz, CDCl₃) d 0.82 (2×d, J=7.0 Hz, 6H), 1.82 (m, 1H), 1.98 (m, 2H), 2.24 (m, 1H), 3.29 (d, J=16.0 Hz, 1H), 3.52 (s, 3H), 4.20 (d, J=16.0 Hz, 1H), 4.54 (m, 1H), 4.95 (sept, J=6.0 Hz, 1H), 6.25 (d, J=7.0 Hz, 1H), 6.62 (m, 2H), 6.85–7.40 (m, 11H), 8.20 (br, 1H). $C_{30}H_{34}N_4O_6$ requires m/z 546.6233 found 540.6258

EXAMPLE 20

(R)4-[(Isopropyl-phenyl-carbamoylmethyl)-phenyl-carbamoyl]-4-(3-phenyl-ureido)-butyric acid methyl ester.

A solution of diazomethane in diethyl ether (generated from N-methyinitroso urea, 623 mg and 40% aqueous potassium hydroxide, 2 mL) was added dropwise to a solution of Example 4 (11.2 mg, 0.0217 mmol) in tetrahydrofuran (2 mL) until a yellow color persisted. Acetic acid was added until yellow color disappeard and the solvents were removed in vacuo. RP-HPLC (45% to 64%, 30 min) gave the titled product (10.3 mg) as a white iyophile. (45% to 64%, 30 min) $T_r$=13.07 min. ¹H NMR (300 MHz, CDCl₃) d 1.0 (2×d, J=7.0 Hz, 6H), 1.90 (m, 1H), 2.07 (m, 1H), 2.20 (m, 1H), 2.41 (m, 1H), 3.40 (d, J=16.6 Hz, 1H), 4.21 (s, 3H), 4.36 (d, J=16.6.0 Hz, 1H), 4.70 (m, 1H), 5.20 (sept, J=6.0 Hz, 1H), 6.57 (d, J=7.0 Hz, 1H), 6.88 (m, 4H), 7.10 (m, 4H), 7.21 (br, 2H), 7.38 (m, 4H), 7.59 (d, J=7.0 Hz, 2H), 8.30 (s, 1H). $C_{31}H_{36}N_4O_6$ requires m/z 560.6502; found 560.6541.

EXAMPLE 21

N-Isopropyl-2-(5-methyl-2-oxo-2,3,4,5-tetrahydro-benzo[e][1,4]diazepin-1-yl)-N-phenyl-acetamide.

Intermediate 21 A

To 2-(3-amino-5-methyl-2-oxo-2,3-dihydro-benzo[e][1,4]diazepin-1-yl)-N-isopropyl-N-phenyl acetamide benzyl carbamate (783 mg, 1.60 mmol) in methanol (16 mL) was added 10% palladium on carbon (320 mg). The resulting mixture was stirred under a hydrogen atmosphere for 15 h. The solids were removed by filtration through a pad of celite. The celite pad was washed with methanol and the filtrate concentrated in vacuo to give the titled compound (611 mg, 100%). $R_f$=0.04 (2/3 ethyl acetate/hexane); ¹HNMR (300 MHz, CD₃OD) d 1.06 (d, J=6.9 Hz, 3H), 1.08 (d, J=6.9 Hz, 3H), 1.47 (d, J=6.3 Hz, 3H), 3.18 (s, 2H), 4.07 (d, J=16.6 Hz, 1H), 4.20 (d, J=16.6 Hz, 1H), 4.43 (m, 1H), 7.21 (m, 1H), 7.34 (m, 6H), 7.51 (m, 3H).

EXAMPLE 21

N-Isopropyl-2-(5-methyl-2-oxo-2,3,4,5-tetrahydro-benzo[e][1,4]diazepin-1-yl)-N-phenyl-acetamide.

To intermediate 21 A (200 mg, 0.57 mmol) in DCM (2 mL) was added phenyl isocyanate (68 mL, 1.36 mmol). The reaction mixture was stirred at rt for 12 h, was concentrated to dryness and purified by RP-HPLC (42–60%, over 30 min) to give the titled compound (90 mg, 33%). $t_R$=16.11 (42–60%, over 30 min.); ¹HNMR (300 MHz, CDCl₃) d 1.12 (d, J=6.8 Hz, 6H), 1.30 (d, J=6.8 Hz, 3H), 3.60 (d, J=16.6 Hz, 1H), 3.80 (d, J=13.1 Hz, 1H), 4.28 (d, J=13.1 Hz, 1H), 4.48 (d, J=16.6 Hz, 1H), 5.05 (m, 1H), 5.32 (m, 1H), 6.81 (s, 1H), 7.04 (m, 1H), 7.40 (bm, 14H); MS(FAB) m/z 471.1 (MH⁺).

EXAMPLE 22

N-Isopropyl-2-[4-oxo-3-(3-phenyl-ureido)-3,4-dihydro-2H-benzo[b][1,4]thiazepin-5-I]-N-phenyl-acetamide.

Intermediate 22 A O12356-8(31)

To N-BOC-D-cysteine (6.08 g, 27.5 mmol) in ethanol (18 mL) and water (53 mL) was added 1-fluro-2-nitrobenzene (2.36 mL, 22.37 mmol) and sodium bicarbonate (5.64 g, 67.1 mmol). The reaction mixture was heated at reflux for 3 h, cooled to rt, concentrated in vacuo, and acidified to pH2 with sodium bisulfate. The aqueous layer was extracted with Et₂O, dried (MgSO₄) and concentrated to give crude product (7.34 g, 96%). $R_f$=0.44 (10% methanol/DCM, 0.5% HOAc); ¹HNMR (300 MHz, CDCl₃) d 1.42 (s, 9H), 3.35 (m, 1H), 3.56 (m, 1H), 4.60 (m, 1H), 5.38 (d, J=7.1 Hz, 1H), 7.29 (m, 1H), 7.57 (m, 2H), 8.15 (m, 1H), 10.15 (bs, 1H); MS(FAB) m/z 343 (MH⁺).

Intermediate 22 B

To intermediate 22 A (7.19 g, 21.02 mmol) was added 4N aqueous HCl in dioxane (10 mL). The reaction mixture was stirred for 1.5 h at rt, Et₂O (150 mL) was added and the resultant preciptate collected by filtration, washed with Et₂O (2×20 mL) to give the crude amine (7.67 g, 100%). $R_f$=0.04 (10% methanol/DCM); MS(FAB) m/z 243.0 (MH⁺).

Intermediate 22 C

To intermediate 22 B (7.67 g, 31.7 mmol) in THF (35 mL) and water (80 mL) was slowly added sodium bicarbonate (2.4 g, 42 mmol) followed by benzoxycarbonyl-N-hydroxy succinimide (5.24 9, 21.02 mmol). The reaction mixture was stirred at rt for 24 h, was acidified to pH1 with 6N aqueous HCl, and extracted with ethyl acetate (5×30 mL). The combined extracts were washed with brine, dried (MgSO₄), and concentrated to give the crude product (8.01 g, 100%). $R_f$=0.27 (10% methanol/DCM); ¹HNMR (300 MHz, d6-DMSO) d 3.20 (m, 1H), 3.53 (m, 1H), 4.18 (m, 1H), 4.99 (s, 2H), 7.32 (m, 6H), 7.68 (m, 2H), 7.80 (d, J=7.6 Hz, 1H), 8.16 (d, J=7.6 Hz, 1H); MS (FAB) m/z 377.0 (MH⁺).

Intermediate 22 D

To intermediate 22 C (8.01 g, 21.3 mmol) in methanol (420 mL) was added zinc (19.2 g) and ammonium chloride (2.26 g, 42.17 mmol) in a three neck flask equipped with an overhead stirrer. The reaction mixture was heated at reflux for 6 h and then was stirred at rt for 12 h. The solids were removed by filtration through a pad of celite, the pad was washed with hot methanol (100 mL) and the filtrate was concentrated to dryness. The residue was dissolved in 1N aqueous HCl (210 mL) and was stirred for 1.5 h. This mixture was cooled to 0° C., basified to pH5 with sodim acetate and the precipitate isolated by filtration. The precipitate was washed with water (2×125 mL) to give after drying the crude product (2.47 g, 34%). ¹HNMR (300 MHz, d6-DMSO) d 2.85 (m, 1H), 3.1(m, 1H), 3.93 (m, 1H), 5.00 (s, 2H), 6.46 (t, J=7.3 Hz, 1H), 6.68 (d, J=8.0 Hz, 1H), 7.01 (t, J=7.3 Hz, 1H), 7.20 (d, J=8.0 Hz, 1H), 7.34 (m, 5H), 7.52 (bd, J=8.0 Hz, 1H); MS(FAB) m/z 347.1 (MH⁺).

Intermediate 22 E

To intermediate 22 D (2.47 g, 7.1 mmol) in DMF (14 mL) was added HOBT (1.35 g, 10 mmol) and EDC (1.36 g, 7.1 mmol). The reaction mixture was stirred at rt for 12 h, diluted with ethyl acetate (300 mL), washed with saturated aqueous NaHCO₃ (1×100 mL), water (4×100 mL), brine (1×100 mL), dried (MgSO₄) and concentrated to give the crude product (2.1 g, 90%). Rf=0.24 (66% EtOAc/hexane); ¹HNMR (300 MHz, CDCl₃) d 2.98 (m, 1H), 3.85 (m, 1H), 4.50 (m, 1H), 5.07 (s, 2H), 5.85 (bs, 1H), 7.12 (d, J=7.7 Hz, 1H), 7.34 (m, 7H), 7.64 (d, J=7.7 Hz, 1H), 7.75 (bs, 1H); MS (FAB) 329.1 (MH⁺).

Intermediate-22 F

To intermediate 22 E (2.1 g, 6.4 mmol) in DMF (50 mL) cooled to 0° C. was added a 60% oil dispersion of sodium hydride (460 mg, 6.4 mmol). The reaction mixture was stirred at 0° C. for 30 min, 2-bromo-N-isopropyl-N-phenyl acetamide (1.64 g, 6.4 mmol) was added and the reaction mixture was allowed to warm to rt. After stirring for 2.5 h, 1N aqueous HCl (100 mL) was added and the reaction mixture was extracted with EtOAc (4×50 mL). The combined extracts were washed with water (1×50 mL), brine (1×50 mL), dried (MgSO$_4$) and concentrated to give the crude product (3.07 g, 95%). $t_R$=32.5 min (42–60% over 30 min); R$_f$=0.30 (66% EtOAc/hexane); $^1$HNMR (300 MHz, d6-DMSO) d 0.97 (d, J=6.7 Hz, 3H), 1.00 (d, J=6.7 Hz, 3H), 2.93 (m, 1H), 3.65 (d, J=16.5 Hz, 1H), 4.19 (m, 1H), 4.25 (d, J=16.5 Hz, 1H), 4.81 (m, 1H), 4.94 (s, 2H), 7.31 (m, 7H), 7.51 (m, 7H), 7.71 (d, J=8.7 Hz, 1H); MS(FAB) m/z 503.9 (MH$^+$).

Intermediate 22 G

To intermediate 22 F (3.07 g, 6.1 mmol) was added to a methanol solution (6 mL) of ammonium formate (1.06 g, 17 mmol) and 10% palladium on carbon (2 g). The reaction mixture was stirred at rt for 12 h. The solids were removed by filtration through a pad of celite, the pad was washed with methanol (2×10 mL) and the filtrate was concentrated. The residue was dissolved in EtOAc (100 mL), washed with saturated sodium bicarbonate (1×30 mL), brine (1×30 mL), dried (MgSO$_4$) and concentrated to give the crude product (1.7 g). The crude product was purified by RP-HPLC (42–60% over 30 min.) to give (1.32 g 58%) of the titled product. $t_R$=9.5 min (42–60%, over 30 min.); $^1$HNMR (300 MHz, d6-DMSO) d 1.00 (d, J=6.7 Hz, 3H), 1.02 (d, J=6.7 Hz, 3H), 3.08 (m, 1H), 3.65 (d, J=16.2 Hz, 1H), 3.75 (m, 1H), 3.95 (m, 1H), 4.25 (d, J=16.2 Hz, 1H), 4.85 (m, 1H), 7.00 (m, 2H), 7.17 (m, 2H), 7.33 (m, 3H), 7.47 (m, 2H), 8.40 (bs, 2H); MS(FAB) m/z 370.0 (MH$^+$).

EXAMPLE 22

N-Isopropyl-2-[4-oxo-3-(3-phenyl-ureido)-3,4-dihydro-2H-benzo[b][1,4]thiazepin-5-I]-N-phenyl-acetamide.

To intermediate 22 G (500 mg, 1.36 mmol) in DCM (5 mL) was added TEA (0.40 mL, 2.72 mmol) and phenyl isocyanate (0.16 mL, 1.36 mmol). The reaction mixture was stirred at rt for 12 h, was concentrated to dryness and purified by RP-HPLC (40–60%, over 30 min) to give the titled compound (221 mg, 33%). $t_R$=9.2 min; $^1$HNMR (300 MHz, acetone) d 1.08 (d, J=6.6 Hz, 3H), 1.10 (d, J=6.6 Hz, 3H), 3.63 (d, J=16.4 Hz, 1H), 3.75 (dd, J=6.6, 11.2, 1H), 4.55 (d, J=16.4 Hz, 1H), 4.61 (m, 1H), 4.97 (m, 1H), 6.26 (d, J=7.1 Hz, 1H), 6.91 (t, J=7.6 Hz, 1H), 7.20 (t, J=7.6 Hz, 1H), 7.45 (bm, 12H), 8.25 (s, 1H); MS(FAB) m/z 489.0 (MH$^+$).

EXAMPLES 23 and 24

The sulfoxides of N-Isopropyl-2-[4-oxo-3-(3-phenyl-ureido)-3,4-dihydro-2H-benzo[b][1,4]thiazepin-5-I]-N-phenyl-acetamide To example 22 (80 mg, 0.16 mmol) in methanol (5 mL) and water (1 mL) was added sodium periodate (35 mg, 0.16 mmol). The reaction mixture was stirred for 12 h, was concentrated to dryness and purified by RP-HPLC (42–60%, over 30 min) to give the titled compounds, isomer 1 (22 mg, 27%) and isomer 2 (14 mg, 17%). Isomer 1: $t_R$=23.31 (42–60%, over 30 min); $^1$HNMR (300 MHz, d6-DMSO) d 0.99 (d, J=6.8 Hz, 3H), 1.03 (d, J=6.8 Hz, 3H), 3.34 (m, 1H), 3.53 (d, J=16.5 Hz, 1H), 3.90 (m, 1H), 4.25 (d, J=16.5 Hz, 1H), 4.58 (m, 1H), 4.88 (m, 1H), 6.79 (d, J=7.4 Hz, 1H), 6.88 (d, J=7.4 Hz, 1H), 7.21 (t, J=7.4 Hz, 2H), 7.30 (m, 3H), 7.45 (m, 3H), 7.68 (m, 2H), 8.87 (s, 1H); MS(FAB) m/z 505.2 (MH$^+$). Isomer 2: $t_R$=25.22 min (42–60%, over 30 min); $^1$HNMR (300 MHz, d6-DMSO) d 0.95 (d, J=7.1 Hz, 3H), 0.98 (d, J=7.1 Hz, 3H), 3.23 (m, 1H), 3.97 (dd, J=10.7, 11.1 Hz, 1H), 4.76 (s, 2H), 4.35 (m, 1H), 4.78 (m, 1H), 6.67 (d, J=7.7 Hz, 1H), 6.87 (d, J=7.3 Hz, 1H), 7.17 (m, 2H), 7.30 (m, 3H) 7.51 (m, 3H), 7.66 (m, 2H), 8.85 (s, 1H); MS(FAB) m/z 505.2 (MH$^+$).

EXAMPLE 25

The sulfone of N-Isopropyl-2-[4-oxo-3-(3-phenyl-ureido)-3,4-dihydro-2H-benzo[b][1,4]thiazepin-5-I]-N-phenyl-acetamide.

To example 22 (80 mg, 0.16 mmol) in DCM (5 mL) was added mCPBA (57 mg, 0.33 mmol). The reaction mixture was stirred at rt for 48 h, was concentrated to dryness and purified by RP-HPLC (42–60%, over 30 min) to give the titled compound (50.3 mg, 59%). $t_R$=29.0 min (42–60%, over 30 min); $^1$HNMR (300 MHz, d6-DMSO) d 0.99 (d, J=6.9 Hz, 3H), 1.03 (d, J=6.9 Hz, 3H), 3.67 (d, J=16.4 Hz, 1H), 3.75 (dd, J=7.0, 11.1 Hz, 1H), 3.97 (dd, J=7.0, 13.3 Hz, 1H), 4.21 (d, J=16.4 Hz, 1H), 4.56 (m, 1H), 4.85 (m, 1H), 6.76 (d, J=7.6 Hz, 1H), 6.90 (dd, J=0.8, 7.3 Hz, 1H), 7.21 (t, J=7.4 Hz, 2H), 7.32 (m, 3H), 7.45 (m, 2H), 7.62 (dd, J=7.6 Hz, 1H), 7.78 (m, 1H), 7.91 (m, 2H), 8.92 (s, 1H); MS(FAB) m/z 521.1 (MH$^+$).

EXAMPLE 26

3-{3-[5-(Isopropyl-phenyl-carbamoylmethyl)4-oxo-2,3,4,5-tetrahydro-benzo [b][1,4]thiazepin-3-yl]]-ureido}-benzoic acid.

To intermediate 22 G, (79 mg, 0.21 mmol) in DCM (3 mL) was added TEA (0.10 mL, 0.71 mmol) and m-carboethoxyphenyl isocyanate (40 mg, 0.21 mmol). The reaction mixture stirred at rt for 12 h and was concentrated to dryness to give 170 mg of a crude product. To this crude product (170 mg, 0.30 mmol) in methanol (12 mL) was added 5% aqueous potassium carbonate (3 mL). The reaction mixture was heated at reflux for 12 h, was concentrated to dryness and purified by RP-HPLC (42–60%, over 30 min) to give the titled compound (13.2 mg, 12%). $t_R$=24.6 min (42–60%, over 30 min); $^1$HNMR (300 MHz, d6-DMSO) d 0.99 (d, J=6.7 Hz, 3H), 1.01 (d, J=6.7 Hz, 3H), 2.89 (dd, J=11.2, 22.7 Hz, 1H), 3.66 (d, J=16.4 Hz, 1H), 4.30 (d, J=16.2 Hz, 1H), 4.37 (m, 1H), 4.83 (m, 1H), 6.73 (d, J=7.5 Hz, 1H), 7.31 (m, 4H), 7.53 (bm, 7H), 7.96 (m, 1H), 9.02 (s, 1H); MS (FAB) 533.0 (MH$^+$).

EXAMPLE 27

The sulfoxides of 3-{3-[5-(Isopropyl-phenyl-carbamoylmethyl)-4-oxo-2,3,4,5-tetrahydro-benzo [b][1,4]thiazepin-3-yl]]-ureido}-benzoic acid.

To example 26 (207 mg, 0.39 mmol) in methanol (5 mL) and water (1 mL) was added sodium periodate (128 mg, 0.60 mmol). The reaction mixture was stirred for 12 h, was concentrated to dryness and purified by RP-HPLC (42–60%, over 30 min) to give a one to one mixture of the titled compounds (12 mg, 6%). Isomer 1: $t_R$=14.0 min and Isomer 2: $t_R$=16.8 min (42–60%, over 30 min); $^1$HNMR (300 MHz, d6-DMSO) d 0.99 (m, 12 H), 3.05 (m, 2H), 3.56 (d, J=16.6

Hz, 2H), 3.88 (m, 2H), 4.00 (m, 1H), 4.07 (s, 1H), 4.26 (d, J=16.6 Hz, 1H), 4.35 (m, 1H), 4.85 (m, 1H), 4.85 (m, 2H), 6.75 (d, J=7.3 Hz, 1H), 6.83 (d, J=7.3 Hz, 1H), 7.32 (m, 6H), 7.46 (m, 12H), 7.75 (m, 4H), 7.96 (m, 2H), 9.00 (d, 6.8 Hz, 2H); MS(FAB) m/z 549.9 (MH$^+$).

EXAMPLE 28

N-Isopropyl-2-[4-oxo-3-(3-phenyl-ureido)-3,4-dihydro-2H-benzo[b][1,4]thiazepin-5-yl]-N-phenyl-acetamide.

Intermediate 28 A

Similarly to intermediate 22 A, to N-Acetyl-L-cysteine (33.9 g, 0.21 mol) in ethanol (150 mL) and water (500 mL) was added 1-fluoro-2-nitrobenzene (27.7 mL, 0.26 mol) and sodium bicarbonate (50 g, 0.60 mol) to give the titled product (46.53 g, 69%). $R_f$=0.14 (10% methanol/DCM); $^1$HNMR (300 MHz, d6-DMSO) d 1.81 (s, 3H), 3.25 (m, 1H), 3.49 (m, 1H), 4.43 (m, 1H), 7.41 (m, 1H), 7.69 (m, 2H), 8.16 (d, J=8.3 Hz, 1H), 8.42 (d, J=7.8 Hz, 1H); MS(FAB) m/z 285.0 (MH$^+$).

Intermediate 28 B

To intermediate 28 A (46.5 g, 180.4 mmol) in water (770 mL) was added sulfuric acid (192 mL) at a slow steady rate. The reaction mixture was heated at reflux for 3 h, cooled and was stirred at rt for 12 h. The reaction mixture was cooled to 0° C. and ammonium hydroxide was added slowly. A yellow precipitate was formed and collected by filtration, washed with water and dried to give the crude product (47.81 g, 100%). $R_f$=0.04 (10% methanol/DCM, 0.5% HOAc); MS(FAB) m/z 242.9 (MH$^+$).

Intermediate 28 C

To intermediate 28 B (47.81 g, 227.67 mmol) in 2N sodium hydroxide (114 mL) at 0° C. was added benzyl chloroformate (32.50 mL, 227.67 mmol). The reaction mixture was stirred at rt for 12 h, was diluted with Et$_2$O (150 mL) and acidified to pH1 with concentrated HCl. A black gum forms which solidifies when stirred with water. The precipitate was collected by filtration, washed with water, and dried to give the titled compound (25.85 g, 40%). $R_f$=0.33 (10% methanol/DCM); $^1$HNMR (300 MHz, d6-DMSO) d 3.20 (m, 1H), 3.54 (m, 1H), 4.17 (m, 1H), 5.00 (s, 2H), 7.36 (m, 6H), 7.71 (m, 2H), 8.16 (d, J=8.5 Hz, 1H); MS(FAB) m/z 376.9 (MH$^+$).

Intermediate 28 D

Similarly to intermediate 22 D, to intermediate 28 C (25.85 g, 68.75 mmol) in methanol (1.2 L) was added zinc (63 g) and ammonium chloride (7.27 g, 136 mmol) to give the titled compound (29.4 g, 100%). $R_f$=0.35 (10% methano/DCM); $^1$HNMR (300 MHz, d6-DMSO) d 2.91 (m, 1H), 3.05 (m, 1H), 3.85 (m, 1H), 4.98 (s, 2H), 6.45 (m, 1H), 6.67 (dd, J=1.2, 8.1 Hz, 1H), 7.00 (m, 1H), 7.21 (m, 1H), 7.34 (m, 4H); MS(FAB) m/z 346.9 (MH$^+$).

Intermediate 28 E

Similarly to intermediate 22 E, to intermediate 28 D (29.4 g, 85 mmol) in DMF (200 mL) was added EDC (16.3 g, 85 mmol) to give the titled compound (3.69 g, 13%). $R_f$=0.81 (10% methanol/DCM); $^1$HNMR (300 MHz, CDCl$_3$) d 2.94 (t, J=11.2 Hz, 1H), 3.85 (m, 1H), 4.49 (m, 1H), 5.05 (s, 2H), 5.89 (bd, J=7.1 Hz, 1H), 7.24 (m, 1H), 7.35 (m, 6H), 7.63 (d, J=7.6 Hz, 1H), 8.0 (bs, 1H); MS(FAB) m/z 329.1 (MH$^+$).

Intermediate 28 F

Similarly to intermediate 22 F, intermediate 28 E (2 g, 6.1 mmol) in DMF (61 mL) was added sodium hydride (243 mg, 6.1 mmol) and 2-bromo-N-isopropyl-N-phenyl acetamide (1.56 g, 6.1 mmol) to give the titled compound (2.81 g, 92%). $R_f$=0.33 (66% EtOAc/Hexane); $t_R$=11 min (55–65% C, over 30 min); $^1$HNMR (300 MHz, CDCl$_3$) d 1.08 (d, J=6.9 Hz, 6H), 2.79 (t, J=11.1 Hz, 1H), 3.50 (d, J=16.6 Hz, 1H), 3.78 (m, 1H), 4.46 (m, 1H), 4.55 (d, J=16.6 Hz, 1H), 5.04 (m, 3H), 5.88 (bd, J=6.8 Hz, 1H), 7.30 (m, 14H); MS(FAB) m/z 504.1 (MH$^+$).

Intermediate 28 G

Similarly to intermediate 22 G, to intermediate 28 F (1.14 g, 2.27 mmol) in methanol (5 mL) was added 10% palladium on carbon (1 g), and ammonium formate (0.717 g, 11.37 mmol) to give the titled compound (770 mg, 92%). $R_f$=0.17 (10% methanol/DCM); $^1$HNMR (300 MHz, CDCl$_3$) d 1.07 (d, J=6.8 Hz, 3H), 1.09 (d, J=6.8 Hz, 3H), 2.75 (m, 1H), 3.49 (d, J=16.6 Hz, 1H), 3.57 (m, 2H), 4.65 (d, J=16.6 Hz, 1H), 5.08 (m, 1H), 7.15 (m, 3H), 7.41 (m, 8H).

EXAMPLE 28

N-Isopropyl-2-[4-oxo-3-(3-phenyl-ureido)-3,4-dihydro-2H-benzo[b][1,4]thiazepin-5-yl]-N-phenyl-acetamide.

Similarly to 22, to intermediate 28 G (100 mg, 0.27 mmol) in DCM (3 mL) was added phenyl isocyanate (0.32 mL, 0.27 mmol) which gave the titled compound (21 mg, 16%) after purification by RP-HPLC (42–60%, over 30 min). $t_R$=14.2 (42–60%, over 30 min); $^1$HNMR (300 MHz, CDCl$_3$) d 1.03 (d, J=6.9 Hz, 3H), 1.06 (d, J=6.9 Hz, 3H), 2.95 (m, 1H), 3.62 (d, J=16.3 Hz, 1H), 3.84 (m, 1H), 4.55 (d, J=16.9, 1H), 4.68 (m, 1H), 5.02 (m, 1H), 6.28 (bs, 1H), 7.05 (m, 2H), 7.26 (m, 8H), 7.44 (m, 4H), 7.60 (d, J=8.3 Hz, 1H); MS(FAB) m/z 489.1 (MH$^+$).

EXAMPLES 29, 30

The sulfoxides of N-Isopropyl-2-[4-oxo-3-(3-phenyl-ureido)-3,4-dihydro-2H-benzo[b][1,4]thiazepin-5-yl]-N-phenyl-acetamide.

Similarly to 23 and 24, to the crude product from example 28 (132 mg, 0.27 mmol) in methanol (4 mL) and water (1 mL) was added sodium periodate (58 mg, 0.27 mmol) which gave after purification by RP-HPLC (42–60%, over 30 min) isomer 1 as a 9/1 mixture of the sulfoxides (27 mg, 20%) and isomer 2 (15 mg, 11%). Intermediate 29, Isomer 1: $t_R$=16.0 (42–60%, over 30 min); $^1$HNMR (300 MHz, d6-DMSO) d 0.99 (d, J=6.7 Hz, 3H), 1.03 (d, J=6.7 Hz, 3H), 3.38 (m, 1H), 3.54 (d, J=16.3 Hz, 1H), 3.90 (m, 1H), 4.25 (d, J=16.6 Hz, 1H), 4.55 (m, 1H), 4.80 (m, 1H), 6.79 (d, J=7.4 Hz, 1H), 6.91 (t, J=7.4 Hz, 1H), 7.25 (m, 2H), 7.31 (m, 4H), 7.52 (m, 4H), 7.70 (m, 3H), 8.88 (s, 1H); MS(FAB) m/z 504.9 (MH$^+$). Intermediate 30, Isomer 2: $t_R$=18.3 min (42–60%, over 30 min); $^1$HNMR (300 MHz, d6-DMSO) d 0.95 (d, J=7.1 Hz, 3H), 0.96 (d, J=7.1 Hz, 3H), 3.20 (m, 2H), 3.98 (m, 1H), 4.07 (s, 2H), 4.35 (m, 1H), 4.78 (m, 1H), 6.68 (d, J=7.6 Hz, 1H), 6.87 (t, J=7.6 Hz, 1H), 7.20 (m, 2H), 7.30 (m, 3H) 7.50 (m, 3H), 7.67 (m, 2H), 8.85 (s, 1H); MS(FAB) m/z 504.9 (MH$^+$).

EXAMPLE 31

The sulfone of N-Isopropyl-2-[4-oxo-3-(3-phenyl-ureido)-3,4-dihydro-2H-benzo[b][1,4]thiazepin-5-yl]-N-phenyl-acetamide.

Similarly to Example 25, to the product from example 28 (40 mg, 0.08 mmol) in DCM (3 mL) was added mCPBA (62 mg, 0.18 mmol) which gave the titled compound (34 mg, 82%) after purification by RP-HPLC (42–60%, over 30 min). $t_R$=20.7 min (42–60%, over 30 min); $^1$HNMR (300 MHz, d6-DMSO) d 1.02 (d, J=6.8 Hz, 3H), 1.08 (d, J=6.8

Hz, 3H), 3.45 (d, J=16.9 Hz, 1H), 3.54 (dd, J=11.2, 13.3 Hz, 1H), 4.16 (dd, J=7.1, 13.4 Hz, 1H), 4.63 (d, J=16.8 Hz, 1H), 4.88 (m, 1H), 5.01 (m, 1H), 6.33 (d, J=6.6 Hz, 1H), 7.02 (m, 2H), 7.24 (m, 6H), 7.46 (m, 5H), 7.73 (bs, 2H), 8.00 (s, 1H); MS(FAB) m/z 521.0 (MH$^+$).

EXAMPLE 32

3-{3-[5-(Isopropyl-phenyl-carbamoylmethyl)-4-oxo-2,3,4,5-tetrahydro-benzo [b][1,4]thiazepin-3-yl]-ureido}-benzoic acid.

Similarly to Example 26, to intermediate 28 G (200 mg, 0.54 mmol) in DCM (2 mL) as added the m-carboethoxyphenyl isocyanate (104 mg, 0.54 mmol). The crude urea was stirred in 5% aqueous potassium carbonate (1 mL) in methanol (3 mL) to give the titled compound (94 mg, 33%) after purification by RP-HPLC (42–60%, over 30 min). $t_R$=11.5 min (42–60%, over 30 min); $^1$HNMR (300 mHz, d6-DMSO) d 1.10 (m, 6H), 2.88 (t, J=11.2 Hz, 1H), 3.46 (m, 1H), 3.65 (d, J=16.3 Hz, 1H), 4.30 (d, J=16.3 Hz, 1H), 4.36 (m, 1H), 4.82 (m, 1H), 6.73 (d, J=7.0 Hz, 1H), 7.30 (m, 5H), 7.45 (m, 8H), 7.63 (m, 1H), 7.95 (s, 1H), 9.01 (s, 1H); MS (FAB) 532.1 (MH$^+$).

EXAMPLE 33

The sulfoxides of 3-{3-[5-(Isopropyl-phenyl-carbamoylmethyl)-4-oxo-2,3,4,5-tetrahydro-benzo [b][1,4]thiazepin-3-yl]-ureido}-benzoic acid.

To Intermediate 32 (380 mg, 0.72 mmol) in methanol (5 mL) and water (1 mL) was added sodium periodate (171 mg, 0.80 mmol) to give the titled compounds (11 mg, 3%) as a mixture of isomers after purification by RP-HPLC (42–60%, over 30 min). Isomer 1: $t_R$=5.5 min; Isomer 2: $t_R$=6.5 min (42–60%, over 30 min); $^1$HNMR (300 MHz, d6-DMSO) d 1.02 (m, 12H), 3.53 (d, J=16.6 Hz, 2H), 3.90 (bm, 2H), 4.07 (s, 1H), 4.25 (d, J=16.4 Hz, 1H), 4.38 (m, 1H), 4.58 (m, 1H), 4.80 (bm, 2H), 6.70 (d, J=7.0 Hz, 1H), 6.82 (d, J=7.0, 1H), 7.29 (m, 5H), 7.46 (m, 11H), 7.70 (m, 6H), 7.97 (m, 2H), 9.06 (d, J=7.1 Hz, 2H); MS(FAB) m/z 549.0 (MH$^+$).

EXAMPLE 34

2-{3-[3-(3-Fluoro-phenyl)-ureido]-2,2-dimethyl-4-oxo-3,4-dihydro-2H-benzo [b][1,4]thiazepin-5-yl}-N-isopropyl-N-(4-methoxy-phenyl)-acetamide.

Intermediate 34 A

Similarly to Intermediate 22 A, to D,L-penicillamin (5.6 g, 27.5 mmol) in ethanol (18 mL) and water (53 mL) was added 1-fluoro-2-nitrobenzene (27.7 mL, 0.26 mmol), and sodium bicarbonate (5.64 g, 67.1 mmol) to give the titled product (46.53 g, 69%). $^1$HNMR (300 MHz, d6-DMSO) d 1.19 (s, 3H), 1.35 (d, J=4.2 Hz, 3H), 1.89 (s, 3H), 4.41 (dd, J=9.0, 13.3 Hz, 1H), 7.88 (m, 1H), 8.07 (d, J=9.1 Hz, 1H), 8.28 (d, J=9.1 Hz, 1H); MS(FAB) m/z 313.2 (MH$^+$).

Intermediate 34 B

Similarly to intermediate 28 B, to 2-Acetylamino-3-(2-nitro-phenylsulfanyl)-3-methyl-butyric acid, intermediate 34 A (2.5 g, 8.4 mmol) in water (35 mL) was added sulfuric acid (8.7 mL) to give the crude product.

Intermediate 34 C

Intermediate 34 B was basified with saturated aqueous sodium bicarbonate pH=8, and benzoxycarbonyl-N-hydroxy succinimide (1.99 g, 8.0 mmol) was added to give the crude titled product (2.62 g, 92%). MS(FAB) m/z 357.0 (MH$^+$).

Intermediate 34 D

Similarly to Intermediate 22 D, to Intermediate 34 C (2.62 g, 7.4 mmol) in methanol (150 mL) was added zinc (6.7 g) and ammonium chloride (784 mg, 14.6 mmol) to give the crude amine.

Intermediate 34 E

Similarly to Intermediate 22 E, to intermediate 34 D (784 mg, 14.6 mmol) in DMF (30 mL) was added EDC (2.79 g, 14.6 mmol) to give the titled compound (1.0 g, 19%). $R_f$=0.42 (66% EtOAc/hexane).

Intermediate 34 F

To intermediate 34 E (1 g, 2.8 mmol) in DMF (6 mL) was added potassium carbonate (1.17 g, 8.5 mmol), potassium iodide (46.5 mg, 0.28 mmol), and Cl-1B (522 mg, 2.8 mmol). The reaction mixture was stirred at rt for 16 h, was diluted with EtOAc (100 mL), extracted with 1N aqueous HCl (2×20 mL), water (3×20 mL), brine (1×20 mL), dried MgSO$_4$ and concentrated to give the titled compound (2.81 g, 92%). $R_f$=0.37 (66% EtOAc/Hexane) and $R_f$=0.30 (10% methanol/DCM); MS(FAB) m/z 562.2 (MH$^+$).

Intermediate 34 G

Similarly to Intermediate 22 G, intermediate 34 F (1.37 g, 2.44 mmol) in methanol (25 mL) was added 10% palladium on carbon (1 g) and ammonium formate (1.54 g, 24.44 mmol) to give the titled compound (0.53 g, 51%). $R_f$=0.08 (10% methanol/DCM); $^1$HNMR (300 MHz, CDCl$_3$) d 1.05 (d, J=6.8 Hz, 6H), 1.26 (s, 3H), 1.39 (s, 3H), 3.20 (s, 1H), 3.40 (d, J=16.7 Hz, 1H), 3.84 (m, 3H), 4.70 (d, J=16.7 Hz, 1H), 5.03 (m, 1H), 6.97 (m, 4H), 7.15 (m, 1H), 7.26 (m, 1H), 7.42 (m, 2H), 7.55 (m, 1H); MS(FAB) m/z 428.1 (MH$^+$).

EXAMPLE 34

2-{3-[3-(3-Fluoro-phenyl)-ureido]-2,2-dimethyl 4-oxo-3,4-dihydro-2H-benzo [b][1,4]thiazepin-5-yl}-N-isopropyl-N-(4-methoxy-phenyl)-acetamide.

Similarly to Example 22, to 2-(3-amino-2,2-dimethyl-4-oxo-3,4-dihydro-2H-benzo [b][1,4]thiazepin-5-yl)-N-isopropyl-N-(4-methoxy-phenyl)-acetamide, intermediate 34 G (300 mg, 0.70 mmol) in DCM (2 mL) was added m-fluorophenyl isocyanate (0.80 mL, 0.70 mmol) to give the crude titled compound (225 mg, 57%). A sample (75 mg) was purifid by RP-HPLC (40–60%, over 30 min) to give the titled product (47 mg). $t_R$=20.9 min (40–60%, over 30 min); $^1$HNMR (300 MHz, d6-DMSO) d 0.96 (d, J=6.2 Hz, 3H), 1.21 (s, 6H), 3.59 (d, J=16.2 Hz, 1H), 3.76 (s, 3H), 4.26 (d, J=7.8, 1H), 4.55 (d, J=16.2, 1H), 4.80 (m, 1H), 6.74 (m, 1H), 7.19 (m, 3H), 7.20 (m, 2H), 7.32 (m, 1H), 7.49 (m, 1H), 7.60 (m, 2H), 9.03 (s, 1H); MS(FAB) m/z 565.1 (MH$^+$).

EXAMPLES 35, 36

The sulfoxides of 2-{3-[3-3-Fluoro-phenyl)-ureido]-2,2-dimethyl-4-oxo-3,4-dihydro-2H-benzo[b][1,4]thiazepin-5-yl}-N-isopropyl-N-(4-methoxy-phenyl)-acetamide.

Similarly to Examples 23 and 24, to example 34 (132 mg, 0.27 mmol) in methanol (4 mL) and water (1 mL) was added sodium periodate (58 mg, 0.27 mmol) which gave after purification by RP-HPLC (42–60%, over 30 min) isomer 1 as a 9/1 mixture of the sulfoxides (27 mg, 20%) and isomer 2 (15 mg, 11%). Isomer 1: $t_R$=16.0 (42–60%, over 30 min); $^1$HNMR (300 MHz, d6-DMSO) d 0.99 (d, J=6.7 Hz, 3H), 1.03 (d, J=6.7 Hz, 3H), 3.38 (m, 1H), 3.54 (d, J=16.3 Hz, 1H), 3.90 (m, 1H), 4.25 (d, J=16.6 Hz, 1H), 4.55 (m, 1H), 4.80 (m, 1H), 6.79 (d, J=7.4 Hz, 1H), 6.91 (t, J=7.4 Hz, 1H), 7.25 (m, 2H), 7.31 (m, 4H), 7.52 (m, 4H), 7.70 (m, 3H), 8.88 (s, 1H); MS(FAB) m/z 504.9 (MH$^+$). Isomer 2: $t_R$=18.3 min (42–60%, over 30 min); $^1$HNMR (300 MHz, d6-DMSO) d 0.95 (d, J=7.1 Hz, 3H), 0.96 (d, J=7.1 Hz, 3H), 3.20 (m, 2H), 3.98 (m, 1H), 4.07 (s, 2H), 4.35 (m, 1H), 4.78 (m, 1H), 6.68 (d, J=7.6 Hz, 1H), 6.87 (t, J=7.6 Hz, 1H), 7.20 (m, 2H), 7.30

(m, 3H) 7.50 (m, 3H), 7.67 (m, 2H), 8.85 (s, 1H); MS(FAB) m/z 504.9 (MH+).

EXAMPLE 37

The sulfone of 2-{3-[3-(3-Fluoro-phenyl)-ureido]-2,2-dimethyl-4-oxo-3,4-dihydro-2H-benzo[b][1,4]thiazepin-5-yl}-N-isopropyl-N-(4-methoxy-phenyl)-acetamide.

Similarly to Example 25, to example 34 (175 mg, 0.30 mmol) in DCM (5 mL) was added mCPBA (104 mg, 0.30 mmol) which gave the titled compound (76 mg, 82%) after purification by RP-HPLC (42–60%, over 30 min). $t_R$=21.8 min (42–60%, over 30 min); $^1$HNMR (300 MHz, d6-DMSO) d 0.98 (d, J=6.3 Hz, 6H), 1.11 (s, 3H), 1.24 (s, 3H), 3.64 (d, J=16.6 Hz, 1H), 3.77 (s, 3H), 4.25 (d, J=16.6 Hz, 1H), 4.34 (d, J=8.8 Hz, 1H), 4.80 (m, 1H), 6.71 (m, 1H), 6.94 (m, 2H), 7.06 (m, 1H), 7.20 (m, 3H), 7.32 (m, 1H), 7.71 (m, 2H), 7.96 (m, 2H), 9.11 (s, 1H); MS(FAB) m/z 597.2 (MH+).

EXAMPLE 38

The sulfoxides of 1H-lndole-2-carboxylic acid {5-[isopropyl-4-methoxy-phenyl)-carbamoylmethyl]-2,2-dimethyl-4-oxo-2,3,4,5-tetrahydro-benzo[b][1,4]thiazepin-3-yl}-amide.

Intermediate 38A

To intermediate 34 G (102.9 mg, 0.24 mmol) in DCM (5 mL) was added 2-indole carboxylic acid (47 mg, 0.29 mmol), HOBT (39 mg, 0.29 mmol), EDC (56 mg, 0.29 mmol) and 2d triethylamine. The reaction mixture was stirred for 16 h, diluted with EtOAc (100 mL), washed with saturated NaHCO$_3$ (2×20 mL), 1N aqueous HCl (2×20 mL), brine (1×20 mL), dried (MgSO$_4$), and concentrated to give the indole amide (110 mg, 80%). $R_f$=0.58 (10% methanol/DCM); $^1$HNMR (300 MHz, CDCl$_3$) d 1.04 (d, J=6.8 Hz, 3H), 1.06 (d, J=6.8 Hz, 3H), 1,39 (s, 6H), 3.58 (d, J=16.6 Hz, 1H), 3.83 (s, 3H), 4.59 (d, J=16.6 Hz, 1H), 4.76 (d, J=8.5 Hz, 1H), 5.03 (m, 1H), 6.89 (m, 2H), 6.98 (m, 3H), 7.13 (m, 2H), 7.45 (m, 3H), 7.61 (m, 2H), 8.98 (s, 1H); MS(FAB) m/z 571.2 (MH+).

EXAMPLE 38

The sulfoxides of 1H-Indole-2-carboxylic acid {5-[isopropyl-(4-methoxy-phenyl)-carbamoylmethyl]-2,2-dimethyl-4-oxo-2,3,4,5-tetrahydro-benzo[b][1,4]thiazepin-3-yl}-amide.

To intermediate 38A (110 mg, 0.19 mmol) in methanol DCM (4 mL) cooled to −20° C. was added 50–60% mCPBA (34 mg, 0.20 mmol). The reaction mixture was quenched after 10 min with water (4 mL) and saturated sodium sulfite (4 mL) and diluted with DCM (20 mL). The DCM layer was concentrated and purified by silica chromatography (5% methanol/DCM) to give a 3/1 mixture of sulfoxides (86.4 mg, 74%). Major isomer, $t_R$=5.8 min and minor isomer, $t_R$=6.2 min (30–50%, over 30 min); major isomer, $^1$HNMR (300 MHz, d6-DMSO) d 0.95 (d, J=6.9 Hz, 6H), 0.97 (s, 3H), 1.35 (s, 3H), 3.50 (d, J=16.5 Hz, 1H), 3.77 (s, 3H), 4.29 (d, J=16.5 Hz, 1H), 4.78 (d, J=6.9 Hz, 1H), 7.00 (m, 3H), 7.20 (m, 3H), 7.41 (m, 2H), 7.51 (m, 1H), 7.77 (m, 3H), 8.28 (m, 1H); MS(FAB) m/z 587.0

EXAMPLE 39

(2-[5,7-Dioxo-4-phenyl-6-(3-phenyl-ureido)-[1,4]diazepan-1-yl]-N-isopropyl-N-phenyl-acetamide)

Intermediate 39 A

A mixture of N-Phenylethylene diamine (0.63 g) and 2-bromo-N-isopropyl-N-phenyl acetamide (0.64 g) in THF (10 ml) was stirred at rt overnight. THF was removed under reduced pressure and the residue was purified by column chromatography on silica gel (2% MeOH: 98% CHCl$_3$) to afford the titled product (0.55 g). $^1$H NMR (300 MHz, CDCl$_3$) 1.06 (d, J=6.8 Hz, 6H), 2.76 (m, 2H), 2.95 (s, 2H), 3.11 (m, 2H), 5.00 (sept., J=6.8 Hz, 1H), 6.59 (m, 2H), 6.67 (m, 1H), 7.12 (m, 4H), 7.41 (m, 3H).

Intermediate 39 B

A solution of 2-(phenyl-hydrazano)-prpopanedioyl dichloride (1.4 g) in THF (500 ml) was added to a solution of intermediate 39 A (1.4 g) in THF (500 ml) at −20° C. The reaction mixture was stirred for 72 h at rt. THF was removed under reduced pressure and residue was purifed by column chromatography on silica gel (Hexane 33%:ethyl acetate 67%) to afford the titled product (1.0 g) as a yellow foam. $^1$H NMR (300 MHz, CDCl$_3$) 1.09 (d, J=7 Hz, 6H), 3.65 (m, 1H), 3.88 (m, 3H), 4.11 (m, 2H), 5.00 (sept., J=7 Hz, 1H), 7.02 (m, 1H), 7.24–7.50 (m, 15H).

Intermediate 39 C

Intermediate 39 B (0.95 g) was dissolved in acetic acid (30 ml) and Zn (dust) (1.1 g) was added. After stirring for 4 h, Zn was filtered off and washed with acetic acid (2×15 ml). The combined organic layers were concentrated in vacuo (0.01 mm Hg). The residue was purified by column chromatography on silica gel (4% MeOH: 95% CHCl$_3$: 1% NH$_3$(20% aq.)) to afford the titled product (0.75 g) as a yellow foam. $^1$H NMR (300 MHz, CDCl$_3$) 1.07 (2×d, J=7 Hz, 6H), 3.45 (s, 1H), 3.57 (m, 1H), 3.67 (d, J=16.4 Hz, 1H), 3.87 (d, J=16.4 Hz, 1H), 3.88 (m, 1H), 4.21 (m, 1H), 4.65 (m, 1H), 4.97 (sept., J=7 Hz, 1H), 7.22–7.48 (m, 10H).

EXAMPLE 39

(2-[5,7-Dioxo-4-phenyl-6-(3-phenyl-ureido)-[1,4]diazepan-1-yl]-N-isopropyl-N-phenyl-acetamide)

A solution of phenyl isocyanate (15 mg) in dichloromethane (1 ml) was added to a solution of intermediate 39 C (50 mg) in dichloromethane (4 ml) and the mixture was stirred at rt overnight. The solvent was removed in vacuo and the residue was purifed by column chromatography on silica gel (2% MeOH: 98% CHCl$_3$) to afford the titled product (24 mg). HPLC Column: VYDAC C-18 1 ml/min., 40–50% over 30 min., T$_r$=13.5 min. $^1$H NMR (300 MHz, CDCl$_3$) 1.00 (d, J=6.4 Hz, 6H), 3.50 (m, 3H), 3.87 (m, 3H), 4.41 (m, 1H), 4.94 (sept., J=6.4 Hz, 1H), 6.16 (s, 1H), 6.91 (m, 1H), 7.25 (m, 15H), 7.56 (m, 1H). MS (FAB) [M+H]+= 514.

EXAMPLE 40

(3-{3-[1-(Isopropyl-phenyl-carbamoylmethyl)-5,7-dioxo-4-phenyl-[1,4]diazepan-6-yl]-ureido}-benzoic acid)

Intermediate 40 A

A solution of 3-carboethoxyphenyl isocyanate (48.5 mg) in chloroform (1 ml) was added to a solution of intermediate 39 C (100 mg) in chloroform (9 ml) and the resultant mixture was stirred at rt. overnight. The solvent was removed in vacuo and the residue was purifed by column chromatography on silica gel (1.5% MeOH: 98.5% CHCl$_3$)

to afford the titled product (90 mg). $^1$H NMR (300 MHz, CDCl$_3$) 1.00 (2×d, J=6.8 Hz, 6H), 1.34(t, J=7 Hz, 3H), 3.57 (m, 2H), 3.89 (m, 3H), 4.30 (q, J=7 Hz, 2H), 4.49 (m, 1H), 4.94 (sept., J=6.8 Hz, 1H), 6.19 (d,J=6.8 Hz, 1H), 6.77 (m, 1H), 7.27 (m, 13H), 7.56 (m, 1H), 7.93 (m, 1H).

EXAMPLE 40

(3{-3-[1-Isopropyl-phenyl-carbamoylmethyl)-5,7-dioxo-4-phenyl-[1,4]diazepan-6-yl]-ureido}-benzoic acid)

Intermediate 40 A was dissolved in a mixture of 5% aq. Na$_2$CO$_3$ (2 ml), THF (2 ml) and MeOH (5 ml) and heated at reflux for 1 hr. Organic solvents were evaporated and 1N HCl aq. was added to pH=1 and the product was extracted with ethyl acetate (3×10 ml). Ethyl acetate was evaporated and the crude product was purified by RP-HPLC (C-18) (50 ml/min (40–50% over 30 min) to afford 28 mg of white lyophile. HPLC Column: Dynamax C-8 2 ml/min (20–60% over 16 min) T$_r$=10.0 min. $^1$H NMR (300 MHz, CD$_3$OD) 1.10 (2×d, J=6.8 Hz, 6H), 3.59 (d, J=16.6 Hz, 3H), 3.70 (m, 1H), 3.93 (m, 2H), 4.05 (d, J=16.6 Hz, 1H), 4.53 (m, 1H), 4.94 (sept., J=6.4 Hz, 1H), 6.13 (s, 1H), 6.91 (m, 1H), 7.25 (m, 15H), 8.06 (m, 1H). MS (FAB) [M+H]$^+$=558.

EXAMPLE 41

(1H-Pyrrole-2-carboxylic acid [1-(isopropyl-phenyl-carbamoylmethyl)-5,7-dioxo-4-phenyl-[1,4] diazepan-6-yl]-amide)

A solution of intermediate 39 C (100 mg), Pyrrole-2-carboxylic acid (28 mg) and HOBT (34 mg) in DMF (5 ml) was cooled to 0° C. and EDC (49 mg) was added in one portion. The reaction mixture was stirred overnight and poured into ice-water. Products were extracted with ethyl acetate (3×15 ml). The combined organic layers were dried with MgSO$_4$, concentrated in vacuo and the product was purifed by column chromatography on silica gel (2% MeOH:98% CHCl$_3$) providing 57 mg of the titled compound. HPLC Column: Dynamax C-8 2 ml/min (30–70% over 20 min), T$_r$=5.9min. $^1$H NMR (300 MHz, CDCl$_3$) 1.05 (m, 6H), 3.52 (m, 2H), 3.92 (m, 3H), 4.46 (m, 1H), 4.98 (sept., J=6.4 Hz, 1H), 6.20 (m, 2H), 6.80 (m, 2H), 7.32 (m, 11H), 9.69 (s, 1H). MS (FAB) [M+H]$^+$=488.

EXAMPLE 42

(1H-Indole-2-carboxylic acid [1-(isopropyl-phenyl-carbamoylmethyl)-5,7-dioxo-4-phenyl-[1,4] diazepan-6-yl]-amide)

A solution of intermediate 39 C (100 mg), lndole-2-carboxylic acid (42 mg) and HOBT (34 mg) in DMF (5 ml) was cooled to 0° C. and EDC (49 mg) was added in one portion. The reaction mixture was stirred overnight and poured into ice-water. Products were extracted with ethyl acetate (3×15 ml). The combined organic layers were dried with MgSO$_4$, evaporated in vacuo and purifed by column chromatography on silica gel (2% MeOH:98% CHCl$_3$) providing 95 mg of the titled compound. HPLC Column: Dynamax C-8 2 ml/min [30–70% over 20 min], T$_r$=9.87 min. $^1$H NMR (300 MHz, CDCl$_3$) 1.06 (2×d,J=6.4 Hz, 6H), 3.58 (m, 2H), 3.92 (m, 3H), 4.48 (m, 1H), 5.01 (sept., J=6.4 Hz, 1H), 6.25 (d, J=7 Hz, 1H), 7.25 (m, 14H), 7.62 (m, 2H), 9.41 (s, 1H). MS (FAB) [M+H]$^+$=538.

EXAMPLE 43

({2-[1 -(Isopropyl-phenyl-carbamoylmethyl)-5,7-dioxo-4-phenyl-[1,4]diazepan-6-ylcarbamoyl]-indol-1-yl}-acetic acid)

Intermediate 43 A

A solution of intermediate 39 C (100 mg), intermediate 52B (70 mg) and HOBT (34 mg) in DMF (5 ml) was cooled to 0° C. and EDC (49 mg) was added in one portion. the reaction mixture was stirred overnight and poured into ice-water. The products were extracted with ethyl acetate (3×15 ml). The combined organic layers were dried with MgSO$_4$, concentrated in vacuo and the product was purifed by column chromatography on silica gel (1% MeOH:99% CHCl$_3$) providing 95 mg of the titled compound. $^1$H NMR (300 MHz, CDCl$_3$) 1.07 (2×d, J=6.8 Hz, 6H), 1.40 (s, 9H), 2.92 (d, J=17.5 Hz, 1H), 3.62 (m, 2H), 3.98 (m, 3H), 4.48 (m, 1H), 5.00 (sept., J=6.8 Hz, 1H), 5.20 (d, J=17.6 Hz, 1H), 5.27 (d, J=17.6 Hz, 1H), 6.18 (d, J=7.1 Hz, 1H), 7.35 (m, 15H).

EXAMPLE 43

({2-[1-(Isopropyl-phenyl-carbamoylmethyl)-5,7-dioxo-4-phenyl-[1,4]diazepan-6-ylcarbamoyl]-indol-1-yl}-acetic acid)

Intermediate 43 A (95 mg) was dissolved in CHCl$_3$ (2 ml) and TFA (5 ml) was added. The reaction mixture was left overnight at rt and concentrated in vacuo. The crude product was purified by RP-HPLC [Dynamax (C-8), 10 ml/min., (50%)] to afford 65 mg of white lyophile. HPLC Column: Dynamax C-8, 2 mlmin, (30–70% over 16 min.). T$_r$=14.85 min. $^1$H NMR (300 MHz, DMSO-d$_6$) 0.98 (2×d, J=6.1 Hz, 6H), 3.62 (m, 2H), 3.98 (m, 3H), 4.50 (m, 1H), 4.82 (sept., J=6.1 Hz, 1H), 5.27 (s, 2H), 6.31 (m, 1H), 7.11 (t, J-7.4 Hz, 1H), 7.40 (m, 14H). MS (FAB) [M+H]$^+$=596

EXAMPLE 44

(2-[6-(1H-Indazol-3-ylmethyl)-5,7-dioxo-4-phenyl-[1,4]-diazepan-1-yl]-N-isopropyl-N-(4-methoxy-phenyl)-acetamide)

Intermediate 44 A

A mixture of N-Phenylethylene diamine (1.36 g) and 2-bromo-N-isopropyl-N-(4-methoxyphenyl) acetamide (1.43 g) in THF (10 ml) was stirred at rt overnight. THF was removed under reduced pressure and the residue was purifed by column chromatography on silica gel (2.5% MeOH:97.5% CHCl$_3$) to afford the titled product (1.3 g). $^1$H NMR (300 MHz, CDCl$_3$) 1.04 (d, J=6.6 Hz, 6H), 2.76 (m, 2H), 2.95 (s, 2H), 3.11 (m, 2H), 3.83 (s, 3H), 4.20 (bs, 1H), 4.97 (sept., J=6.6 Hz, 1H), 6.59 (d, J=8.3 Hz, 2H), 6.67 (m, 1H), 6.94 (m, 4H), 7.15 (m, 1H).

Intermediate 44 B

Intermediate 44 A (1.3 g) and malonyl dichloride (0.54 g) were dissolved in THF (300 ml) at 0° C. and the mixture was stirred at rt for 4 days. The solvent was removed in vacuo. The crude product was purified by column chromatography on silica gel (2% MeOH:98% CHCl$_3$) to afford the titled product (280 mg). $^1$H NMR (300 MHz, CDCl$_3$) 1.03 (d, J=6.8 Hz, 6H), 3.70 (m, 3H), 3.81 (s, 3H), 3.83 (s, 2H), 4.05 (m, 2H), 4.92 (sept., J=6.8 Hz, 1H), 6.92 (m, 2H), 7.09 (m, 2H), 7.22 (m, 3H), 7.35 (m, 2H).

Intermediate 44 D

2-Fluoroacetophenone (2 ml), anhydrous hydrazine (2 ml) and ethanol (2 ml) were placed in a sealed tube and heated in an oil bath at 150° C. for 16 h. The reaction mixture was poured into cold water (150 ml) and stirred for 1 hr. The white precipitate was collected by filtration and dried to afford the titled compound (1.5 g). ¹H NMR (300 MHz, DMSO-d₆) 2.43 (s, 3H), 7.05 (t, J=8 Hz, 1H), 7.29 (t, J=8 Hz, 1H), 7.42 (d, J=8 Hz, 1H), 7.67 (d, J=8 Hz, 1H).

Intermediate 44 E

To a solution of intermediate 44 D (260 mg), triethylamine (404 mg) and DMAP (260 mg) in acetonitrile (30 ml), di-tert-butyl carbonate (440 mg) was added and the reaction mixture was stirred overnight. Acetonitrile was removed in vacuo and the residue was dissolved in ethyl acetate. The organic solution was washed with 1N aqueous NaHSO₄, water and sat. aqueous NaHCO₃, dried with MgSO₄ and the solvent was removed in vacuo to afford the titled product (400 mg). ¹H NMR (300 MHz, CDCl₃) 1.70 (s, 9H), 2.60 (s, 3H), 7.30 (t, J=8 Hz, 1H), 7.51 (t, J=8 Hz, 1H), 7.65 (d, J=8 Hz, 1H), 8.10 (d, J=8 Hz, 1H).

Intermediate 44 F

A suspension of NBS (400 mg), intermediate 44 D (400 mg) and AIBN (40 mg) in carbon tetrachloride (50 ml) was heated at reflux for 6 h. The solvent was removed in vacuo and the residue was purified by column chromatography on silica gel (Hexane 90%: Ethyl acetate 10%) to afford the titled product (350 mg). ¹H NMR (300 MHz, CDCl₃) 1.70 (s, 9H), 4.80 (s, 2H), 7.37 (t, J=8 Hz, 1H), 7.56 (t, J=8 Hz, 1H), 7.86 (d, J=8 Hz, 1H), 8.14 (d, J=8 Hz, 1H).

Intermediate 44 C

A solution of intermediate 44 B in dry THF (5 ml) was added to a suspension of NaH (34 mg of 60% dispersion in mineral oil) in dry THF (5 ml) at 0° C. The reaction mixture was stirred for 1 hr and a solution of intermediate 44 F (212 mg) in dry THF (5 ml) was added dropwise. The reaction mixture was then stirred overnight, poured into water (150 ml) and extracted with ethyl acetate (3×30 ml). The combined organic layers were dried with MgSO₄ and the solvent removed in vacuo. The crude material was used for the next reaction without further purification or characterization.

EXAMPLE 44

(2-[6-(1H-Indazol-3-ylmethyl)-5,7-dioxo-4-phenyl-[1,4]-diazepan-1-yl]-N-isopropyl-N-(4-methoxyphenyl)-acetamide)

The crude intermediate 44 C (250 mg) was dissolved in CHCl₃ (7 ml) and TFA (4 ml) was added. The reaction mixture was stirred for 6 h and the solvents were removed in vacuo. The crude product was purified by RP-HPLC Dynamax (C-8) (10 ml/min (50%)) to afford 34 mg of white lyophile. HPLC Column: Dynamax C-8 2 ml/min (30–70% over 20 min), $T_r$=14.63 min. ¹H NMR (300 MHz, CDCl₃) 1.05 (2×d, J=6.4 Hz, 6H), 3.73 (m, 6H), 3.83 (s 3H), 4.00 (m, 1H), 4.64 (m, 1H), 4.96 (sept., J=6.4 Hz, 1H), 5.08 (m, 1H), 6.94 (m, 2H), 7.11 (m, 2H), 7.24 (m, 2H), 7.33 (m, 2H), 7.49 (m, 2H), 7.86 (d, J=8.3 Hz, 1H), 9.90 (bs, 1H). MS (FAB) [M+H]⁺=540.

EXAMPLE 45

(2-[6-(1H-Indazol-3-ylmethyl)-5,7-dioxo-4-phenyl-4,5,6,7-tetrahydro-[1,4]-diazepin-1-yl]-N-isopropyl-N-(4-methoxy-phenyl)-acetamide)

Intermediate 45A

A solution of methyl malonyl chloride (1.1 g) in chloroform (10 ml) was added to a solution of anilinoacetaldehyde diethyl acetal (2.09 g) and pyridine (0.79 g) in chloroform (20 ml) at 0° C. The reaction mixture was stirred for 2 h, evaporated and the residue purified by column chromatography on silica gel (Hexane 50%: Ethyl acetate 50%) to afford the titled product (2 g). ¹H NMR (300 MHz, CDCl₃) 1.16 (t, J=7 Hz, 6H), 3.20 (s, 2H), 3.60 (m, 4H), 3.67 (s, 3H), 3.80 (d, J=5.6 Hz, 2H), 4.82 (t, J=5.6 Hz, 1H), 7.26 (m, 2H), 7.38 (m, 3H).

Intermediate 45B

To a solution of intermediate 45A in THF (10 ml) and water (5 ml), 1N aqueous solution of NaOH (3.5 ml) was added and resultant mixture was stirred overnight. THF was removed in vacuo and 1N aqueous solution of NaHSO₄ (3.5 ml) was added. The product was extracted with ethyl acetate (2×50 ml). The organic layers were combined, dried with MgSO4 and the solvent removed in vacuo to afford 1 g of the titled product. ¹H NMR (300 MHz, CDCl₃) 1.16 (t, J=7 Hz, 6H), 3.20 (s, 2H), 3.60 (m, 4H), 3.67 (s, 3H), 3.80 (d, J=5.6 Hz, 2H), 4.82 (t, J=5.6 Hz, 1H), 7.26 (m, 2H), 7.38 (m, 3H).

Intermediate 45C 2-bromo-N-isopropyl-N-(4-methoxyphenyl) acetamide (2.86 g) was dissolved in methanol saturated with ammonia at 0° C. and left for 3 days at rt in a sealed flask.

Methanol and ammonia were removed in vacuo and the residue was dissolved in chloroform (100 ml) and washed with water (2×50 ml). The organic layer was dried with MgSO₄ and concentrated in vacuo to afford titled product (2.7 g). ¹H NMR (300 MHz, CDCl₃) 1.05 (d, J=6.6 Hz, 6H), 1.58 (s, 2H), 2.97 (s, 2H), 3.84 (s, 3H), 4.99 (sept., J=6.6 Hz, ₁H), 6.96 (m, 4H).

Intermediate 45D

A solution of intermediate 45B (0.7 g), intermediate 45C (0.53 g) and HOBT (0.31 g) in DMF (5 ml) was cooled to 0° C. and EDC (0.47 g) was added in one portion. The reaction mixture was stirred overnight and poured into ice-water. Products were extracted with ethyl acetate (3×15 ml). The combined organic layers were dried with MgSO₄, concentrated in vacuo and purifed by column chromatography on silica gel (1% MeOH:99% CHCl₃) providing 900 mg of the titled compound. ¹H NMR (300 MHz, CDCl₃) 1.03 (d, J=7 Hz, 6H), 1.13 (t, J=7 Hz, 6H), 3.03 (s, 2H), 3.54 (m, 6H), 3.78 (m, 2H), 3.81 (s, 3H), 4.80 (t, J=5.6 Hz, 1H), 4.95 (sept., J=7 Hz, 1H), 6.88 (m, 2H), 6.99 (m, 2H), 7.28 (m, 6H), 8.21 (m, 1H).

Intermediate 45E

To a solution of intermediate 45D (680 mg) in dry DMF (5 ml), 0.5M solution of potassium bis(trimethylsilyl)amide in toluene (2.74 ml) was added at 0° C. The reaction mixture was stirred for 30 min. at 0° C. and a solution of intermediate 44 F (423 mg) in dry DMF (2 ml) was added dropwise. The reaction mixture was stirred overnight at rt, poured into water and the product extracted with ethyl acetate (2×15 ml). The solvent was removed in vacuo and the residue was purified by column chromatography on silica gel (MeOH 1%:CHCl₃ 99%) to afford the titled product (700 mg). ¹H NMR (400 MHz, CDCl₃) 1.03 (m, 12H), 1.70 (s, 9H), 3.24 (m, 2H), 3.52 (m, 5H), 3.68 (m, 3H), 3.81 (s, 3H), 3.88 (m, 1H), 4.60 (t, J=5.6 Hz, 1H), 4.95 (sept., J=7 Hz, 1H), 7.12 (m, 11H), 7.46 (m, 1H), 7.64 (d, J=8 Hz, 1H), 8.05 (d, J=8 Hz, 1H).

Intermediate 45F

A solution of intermediate 45E (200 mg) and p-toluenesulfonic acid (anhydrous, 20 mg) in dry toluene (80 ml) was placed in an oil bath at 70° C. and stirred for 30 min. Toluene was removed invacuo and the residue was purified by column chromatography on silica gel (Hexane 50%:Ethyl acetate 50%) to afford the titled product (170 mg). ¹H NMR (400 MHz, CDCl₃) 1.04 (d, J=6.7 Hz, 6H), 1.65 (s, 9H) 3.58 (d—d, J=16.6 Hz, J=4.8 Hz, 1H), 3.82 (s, 3H), 3.85 (d—d, J=16.6 Hz, 8.9 Hz, 1H), 3.93 (m, 2H), 4.35 (d—d, J=8.9 Hz, J=4.8 Hz, 1H), 4.95 (sept., J=6.7 Hz, 1H), 6.00 (s, 2H), 6.93 (m, 2H), 7.11 (m, 2H), 7.31 (m, 6H), 7.47 (t, J=7.7 Hz, 1H), 7.85 (d, J=8 Hz, 1H), 8.03 (d, J=8.4 Hz, 1H).

EXAMPLE 45

(2-[6-(1H-Indazol-3-ylmethyl)-5,7-dioxo-4-phenyl4, 5,6,7-tetrahydro-[1,4]-diazepin-1-yl]-N-isopropyl-N-(4-methoxy-phenyl)-acetamide)

Intermediate 45F (170 mg) was dissolved in CHCl$_3$ (10 ml) and TFA (5 ml) was added. The reaction mixture was stirred for 6 h and the solvents were removed in vacuo. The crude product was purified by RP-HPLC Dynamax (C-8) (10 ml/min (50%)) to afford titled product (135 mg) as a white lyophile. HPLC Column: Dynamax C-8 2 ml/min., 30–70% over 20 min., T$_r$=17.1 min. $^1$H NMR (400 MHz, CDCl$_3$) 1.04 (d, J=6.3 Hz, 6H), 3.82 (s, 3H), 3.92 (m, 4H), 4.15 (m, 1H), 4.92 (sept., J=6.3 Hz, 1H), 6.00 (s, 2H), 6.93 (m, 2H), 7.11 (m, 2H), 7.31 (m, 6H), 7.59 (m, 2H), 7.93 (d, J=8.3 Hz, 1H).

EXAMPLE 46

(R)-1H-lndole-2-carboxylic acid [1-(isopropyl-phenyl-carbamoylmethyl)-2-oxo-azepan-3-yl]-amide.

Intermediate 46A

A solution of (R)-amino-hexahydro-2-azepinone (2.00 g) in anhydrous dichloromethane (25 mL) under an atmosphere of nitrogen was treated with triethylamine (2.40 mL) followed by benzyl chloroformate (2.34 mL), an exotherm resulted. After cooling the reaction mixture to ambient temperature, an additional increment of benzyl chloroformate (0.23 mL) was added followed by aqueous sodium hydroxide (10 mL, 1N). After stirring at ambient temperature for 1 hour, the reaction mixture was transferred to a separatory funnel and the phases were separated. The organic layer was washed consecutively with aqueous hydrochloric acid (1.0N) and saturated aqueous brine. After drying over anhydrous magnesium sulfate, the organic layer was filtered and evaporated in vacuo. The residue was triturated with anhydrous diethyl ether, filtered, and dried under high vacuum to provide the title compound as an off-white solid (2.200 g). MS(Cl): [M+H]$^+$=263. TLC: R$_f$=0.35 (95:5 dichloromethane:methanol).

Intermediate 46B

A solution of intermediate 46A (2.136 g) in anhydrous dimethylformamide (10 mL) under nitrogen was cooled to 0–5° C. with an ice/water bath. Sodium hydride (60% dispersion in mineral oil, 0.342 g) was added and the mixture was stirred for 0.5 h.

A solution of 2-bromo-N-isopropyl-N-phenyl acetamide (2.19 g) in anhydrous dimethylformamide (5 mL) was added and the reaction mixture was maintained at 0–5° C. for 0.5 h. After warming to ambient temperature over one hour, the reaction mixture was partitioned between ethyl acetate and water. The mixture was transferred to a separatory funnel and the layers were separated. The organic phase was washed consecutively with water and saturated aqueous brine, dried over anhydrous magnesium sulfate, filtered, and then evaporated in vacuo to provide the title compound as an oily residue (3.703 g). MS(ESI): [M+H]$^+$=438.4. TLC: R$_f$=0.47 (95:5 dichloromethane:methanol).

Intermediate 46C

A solution of intermediate 46B (3.70 g) in absolute ethanol (20 mL) was combined with palladium on charcoal (10 wt %, 0.74 g) and stirred under a balloon of hydrogen gas overnight. The reaction mixture was filtered through a pad of diatomaceous earth (Celite) and then evaporated in vacuo to low volume. The solution was filtered again through a pad of diatomaceous earth and then extracted twice with aqueous citric acid (10% w/v). The aqueous phases were combined, neutralized with sodium hydroxide to basic pH and extracted with ethyl acetate. After separating the layers, the aqueous phase was extracted with ethyl acetate. The organic phases from the base extractions were then combined, washed with saturated aqueous brine, dried over anhydrous sodium sulfate, filtered, and evaporated in vacuo to provide the title compound as an oil (1.782 g). MS(ESI): [M+H]$^+$=304.4. $^1$H NMR (300 MHz, CDCl$_3$) d=1.05 (d, J=6.8 Hz, 6H), 1.41–2.00 (m, 8H), 3.11 (m, 1H), 3.50–3.69 (m, 3H), 3.92 (d, J=16.6 Hz, 1H), 4.96 (m, 1H), 7.20 (b, 2H), 7.39–7.48 (m, 3H).

EXAMPLE 46

(R)-1H-Indole-2-carboxylic acid [1-(isopropyl-phenyl-carbamoylmethyl)-2-oxc-azepan-3-yl]-amide.

A mixture of intermediate 46C (1.782 g), 1-hydroxybenzotriazole (0.795 g), 1-(3-dimethylaminopropyl)-3-ethylcarbodiimide hydrochloride (1.127 g) and indole-2-carboxylate (0.948 g) were combined in anhydrous dichloromethane (15 mL) under a nitrogen atmosphere and allowed to stir at room temperature overnight. The reaction mixture was washed consecutively with aqueous hydrochloric acid (1N) and aqueous sodium hydroxide (1N). The organic phase was dried over anhydrous magnesium sulfate, filtered and evaporated in vacuo. The residue was triturated with diethyl ether, filtered and washed with diethyl ether. The filter cake was dried under high vacuum to provide the title compound as a white solid (1.601 g). MS(ESI): [M+H]$^+$=447.2. $^1$H NMR (300 MHz, CDCl$_3$) d=1.07 (d, J=6.8 Hz, 6H), 1.54–2.23 (m, 6H), 3.18 (m, 1H), 3.66–3.78 (m, 2H), 3.85 (d, J=16.7 Hz, 1H), 4.81 (m, 1H), 4.99 (m, 1H), 6.93 (b, 1H), 7.12 (t, J=7.1 Hz, 1H), 7.18–7.31 (m, 3H), 7.38–7.51 (m, 4H), 7.62–7.73 (m, 2H), 9.18 (b, 1H).

EXAMPLE 47

(R)-{2-[1-(Isopropyl-phenyl-carbamoylmethyl)-2-oxo-azepan-3-ylcarbamoyl]-indol-1-yl}-acetic acid.

Intermediate 47A

To a solution of example 46 (1.200 g) under nitrogen in anhydrous dimethylformamide (10 mL) at 0–5° C. was added sodium hydride (60% dispersion in mineral oil, 0.113 g). After stirring until the reaction mixture was homogeneous, tert-butyl bromoacetate (0.434 mL) was added. The reaction mixture was maintained at 0–5° C. for 1.5 h and then added to water (100 mL). The resulting slurry was cooled to 0–5° C., filtered and the filter cake was dried under high vacuum to provide the title compound as an off-white solid (1.482 g). MS(ESI): [M+H]$^+$=561.2. $^1$H NMR (300 MHz, CDCl$_3$) d=1.07 (d, J=6.8 Hz, 6H), 1.47–2.20 (m, 6H), 1.56 (s, 9H), 3.17 (m, 1H), 3.64–3.77 (m, 2H), 3.85 (d, J=16.6 Hz, 1H), 4.75 (m, 1H), 4.98 (m, 1H), 5.27 (m, 2H), 7.01 (b, 1H), 7.13 (m, 1H): 7.19–7.31 (m, 3H), 7.41–7.50 (m, 4H), 7.63 (m, 1H), 7.71 (m, 1H).

EXAMPLE 47

(R){2-[1-Isopropyl-phenyl-carbamoylmethyl)-2-oxo-azepan-3-ylcarbamoyl]-indol-1-yl}-acetic acid.

A solution of intermediate 47A (1.377 g) in dichloromethane (12.5 mL) was cooled to 0–5° C. with an ice/ water bath under nitrogen. Trifluoroacetic acid (2.5 mL) was added and the reaction mixture was stirred for 0.5 h. An additional increment of trifluoroacetic acid (2.5 mL) was added and the reaction mixture was maintained for an additional 0.5 h. The reaction mixture was concentrated in vacuo and the residue was triturated with diethyl ether. The slurry was filtered, washed with ether and dried under high vacuum to provide the title compound as a crude solid (1.239 g). A portion of the impure product (300 mg) was purified by RP-HPLC on a C-18 column (45–60% over 30 min) Fractions containing the product were combined, frozen, and lyophilized to provide the title compound as a white lyophile (0.182 g). MS(ESI): [M+H]$^+$=505.2. $^1$H NMR (300 MHz, CDCl$_3$) d=1.08 (d, J=6.7 Hz, 6H), 1.59–2.24 (m, 6H), 3.19 (m, 1H), 3.65–3.78 (m, 2H), 3.87 (d, J=16.4 Hz, 1H), 4.80 (m, 1H), 4.93–5.06 (m, 3H), 7.06 (s, 1H), 7.17–7.28 (m, 3H), 7.35–7.54 (m, 5H), 7.64 (d, J=7.7 Hz, 1H), 8.02 (d, J=5.4 Hz, 1H).

EXAMPLE 48

(R)-4-{2-[1-(Isopropyl-phenyl-carbamoylmethyl)-2-oxo-azepan-3-ylcarbamoyl]-indol-1-yl}-butyric acid.

EXAMPLE 48

A solution of Example 46 (50 mg) in anhydrous dimethylformamide (2.0 mL) under nitrogen was cooled to 0–5° C. with an ice water bath. Sodium hydride (60% dispersion in mineral oil, 4.5 mg) was added and the mixture was allowed to stir for 0.5 h. The reaction mixture was treated with 4-bromo-butyric acid ethyl ester and then allowed to warm to ambient temperature and stir under nitrogen overnight. The mixture was added to water and the resulting slurry was filtered. The crude solid was dissolved in dichloromethane, dried over anhydrous magnesium sulfate, filtered and evaporated in vacuo to provide the ethyl ester of the title compound (64 mg) as an oil which was used without further analysis. The ester was stirred in methanol (10 mL) containing aqueous potassium carbonate (5% w/v, 2.0 mL) at reflux for 2 h. The mixture was evaporated in vacuo and the residue was partitioned between ethyl acetate and aqueous sodium hydroxide (1N). The phases were separated and the organic layer was extracted with aqueous sodium hydroxide (1N). The aqueous layers were combined and neutralized with aqueous hydrochloric acid (1N). The neutralized mixture was extracted three times with ethyl acetate and the organic layers were combined, dried over anhydrous magnesium sulfate, filtered and then evaporated in vacuo. The residue was purified by RP-HPLC on a C-18 column (36–54% over 30 min. at 10 mL/min.) Fractions containing the product were combined, frozen and lyophilized to provide the title compound as a white lyophile (11 mg). MS(ESI): [M+H]$^+$=533.2. $^1$H NMR (300 MHz, CDCl$_3$) d=1.06 (d, J=6.6 Hz, 6H), 1.56–2.38 (m, 10H), 3.15 (m, 1H), 3.62 (d, J=16.9 Hz, 1H), 3.76 (m, 1H), 3.94 (d, J=16.6 Hz, 1H), 4.58 (m, 1H), 4.73 (m, 1H), 4.83 (m, 1H), 5.00 (m, 1H), 6.93 (s, 1H), 7.10–7.63 (m, 10H).

EXAMPLE 49

(S)-1H-Indole-2-carboxylic acid [1-(isopropyl-phenyl-carbamoylmethyl)-2-oxc-azepan-3-yl]-amide.

Intermediate 49A

By employing conditions similar to intermediate 46A, (S)-amino-hexahydro-2-azepinone (2.00 g) was converted to the title compound (1.30 g). MS(Cl): [M+H]$^+$=263. TLC: R$_f$=0.35 (95:5 dichloromethane:methanol).

Intermediate 49B

By employing conditions similar to intermediate 46B, intermediate 49A (1.295 g) was converted to the title compound (1.60 g). TLC: R$_f$=0.2 (3:2 hexane:ethyl acetate). MS (ESI): [M+H]$^+$=438.2

Intermediate 49C

By employing conditions similar to intermediate 46C, intermediate 49B (1.40 g) was converted to the title compound (1.00 g). MS(ESI): [M+H]$^+$=304.4. $^1$H NMR (300 MHz, CDCl$_3$) d=1.05 (d, J=6.8 Hz, 6H), 1.41–2.00 (m, 8H), 3.11 (m, 1H) 3.50–3.69 (m, 3H), 3.92 (d, J=16.6 Hz, 1H), 4.96 (m, 1H), 7.20 (b, 2H), 7.39–7.48 (m, 3H).

EXAMPLE 49

(S)-1H-Indole-2-carboxylic acid [1-(isopropyl-phenyl-carbamoylmethyl)-2-oxc-azepan-3-yl]-amide.

By employing conditions similar to example 46, intermediate 49C (0.99 g) was converted to the title compound (0.665 g). MS(ESI): [M+H]$^+$=447.2; $^1$H NMR (300 MHz, CDCl$_3$) d=1.07 (d, J=6.8 Hz, 6H), 1.54–2.23 (m, 6H), 3.18 (m, 1H), 3.66–3.78 (m, 2H), 3.85 (d, J=16.7 Hz, 1H), 4.81 (m, 1H), 4.99 (m, 1H), 6.93 (b, 1H), 7.12 (t, J=7.1 Hz, 1H), 7.18–7.31 (m, 3H), 7.38–7.51 (m, 4H), 7.62–7.73 (m, 2H), 9.18 (b, 1H).

EXAMPLE 50

(S)-{2-[1-(Isopropyl-phenyl-carbamoylmethyl)-2-oxo-azepan-3-ylcarbamoyl]-indol-1-yl}-acetic acid.

Intermediate 50A

By employing conditions similar to intermediate 47A, example 49 (0.410 g) was converted to the title compound (0.400 g). MS(ESI): [M+H]$^+$=561.2. $^1$H NMR (300 MHz, CDCl$_3$) d=1.07 (d, J=6.8 Hz, 6H), 1.47–2.20 (m, 6H), 1.56 (s, 9H), 3.17 (m, 1H), 3.64–3.77 (m, 2H), 3.85 (d, J=16.6 Hz, 1H), 4.75 (m, 1H), 4.98 (m, 1H), 5.27 (m, 2H), 7.01 (b, 1H), 7.13 (m, 1H): 7.19–7.31 (m, 3H), 7.41–7.50 (m, 4H), 7.63 (m, 1H), 7.71 (m, 1H).

EXAMPLE 50

(S)-{2-[1-(Isopropyl-phenyl-carbamoylmethyl)-2-oxo-azepan-3-ylcarbamoyl]-indol-1-yl}-acetic acid.

By employing conditions similar to example 47, intermediate 50A (0.370 g) was converted to the title compound (0.18 g). MS(ESI): [M+H]$^+$=505.2. $^1$H NMR (300 MHz, CDCl$_3$) d=1.08 (d, J=6.7 Hz, 6H), 1.59–2.24 (m, 6H), 3.19 (m, 1H), 3.65–3.78 (m, 2H), 3.87 (d, J=16.4 Hz, 1H), 4.80 (m, 1H), 4.93–5.06 (m, 3H), 7.06 (s, 1H), 7.17–7.28 (m, 3H), 7.35–7.54 (m, 5H), 7.64 (d, J=7.7 Hz, 1H), 8.02 (d, J=5.4 Hz, 1H).

EXAMPLE 51

N-Isopropyl-2-[4-methyl-2-oxo-3-(3-phenyl-ureido)-2,3-dihydro-benzo[b][1,4]diazepin-1-yl}-N-phenyl-acetamide.

Intermediate 51A

To a solution of 1,2-phenylenediamine (10.00 g) in anhydrous toluene (50 mL) at 50° C. under nitrogen was added a solution of diketene (7.49 mL) in anhydrous toluene (25 mL) dropwise over 30 min. The reaction was held an additional 10 min. and then cooled to ambient temperature providing a thick slurry. The mixture was diluted with toluene (25 mL), filtered and washed with toluene. The product was dried under high vacuum to provide the title compound as a crystalline solid (14.47 g). $^1$H NMR: (300 MHz, d6-DMSO)_=2.24 (s, 3H); 3.01 (s, 2H); 7.08–7.22 (m, 4H); 10.35 (s, 1H). MS(FAB): [M+H]$^+$=175. Alternatively this intermediate can be made according to the literature procedure. Synthetic Communications, 20, 893–900, 1990 A solution of this intermediate (2.00 g), in anhydrous dimethyformamide (10 mL) under nitrogen was cooled to 0–5° C. with an ice/water bath. Sodium hydride (60% dispersion in mineral oil, 0.483 g) was added and the mixture was stirred vigorously over 40 min. A solution of 2-bromo-N-isopropyl-N-phenyl acetamide (3.088 g) in anhydrous dimethylformamide (7 mL) was added and the reaction mixture was maintained for 0.5 h. The reaction mixture was partitioned between ethyl acetate and water and transferred to a separatory funnel. After separating the layers, the aqueous phase was extracted twice with ethyl acetate. The organic layers were combined, washed twice with water and saturated aqueous brine. After drying over anhydrous magnesium sulfate, the solution was evaporated in vacuo to a foam and the product was crystallized from a mixture of ethyl acetate and hexane (7:3). After filtration and drying under high vacuum, the title compound was obtained as an off-white crystalline solid (1.945 g). Concentration of the mother liquor and purification on silica gel with 70–90% ethyl acetate in hexane provided an additional sample of the title compound (1.075 g) as an off-white solid. MS(FAB): [M+H]$^+$=350.3. $^1$H NMR (300 MHz, CDCl$_3$) d=1.16 (d, J=6.7 Hz, 6H), 2.41 (s, 3H), 3.04 (d, J=11.3 Hz, 1H), 3.46 (d, 11.5 Hz, 1H), 3.69 (d, J=16.7 Hz, 1H), 4.38 (d, J=16.4 Hz, 1H), 5.11 (m, 1H), 7.12–7.53 (m, 9H).

Intermediate 51B

A solution of intermediate 51A (0.100 g) in anhydrous tetrahydrofuran under nitrogen was cooled to −60° C. with a dry ice/isopropanol bath. A solution of lithium diisopropylamide (1.5 M in cyclohexane, 0.210 mL) was added dropwise. After stirring the mixture 15 min., O-(Diphenylphosphinyl)hydroxylamine (73.5 mg, *J. Chem. Soc. Perkin Trans.* 1, 3284–3288, 1981) was added in one portion and the reaction mixture was stirred at −65° C. for one hour and then allowed to warm to ambient temperature. The mixture was partitioned between ethyl acetate and aqueous potassium carbonate (5% w/v) and transferred to a separatory funnel. After separating the layers, the organic phase was washed with saturated aqueous brine, dried over anhydrous sodium sulfate and evaporated in vacuo to an oil (0.11 g). The crude product was used without further purification. TLC: Rf=0.33 (95:5 methylene chloride: methanol, silica gel) MS(FAB): [M+H]$^+$=365.2

EXAMPLE 51

N-Isopropyl-2-[4-methyl-2-oxo-3-(3-phenyl-ureido)-2,3-dihydro-benzo[b][1,4]diazepin-1-yl}-N-phenyl-acetamide.

A solution of intermediate 51B (0.106 g) in dichloromethane (5 mL) under nitrogen was treated with phenyl-isocyanate (23.7 uL). After stirring for 15 min., the reaction was quenched with aqueous potassium carbonate and transferred to a separatory funnel. The layers were separated and the organic layer was dried over anhydrous sodium sulfate, filtered and evaporated in vacuo. The product was purified by silica gel chromatography using 55:45 ethyl acetate:hexane to provide the title compound as a white lyophile (0.152 g). MS(FAB): [M+H]$^+$=484.1. $^1$H NMR (300 MHz, d6-acetone) d=1.09 (d, J=6.6 Hz, 6H), 2.84 (s, 3H), 3.99 (d, J=17.3 Hz, 1H), 4.27 (d, J=16.2 Hz, 1H), 4.56 (d, J=5.7 Hz, 1H), 4.93 (m, 1H), 6.84 (d, J=5.4 Hz, 1H), 6.94 (m, 1H), 7.18–7.60 (m, 13 H), 8.55 (s, 1H).

EXAMPLE 52

{2-[1-Isopropyl-phenyl-carbamoylmethyl)-2-oxo-2,3,4,5-tetrahydro-1H-benzo[b]azepin-3-ylcarbamoyl]-indol-1yl}-acetic acid.

Intermediate 52A

A solution of indole-2-carboxylate ethyl ester. (2.50 g) in anhydrous dimethylformamide (5 mL) was cooled to 0–5° C. under a nitrogen atmosphere. Sodium hydride (60% dispersion in mineral oil, 0.529 g) was added and the mixture was vigorously stirred until homogeneous. To the cooled solution, tert-butyl bromoacetate (2.13 mL) was added and the resulting slurry was allowed to warm to ambient temperature. The reaction mixture was partitioned between water and diethyl ether. After separating the layers, the organic layer was washed consecutively with water and saturated aqueous brine, dried over anhydrous magnesium sulfate, filtered and evaporated in vacuo to an oil. The oil was dried under high vacuum providing the title compound as an off-white solid (3.967 g). MS(FAB): [M+H]$^+$=303.1. $^1$H NMR (300 MHz, CDCl$_3$) d=1.40 (t, J=7.2 Hz, 3H), 1.44 (s, 9H), 4.35 (q, 7.2 Hz, 2H), 5.22 (s, 2H), 7.16 (m, 1H), 7.26–7.39 (m, 3H), 7.69 (d, J=8.1 Hz, 1H).

Intermediate 52B

A solution of intermediate 52A (2.00 g) in methanol (200 mL) was combined with aqueous potassium carbonate (5% w/v, 50 mL) and heated under a nitrogen atmosphere at reflux for 2 h. The methanol was removed in vacuo. The aqueous solution was washed with ethyl acetate and the layers were separated. The organic layer was extracted with aqueous potassium carbonate (5% w/v) and the aqueous layers were combined and neutralized to pH 4 with aqueous hydrochloric acid (1.0 N). The resulting slurry was filtered, washed with water and dried under high vacuum to provide the title compound as a white solid (1.070 g). MS(FAB): [M+H]$^+$=275.1. $^1$H NMR (300 MHz, CDCl$_3$) d=1.46 (s, 9H), 5.20 (s, 2H), 7.15–7.43 (m, 3H), 7.52 (s, 1H), 7.72 (d, J=7.9 Hz, 1H).

EXAMPLE 52

{2-[1-Isopropyl-phenyl-carbamoylmethyl)-2-oxo-2,3,4,5-tetrahydro-1H-benzo[b]azepin-3-ylcarbamoyl]-indol-1yl}-acetic acid.

A mixture of 2-bromo-N-isopropyl-N-(4-methoxyphenyl) acetamide (0.400 g), intermediate 52B (0.384g), 1-hydroxybenzotriazole (0.188 g), and 1-(3-dimethylaminopropyl)-3-ethylcarbodiimide hydrochloride (0.216 g) were combined in dichloromethane (10 mL) under nitrogen and stirred at ambient temperature overnight. Additional 1-(3-dimethylaminopropyl)-3-ethylcarbodiimide hydrochloride (0.053 g) and 1-hydroxybenzotriazole (0.046 g) was added and the reaction mixture was stirred for an additional 21 h. The dichloromethane was removed in vacuo and replaced with dimethylformamide (10 mL). Additional 1-(3-dimethylaminopropyl)-3-ethylcarbodiimide hydrochloride (0.216 g) and 1-hydroxybenzotriazole (0.188 g) was added and the reaction mixture was stirred for 2.5 h. The dimethylformamide was removed in vacuo and the residue was partitioned between dichloromethane and aqueous citric acid (10% w/v). After separating the layers, the organic layer was washed consecutively with aqueous potassium carbonate (5% w/v) and saturated aqueous brine, dried over anhydrous magnesium sulfate, filtered and evaporated in vacuo to provide the tert-butyl ester of the title compound as a foam (0.500 g). This material was used crude without further characterization. The crude ester (0.455 g) was dissolved in dichloromethane (6 mL) and treated with trifluoroacetic acid (6.0 mL). After stirring under nitrogen for 45 min., the reaction mixture was evaporated in vacuo and triturated with diethyl ether. The resulting slurry was filtered and washed with ether to provide the impure product. The crude sample was purified by RP-HPLC on a C-18 column with a gradient elution of 42–60% acetonitrile in aqueous trifluroacetic acid (0.1% v/v) over 30 min. at 100 mL/min. Fractions containing the product were combined, frozen and lyophilized to provide the title compound as a white lyophile (0.152 g). TLC: Rf=0.33 (9:1 methylene chloride:methanol:silica gel). $^1$H NMR: (300 MHz, CDCl$_3$) d=1.08 (d, J=6.8 Hz, 3H), 1.14 (d, J=6.8 Hz, 3H), 2.14 (m, 1H), 2.69 (m, 1H), 2.86 (m, 1H), 3.56 (m, 1H), 4.11 (d, J=16.4 Hz, 1H), 4.27 (d, J=16.4 Hz, 1H), 4.69 (m, 1H), 5.01 (s, 2H), 5.04 (m, 1H), 7.05–7.72 (m, 15H).

EXAMPLE 53

3-{[1-Isopropyl-phenyl-carbamoylmethyl)-5-methyl-2-oxo-1,2,3,5-tetrahydro-benzo[e][1,4]diazepine-4-carbonyl]-amino}-benzoic acid Intermediate 53A A mixture of 21A (97 mg, 0.276 mmol) and 3-Ethoxycarbonyl phenyl isocyanate (53 mg, 0.276 mmol) in dichloromethane (4 mL) at ambient temperature was stirred 20 h. The reaction mixture was concentrated in vacuo and purified by flash chromatography on silica gel (10 g) eluted with EtOAc/Hexanes (2:3, 250 mL) to afford the title compound (128 mg, 0.235 mmol) as a colorless glass. $^1$H NMR (300 MHz, CDCl$_3$) 1.13 (d, J=6.9 Hz, 6H), 1.32 (d, J=6.9 Hz, 3H), 1.38 (t, 3H), 3.60 (d, J=16.4 Hz, 1H), 3.84 (d, J=13.5 Hz, 1H), 4.28 (d, J=13.3 Hz, 1H), 4.36 (q, 2H), 4.49 (d, J=16.4 Hz, 1H), 5.06 (sept, 1H), 5.30 (q, 1H), 6.79 (s, 1H), 7.15–7.50 (m, 10H), 7.71 (t, 2H), 7.89 (s, 1H). MS (FAB) m/z 543.1 (MH$^+$). TLC (EtOAc/Hexanes, 2:3) R$_f$=0.27.

EXAMPLE 53

3-{[1-(Isopropyl-phenyl-carbamoylmethyl)-5-methyl-2-oxo-1,2,3,5-tetrahydro-benzo[e][1,4]diazepine4-carbonyl]-amino}-benzoic acid 53A (89 mg, 0.164 mmol) was combined with 5% aqueous potassium carbonate (1.5 mL) in methanol (7.5 mL) and heated at reflux 1.5 h. The reaction mixture was concentrated in vacuo and partitioned between dichloromethane (30 mL) and water (15 mL), the pH adjusted to 1.5 with 1N HCl and the phases separated. The aqueous phase was extracted with dichloromethane (2×30 mL), the organic phases combined, dried (MgSO$_4$), filtered and concentrated in vacuo. The crude product was purified by preparative RP-HPLC on a Delta-Pak C-18 column (35–45% over 30 minutes). The appropriate fraction was frozen and lyophilized to give the title compound (32 mg, 0.062 mmol) as a white powder. $^1$H NMR (300 MHz, CDCl$_3$) 1.14 (d, J=6.8 Hz, 3H), 1.21 (d, J=6.8 Hz, 3H), 1.24 (d, J=7.1 Hz, 3H), 3.65 (d, J=16.4 Hz, 1H), 3.81 (d, J=13.4 Hz, 1H), 4.51 (d, J=16.4 Hz, 1H), 5.00 (d, J=13.4 Hz, 1H), 5.09 (sept, 1H), 5.72 (q, 1H), 7.15–7.55 (m, 10H), 7.78 (d, J=7.5 Hz, 1H), 8.33 (d, J=8.8 Hz, 1H), 8.39 (s, 1H), 8.60 (s, 1H). MS (FAB) m/z 515.1 (MH$^+$).

EXAMPLE 54

3-{[1-(Isopropyl-phenyl-carbamoylmethyl)-2-oxo-5-phenyl-1,2,3,5-tetrahydro-benzo[e][1,4]diazepine-4-carbonyl]-amino}-benzoic acid Intermediate 54A 5-Phenyl-2-oxo-1,3-dihydro-benzo[e][1,4]diazepin-1-yl)-N-isopropyl-N-phenyl acetamide (800 mg, 1.94 mmol) was combined with 10% Pd/C (100 mg) in ethanol (35 mL) and stirred under 50 psi H$_2$ at ambient temperature for 18 h. The catalyst was removed by filtration and the filtrate concentrated in vacuo to a tan foam. The crude product was purified by flash chromatography on silica gel (20 g) eluted with EtOAc/Hexanes (2:3, 250 mL)to give the title compound (644 mg, 1.56 mmol) as a cream solid. $^1$H NMR (300MHz, CDCl$_3$) 1.07 (d, J=6.9 Hz, 3H), 1.11 (d, J=6.8 Hz, 3H), 3.42 (s, 2H), 4.06 (d, J=16.3 Hz, 1H), 4.15 (d, J=16.4 Hz, 1H), 5.05 (sept, 1H), 5.68 (s, 1H), 6.67 (d, J=6.9 Hz, 1H), 7.06 (t, 1H), 7.16 (d, J=7.1 Hz, 1H), 7.24–7.49 (m, 11H). TLC (EtOAc/Hexanes, 2:3) R$_f$=0.22.

Intermediate 54B

A mixture of 54A (115 mg, 0.277 mmol) and 3-Ethoxycarbonyl phenyl isocyanate (53 mg, 0.277 mmol) in dichloromethane (4 mL) at ambient temperature was stirred 20 h. The reaction mixture was concentrated in vacuo and purified by flash chromatography on silica gel (10 g) eluted with EtOAc/Hexanes (2:3, 250 mL) to afford the title compound (165 mg, 0.276 mmol) as a colorless glass. $^1$H NMR (300 MHz, CDCl$_3$) 1.02 (d, J=6.8 Hz, 3H), 1.06 (d, J=6.7 Hz, 3H), 1.36 (t, 3H), 2.59 (d, J=16.4 Hz, 1H), 3.15 (d, J=16.4 Hz, 1H), 3.77 (d, J=12.8 Hz, 1H), 4.34 (q, 2H), 4.60 (d, J=12.7 Hz, 1H), 4.96 (sept, 1H), 6.25 (s, 1H), 6.58 (s, 1H), 6.86–7.00 (m, 6H), 7.25–7.55 (m, 8H), 7.67–7.78 (m, 3H). MS (FAB) m/z 605.0 (MH$^+$). TLC (EtOAc/Hexanes, 2:3) R$_f$=0.26.

EXAMPLE 54

3-{[1-(Isopropyl-phenyl-carbamoylmethyl)-2-oxo-5-phenyl-1,2,3,5-tetrahydro-benzole][1,4]diazepine-4-carbonyl]-amino}-benzoic acid 54B (131 mg, 0.216 mmol) was combined with 5% aqueous potassium carbonate (1.5 mL) in methanol (7.5 mL) and heated at reflux 1.5 h. The reaction mixture was concentrated in vacuo and partitioned between dichloromethane (30 mL) and water (15 mL), the pH adjusted to 1.5 with 1N HCl and the phases separated. The aqueous phase was extracted with dichloromethane (2×30 mL), the organic phases combined, dried (MgSO$_4$), filtered and concentrated in vacuo. The crude product was purified by preparative RP-HPLC on a Delta-Pak C-18 column (40–50% over 30 minutes at 100 mL/min). The appropriate fraction was frozen and lyophilized to give the title compound (109 mg, 0.189 mmol) as a white powder. $^1$H NMR (300 MHz, CDCl$_3$) 1.04 (d, J=6.8 Hz, 3H), 1.13 (d, J=6.8 Hz, 3H), 2.66 (d, J=16.4 Hz, 1H), 3.01 (d, J=16.6 Hz, 1H), 3.80 (d, J=13.0 Hz, 1H), 4.98 (sept, 1H), 5.28 (d, J=12.9 Hz, 1H), 6.76–6.93 (m, 7H), 7.20–7.57 (m, 7H), 7.64 (dd, J=1.8, 7.4 Hz, 1H), 7.83 (d, J=7.8 Hz, 1H), 8.33 (d, J=8.5 Hz, 1H), 8.46 (s, 1H), 8.81 (s, 1H). MS (FAB) m/z 577.1 (MH$^+$).

EXAMPLE 55

1H-Indole-2-carboxylic acid [1-(isopropyl-phenyl-carbamoylmethyl)-2,5-dioxo-2,3,4,5-tetrahydro-1H-benzo[b]azepin-3-yl]-amide Intermediate 55A DL-Kynurenine (980 mg, 3.20 mmol) was combined with 1N aqueous NaHCO3 (19 mL), THF (19 mL) and benzyichloroformate (546 mg, 3.20 mmol) at ambient temperature for 2 h. The reaction mixture was filtered to remove inorganics and the filtrate partitioned between EtOAc(100 mL) and $H_2O$ (50 mL). The aqueous phase was separated, the pH adjusted to 5.0 with 1N HCl and extracted with EtOAc (100 mL). The organic phase was dried ($MgSO_4$), filtered and concentrated in vacuo to give the title compound (652 mg, 1.90 mmol) as a yellow oil. $^1$H (300 MHz, DMSO-d6) 3.51 (m, 1H), 3.80 (m, 1H), 4.76 (m, 1H), 5.11 (s, 2H), 5.91 (d, J=8.5 Hz, 1H), 6.65 (m, 1H), 7.26–7.36 (m, 6H), 7.64 (m, 1H). TLC ($CH_2Cl_2/CH_3OH$, 9:1) $R_f$=0.16.

Intermediate 55B 55A (605 mg, 1.77 mmol) was combined with DMAP (237 mg, 1.95 mmol), HOBT (465 mg, 1.95 mmol), and BOP (860 mg, 1.95 mmol) in DMF (31 mL) at ambient temperature for 20 h. The reaction mixture was concentrated in vacuo, partitioned between EtOAc (70 mL) and $H_2O$ (40 mL), the pH adjusted to 2 with 1N HCl, the organic phase separated, washed with satd. aqueous $NaHCO_3$ (30 mL) and brine (30 mL), dried ($MgSO_4$), filtered and concentrated in vacuo to give the title compound (574 mg, 1.76 mmol) as a yellow solid. $^1$H NMR (300 MHz, $CDCl_3$) 3.03 (m, 1H), 3.36 (m, 1H), 4.87 (m, 1H), 5.11 (s, 2H), 5.96 (m, 1H), 6.99 (d, J=8.0 Hz, 1H), 7.26–7.36 (m, 6H), 7.56 (m, 1H), 7.88 (m, 1H), 8.03 (s, 1H). TLC (EtOAc/Hexanes, 2:3) $R_f$=0.16.

Intermediate 55C 55B (470 mg, 1.45 mmol) was dissolved in dry DMF (10 mL) and treated with NaH (60% in mineral oil) (64 mg, 1.59 mmol) at 0° C. for 0.5 h. A mixture of 2-bromo-N-isopropyl-N-phenyl acetamide (372 mg, 1.45 mmol) was added and stirred at 0° C. for 1 h, allowed to warm to ambient temperature and stirred 18 h. The reaction mixture was concentrated in vacuo, dissolved in EtOAc (60 mL), washed with $H_2O$ (30 mL) and brine (30 mL), dried ($MgSO_4$), filtered and concentrated in vacuo to give the title compound (473 mg, 0.946 mmol) as a golden oil. $^1$H NMR (300 MHz, $CDCl_3$) 1.00 (d, J=6.8 Hz, 3H), 1.05 (d, J=6.6 Hz, 3H), 2.99 (m, 1H), 3.27 (m, 1H). 3.95 (d, J=16.4 Hz, 1H), 4.04 (d, J=16.6 Hz, 1H), 4.94–5.09 (m, 4H), 5.96 (d, J=6.4 Hz, 1H), 7.16–7.57 (m, 14H). TLC (EtOAc/Hexanes, 2:3) $R_f$=0.24.

Intermediate 55D 55C (270 mg, 0.540 mmol) was combined with 10% Pd/C (60 mg) in EtOH (7 mL) and stirred under an atmosphere of hydrogen at ambient temperature for 18 h The catalyst was removed by filtration and the filtrate concentrated in vacuo. The crude product was purified by flash chromatography on silica gel (12 g) eluted with $CH_2Cl_2/CH_3OH$ (25:1, 200 mL) to give the title compound (101 mg, 0.277 mmol) as a white solid. $^1$H NMR (300 MHz, $CDCl_3$) 1.06 (d, J=7.1 Hz, 3H), 1.09 (d, J=6.8 Hz, 3H), 3.00 (m, 2H), 3.89 (d, J=16.4 Hz, 1H), 4.13 (d, J=16.3 Hz, 1H), 4.17 (m, 1H), 5.01 (sept, 1H), 7.23–7.30 (m, 4H), 7.43–7.57 (m, 5H). TLC ($CH_2Cl_2/CH_3OH$, 19:1) $R_f$=0.22.

EXAMPLE 55

1H-Indole-2-carboxylic acid [1-(isopropyl-phenyl-carbamoylmethyl)-2,5-dioxo-2,3,4,5-tetrahydro-1H-benzo[b]azepin-3-yl]-amide 55D (216 mg, 0.591 mmol), was combined with Indole-2-carboxylic acid (95 mg, 0.591 mmol), EDC (113 mg, 0.591 mmol), and HOBT (80 mg, 0.591 mmol) in DMF (10 mL) at ambient temperature for 18 h. The reaction mixture was concentrated in vacuo, dissolved in EtOAc (40 mL), washed with $H_2O$ (30 mL) and brine (30 mL), dried ($MgSO_4$), filtered and concentrated in vacuo. The crude product was purified by preparative RP-HPLC on a Delta-Pak C-18 column (42–60% over 30 minutes). The appropriate fraction was frozen and lyophilized to give the title compound (104 mg, 0.205 mmol) as a white powder. $^1$H NMR (300 MHz, Acetone-$d_6$) 0.96 (d, J=6.8 Hz, 3H), 1.03 (d, J=6.8 Hz, 3H), 3.19 (m, 2H), 3.94 (d, J=16.4 Hz, 1H), 4.37 (d, J=16.6 Hz, 1H), 4.83 (sept, 1H), 5.36 (m, 1H), 7.04–7.66 (m, 15H), 10.83 (s, 1H). MS (FAB) m/z 509 (MH$^+$). TLC (EtOAc/Hexanes, 1:1) $R_f$=0.29.

EXAMPLE 56

3-{3-[1-(Isopropyl-phenyl-carbamoylmethyl)-2,5-dioxo-2,3,4,5-tetrahydro-1H-benzo[b]azepin-3-yl]-ureido)-benzoic acid Intermediate 56A 55D (100 mg, 0.273 mmol) was combined with Cl-1A (85 mg, 0.273 mmol) and TEA (28 mg, 0.273 mmol) in $CH_3CN$ (6 mL) and heated at reflux for 3 h. The reaction mixture was cooled in an ice-bath and the heavy precipitate removed by filtration, washed with cold $CH_3CN$ (10 mL), and dried to give the title compound (128 mg, 0.219 mmol) as a white crystaline solid. $^1$H NMR (300 MHz, $CDCl_3$) 0.98 (d, J=6.9 Hz, 3H), 1.04 (d, J=6.7 Hz, 3H), 1.59 (s, 9H), 3.10–3.35 (m, 2H), 3.96 (d, J=16.6 Hz, 1H), 4.15 (d, J=16.6 Hz, 1H), 4.92 (sept, 1H), 5.21 (m, 1H), 6.18 (m, 1H), 7.11–7.65 (m, 13H), 7.80 (m, 1H). TLC ($CH_2Cl_2/CH_3OH$, 9:1) $R_f$=0.50.

EXAMPLE 56

3-{3-[1-(Isopropyl-phenyl-carbamoylmethyl)-2,5-dioxo-2,3,4,5-tetrahydro-1H-benzo[b]azepin-3-yl]-ureido)-benzoic acid 56A (48 mg, 0.081 mmol) was combined with TFA (5 mL) in $CH_2Cl_2$ (8 mL) at ambient temperature for 1 h. The reaction mixture was concentrated in vacuo and purified by preparative RP-HPLC on a Delta-Pak C-18 column (30–60% over 30 minutes at 100 mL/min.) The appropriate fraction was frozen and lyophilized to give the title compound (35 mg, 0.066 mmol) as a white powder. MS (FAB) m/z 529.0 (MH$^+$). TLC ($CH_2Cl_2/CH_3OH$, 9:1) $R_f$=0.16.

EXAMPLE 57

1H-Indole-2-carboxylic acid [1-isopropyl-phenyl-carbamoylmethyl)-2-oxo-2,3,4,5-tetrahydro-1H-benzolb]azepin-3-yl]-amide Intermediate 57A 3-Azido-1,3,4,5-tetrahydro-benzo[b]azepin-2-one (264 mg, 1.31 mmol) was dissolved in dry DMF (5 mL) and treated with NaH (60% in mineral oil) (63 mg, 1.57 mmol) at 0° C. for 0.5 h. Cl-1E (370 mg, 1.44 mmol) was added and stirred at 0° C. for 1 h, allowed to warm to ambient temperature and stirred 18 h. The reaction mixture was concentrated in vacuo, dissolved in EtOAc (60 mL), washed with satd. aqueous $NaHCO_3$ (30 mL) and brine (30 mL), dried ($MgSO_4$), filtered and concentrated in vacuo. The crude product was purified by filtration through a pad of silica gel (4.5 g) eluted with EtOAc/Hexanes (1:4, 100 mL). The filtrate was concentrated in vacuo to give the title compound (370 mg, 0.986 mmol) as an amber oil. $^1$H NMR (300 MHz, $CDCl_3$) 1.02 (d, J=6.6 Hz, 3H), 1.09 (d, J=6.8

Hz, 3H), 2.35 (m, 2H), 2.65 (m, 1H), 3.52 (m, 1H), 3.74 (m, 1H), 4.01 (d, J=16.4 Hz, 1H), 4.26 (d, J=16.6 Hz, 1H), 4.97 (sept, 1H), 7.03–7.55 (m, 9H). MS (FAB) m/z 378 (MH$^+$). TLC (EtOAc/Hexanes, 1:4) R$_f$=0.22.

Intermediate 57B 57A (372 mg, 0.987 mmol) combined with 10% Pd/C (45 mg) in EtOH (10 mL) and was stirred under an atmosphere of hydrogen at ambient temperature for 2 h. The catalyst was removed by filtration and the filtrate concentrated in vacuo. The crude product was purified by flash chromatography on silica gel (14 g) eluted with CH$_2$Cl$_2$/CH$_3$OH (13:1, 300 mL) to give the title compound (242 mg, 0.691 mmol) as a white foam. $^1$H NMR (300 MHz, CDCl$_3$) 1.05 (d, J=6.8 Hz, 3H), 1.09 (d, J=6.8 Hz, 3H), 1.87 (m, 1H), 2.39 (m, 1H), 2.54 (m, 1H), 3.25 (m, 1H), 3.41 (m, 1H), 4.03 (d, J=16.6 Hz, 1H), 4.15 (d, J=16.6 Hz, 1H), 5.00 (sept, 1H), 7.06–7.44 (m, 9H). MS (FAB) m/z 352 (MH$^+$). TLC (CH$_2$Cl$_2$/CH$_3$OH, 13:1) R$_f$=0.21.

EXAMPLE 57

1H-Indole-2-carboxylic acid [1-(isopropyl-phenyl-carbamoylmethyl)-2-oxo-2,3,4,5-tetrahydro-1H-benzo[b]azepin-3-yl]-amide 57B (52 mg, 0.147 mmol) was combined with Indole-2-carboxylic acid (24 mg, 0.147 mmol), EDC (28 mg, 0.147 mmol), and HOBT (20 mg, 0.147 mmol) in DMF (5 mL) at ambient temperature for 3 h. The reaction mixture was concentrated in vacuo, dissolved in EtOAc (40 mL), washed with H$_2$O (15 mL) and brine (15 mL), dried (MgSO$_4$), filtered and concentrated in vacuo. The crude product was purified by flash chromatography on silica gel (5 g) eluted with EtOAc/Hexanes (1:2, 200 mL) to afford the title compound (59 mg, 0.121 mmol) as a white solid. $^1$H NMR (300 MHz, CDCl$_3$) 1.03 (d, J=6.8 Hz, 3H), 1.09 (d, J=6.8 Hz, 3H), 2.10 (m, 1H), 2.63 (m, 1H), 2.82 (m, 1H), 3.66 (m, 1H), 4.01 (d, J=16.4 Hz, 1H), 4.32 (d, J=16.4 Hz, 1H), 4.72 (m, 1H), 5.00 (m, 1H), 6.92 (s, 1H), 7.04–7.63 (m, 14H), 9.60 (s, 1H). MS (FAB) m/z 495 (MH$^+$). TLC (EtOAc/Hexanes, 2:3) R$_f$=0.21.

EXAMPLE 58

N-Isopropyl-2-[2-oxo-3-(3-phenyl-ureido)-2,3,4,5-tetrahydro-benzo[b]azepin-1-yl]-N-phenyl-acetamide 57B (46 mg, 0.130 mmol) was combined with phenyl isocyanate (16 mg, 0.137 mmol) in CH$_2$Cl$_2$ (1 mL) at ambient temperature for 2 h. The reaction mixture was concentrated in vacuo, crystalized from isopropyl alcohol (5 mL), cooled in an ice bath, filtered, washed with cold isopropyl alcohol (10 mL), air and vacuum dried to give the title compound (50 mg, 0.106 mmol) as a white solid. $^1$H NMR (300 MHz, CDCl$_3$) 0.96 (d, J=6.8 Hz, 3H), 1.03 (d, J=6.6 Hz, 3H), 2.35–2.61 (m, 3H), 3.67 (m, 1H), 3.85 (d, J=16.6 Hz, 1H), 4.42 (m, 1H), 4.47 (m, 1H), 4.92 (m, 1H), 6.19 (d, J=7.5 Hz, 1H), 6.97 (m, 2H), 7.08 (m, 1H), 7.16–7.24 (m, 6H), 7.37–7.43 (m, 5H), 7.52 (s, 1H). MS (FAB) m/z 471 (MH$^+$). TLC (EtOAc/Hexanes, 2:3) R$_f$=0.17.

EXAMPLE 59

3-{3-[1-(Isopropyl-phenyl-carbamoylmethyl)-2-oxo-2,3,4,5-tetrahydro-1H-benzo[b]azepin-3-yl]-ureido}-benzoic acid.

Intermediate 59A 57B (54 mg, 0.155 mmol) was combined with m-tert-butoxycarbonyl aniline p-nitrophenyl carbamate (48 mg, 0.155 mmol) and TEA (16 mg, 0.155 mmol) in CH$_3$CN (3.5 mL) and heated at reflux for 5 h. The reaction mixture was cooled in an ice bath and the precipitate removed by filtration, washed with cold CH$_3$CN (5 mL), air and vacuum dried to give the title compound (63 mg, 0.110 mmol) as a white solid. MS (FAB) m/z 571.3 (MH$^+$). TLC (EtOAc/Hexanes, 2:3) R$_f$=0.17.

EXAMPLE 59

3-{3-[1-(Isopropyl-phenyl-carbamoylmethyl)-2-oxo-2,3,4,5-tetrahydro-1H-benzo[b]azepin-3-yl]-ureido}-benzoic acid.

59A (59 mg, 0.103 mmol) was combined with TFA (4 mL) in CH$_2$Cl$_2$ (5 mL) at ambient temperature for 2 h. The reaction mixture was concentrated in vacuo and purified by preparative RP-HPLC on a Delta-Pak C-18 column (40–60% over 30 minutes at 100 mL/min.) The appropriate fraction was frozen and lyophilized to give the title compound (29 mg, 0.056 mmol) as a white powder. $^1$H NMR (300 MHz, Acetone-d$_6$) 0.99 (d, J=6.8 Hz, 3H), 1.05 (d, J=6.6 Hz, 3H), 2.56 (m, 3H), 3.54 (m, 1H), 4.05 (d, J=16.6 Hz, 1H), 4.28 (d, J=16.6 Hz, 1H), 4.35 (m, 1H), 4.88 (sept, 1H), 5.62 (s, 1H), 6.22 (m, 1H), 7.17–7.73 (m, 11H), 8.13 (m, 1H), 8.47 (s, 1H). MS (FAB) m/z 514.9 (MH$^+$). TLC (CH$_2$Cl$_2$/CH$_3$OH, 19:1) R$_f$=0.24.

EXAMPLE 60

N-Isopropyl-2-[2-oxo-3-(3S-phenylureido)-azepan-1-yl]-n-phenylacetamide

Intermediate 60A

Phenyl isocyanate (1.14 g, 0.01 mol) was added to a solution of L-aminocaprolactam (1.28 g, 0.01 mol) in water (50 mL). The reaction mixture was stirred for 3 hours at room temperature, then diluted with 10% aqueous HCl (20 mL) and extracted with ethyl acetate (3×50 mL). The organic layer was washed with water, dried (Na$_2$SO$_4$) and evaporated in vacuo to provide 1-(2-oxoazepan-3-yl)-3S-phenyl urea (1.9 g, 0.008 mol). MS 243 (MH$^+$, FAB); $^1$H-NMR (d6-DMSO), d 8.9 (s, 1H), 7.85 (t, J=10 Hz, 1H), 7.35 (d, J=16 Hz, 2H), 7.18 (t, J=16.8 Hz, 2H), 6.83 (t, J=14.4 Hz, 1H), 6.78 (d, J=10.4 Hz, 1H), 4.25 (dd, J=5.11, 9.6 Hz, 1H), 3.25–3.0 (m, 2H), 2.0–1.8 (m, 2H), 1.79–1.5 (m, 2H), 1.4–1.0 (m, 2H).

EXAMPLE 60

N-Isopropyl-2-[2-oxo-3-(3S-phenylureido)-azepan-1-yl]-n-phenylacetamide

2-Bromo-N-isopropyl-N-phenyl acetamide (108 mg, 0.43 mmol) was added to a solution of 1-(2-oxoazepan-3-yl)-3S-phenyl urea (100 mg, 0.43 mmol) and NaH (17.2 mg, 60% dispersion) in DMF (2 mL) at 0° C. The reaction mixture was allowed to warm to room temperature, stirred for two hours, then diluted with ethyl acetate (20 mL). The organic solution was washed with 10% aqueous citric acid (20 mL×2) and water (20 mL×2), dried (Na$_2$SO$_4$), and evaporated in vacuo to provide the titled compound (68 mg, 0.16 mmol). MS=423 (MH+, FAB); $^1$H-NMR (DMSO), d 8.85 (s, 1H), 7.45 (t, J=7.1 Hz, 2H), 7.32 (m, 2H), 7.22 (m, 1H), 7.2 (m, 2H), 6.85 (m, 1H), 6.6 (m, 1H), 4.78 (m, 1H), 4.4 (dd, J=4.8, 14.4 Hz, 1H), 3.75 (d, J=17.4 Hz, 1H), 3.58 (d, obscured by HDO), 3.55 (t, J=11.4 Hz, 1H), 3.18 (m, 1H, obscured by solvent), 1.9–1.2 (m, 6H). [a]D=−24 (c=2.55, MeOH).

EXAMPLE 61

N-Isopropyl-2-[2-oxo-343R-phenylureido)-azepan-1-yl]-n-phenylacetamide

Prepared in two steps by the same procedure as described for example 60 utilizing D-aminocaprolactam. MS=423

(MH+, FAB); $^1$H-NMR (DMSO), d 8.85 (s, 1H), 7.45 (t, J=7.1 Hz, 2H), 7.32 (m, 2H), 7.22 (m, 1H), 7.2 (m, 2H), 6.85 (m, 1H), 6.6 (m, 1H), 4.78 (m, 1H), 4.4 (dd, J=4.8, 14.4 Hz, 1H), 3.75 (d, J=17.4 Hz, 1H), 3.58 (d, obscured by HDO), 3.55 (t, J=11.4 Hz, 1H), 3.18 (m, 1H, obscured by solvent), 1.9–1.2 (m, 6H). [a]D=+24.7 (c=2.55, MeOH).

EXAMPLE 62

3-{3R-[1-(Isopropylphenylcarbamoylmethy)-2-oxoazepan-3-yl]-ureido}benzoic acid

Intermediate 62A

Prepared in the same way as 60A from D-aminocaprolactam ((214 mg, 1.7 mmol) and 3-ethoxycarbonylphenyl isocyanate (325 mg, 1.7 mmol) to provide 3-[-3R-(2-oxoazepan-3-yl)ureido] benzoic acid ethyl ester (500 mg, 1.7 mmol). MS=320 (MH$^+$, FAB); $^1$H-NMR (CD$_3$OD), d 7.85 (m, 1H), 7.48–7.3 (m, 2H), 7.25–7.1 (m, 1H), 4.3 (d, 1H), 4.18 (m, 4H), 3.1 (m, 3H), 1.9–1.75 (m, 1H), 1.65 (m, 1H), 1.4–1.0 (m, 4H)

Intermediate 62B

Prepared in the same way as Example 60 from 3-[-3-(2-oxoazepan-3-yl)ureido]benzoic acid ethyl ester (200 mg, 0.63 mmol), 2-bromo-N-isopropyl-N-phenyl acetamide (160 mg, 0.63 mmol) and NaH (25.2 mg, 60% dispersion) to provide 3-{3R-[1-(Isopropylphenylcarbamoylmethy)-2-oxoazepan-3-yl]-ureido} benzoic acid ethyl ester (254 mg, 0.5 mmol) which was used in the next step without further purification.

EXAMPLE 62

3-{3R-[1-(Isopropylphenylcarbamoylmethy)-2-oxoazepan-3-yl]-ureido}benzoic acid

3-{3R-[1-(Isopropylphenylcarbamoylmethy)-2-oxoazepan-3-yl]-ureido}benzoic acid ethyl ester (254 mg, 0.5 mmol) was dissolved in methanol (10 ml) and 1N aqueous NaOH (10 mL) and the solution was stirred at room temperature overnight. The reaction mixture was diluted with 6N aqueous HCl (2 mL) and the methanol was evaporated in vacuo. The residue was dissolved in ethyl acetate (60 mL), washed with water (20 mL×2), dried (Na2SO4) and evaporated in vacuo to provide the title compound. Purification by RP-HPLC (30–40% CH$_3$CN, over 30 min) afforded 78 mg (0.2 mmol) of the titled compound as a white lyophile. MS=467 (MH$^+$, FAB); $^1$H-NMR (CD$_3$OD), d 8.03 (s, 1H), 7.65 (m, 2H), 7.5 (m, 3H), 7.38 (m, 4H), 4.6 (d, J=11 Hz, 1H), 3.88 (d, J=17.1 Hz, 1H), 3.7 (d, J=17.1 Hz, 1H), 3.68 (t, J=14.8 Hz, 1H), 3.23 (m, obscured by solvent peak), 1.98–1.5 (m, 6H), 1.03 (d, 6H).

EXAMPLE 63

4-{3R-[1-(Isopropylphenylcarbamoylmethy)-2-oxoazepan-3-yl]-ureido}benzoic acid

Prepared in three steps in the same way as described in Example 62 from D-aminocaprolactam and 4-ethoxycarbonylphenyl isocyanate to provide the titled compound after purification by RP-HPLC (30–48% CH$_3$CN, over 30 min) (64 mg, 0.14 mmol). MS=467 (MH+, FAB); $^1$H-NMR (CD$_3$OD), d 7.94 (d, J=10.3 Hz, 2H), 7.45 (m, 5H), 7.3 (d, J=9.7 Hz, 2H), 4.6 (d, J=11 Hz, 1H), 3.88 (d, J=17.1 Hz, 1H), 3.7 (d, J=17.1 Hz, 1H), 3.68 (t, J=14.8 Hz, 1H), 3.23 (m, obscured by solvent peak), 1.98–1.5 (m, 6H), 1.03 (d, 6H).

GUINEA PIG GALL BLADDER ASSAY

Tissue Preparation:

Gallbladders were removed from guinea pigs sacrificed by cervical dislocation. The isolated gallbladders were cleaned of adherent connective tissue and cut into two rings from each animal (2–4 mm in length). The rings were subsequently suspended in organ chambers containing a physiological salt solution of the following composition (mM): NaCl (118.4); KCl (4.7); MgSO$_4$×H$_2$O (1.2); CaCl$_2$× 2H$_2$O (2.5); KH$_2$PO$_3$ (1.2); NaHCO3 (25) and dextrose (11.1). The bathing solution was maintained at 37° C. and aerated with 95% O$_2$/5% CO$_2$. Tissues were connected via gold chains and stainless steel mounting wires to isometric force displacement transducers (Grass, Model FT03 D). Responses were then recorded on a polygraph (Grass, Model 7E). One tissue from each animal served as a timelsolvent control and did not receive test compound.

Assay:

Rings were gradually stretched (over a 120 min. period) to a basal resting tension of 1 gm which was maintained throughout the experiment. During the basal tension adjustment period, the rings were exposed to acetylcholine (ACH, 10$^{-6}$ M) four times to verify tissue contractility. The tissues were then exposed to a submaximal dose of sulfated CCK-8 (Sigma, 3×10$^{-9}$ M). After obtaining a stable response, the tissues were washed out 3 times rapidly and every 5 to 10 minutes for 1 hour to reestablish a stable baseline.

Compounds were dissloved in dimethylsulfoxide (DMSO) then diluted with water and assayed via a cumulative concentration-response curve to test compound (10$^{-11}$ to 3×10$^{-6}$ M) followed by a concentration-response curve to sulfated CCK-8 (10$^{-10}$ to 10$^{-6}$ M) in the presence of the highest dose of the test compound. As a final test, ACH (10 mM) was added to induce maximal contraction. A minimum of three determinations of activity were made for each test compound.

Results test with representative compounds of the invention are given below. The compounds were tested at a concentration of 1 μM and the results expressed as % sulfated CCK-8 maximal response.

| Example No. | Contraction |
| --- | --- |
| 1 | 55 |
| 3 | 48 |
| 6 | 54 |
| 35,36 | 23 |
| 55 | 65 |
| 44 | 46 |
| 29/30 | 65% * |

* response at a concentration of 30 μM

We claim:

1. A compound of formula (I)

$$R^1R^2NCOCH_2N(R^3)COR^4 \quad (I)$$

and physiologically acceptable salts thereof wherein

R$^1$ is C$_{3-6}$alkyl, C$_{3-6}$cycloalkyl, C$_{3-6}$alkenyl, phenyl, —(CH$_2$)$_p$CN or —(CH$_2$)$_p$COO(C$_{1-4}$alkyl) and R$^2$ is [C$_{3-6}$alkyl,] C$_{3-6}$cycloalkyl, C$_{3-6}$alkenyl, benzyl, phenyl, or phenyl mono- or disubstituted independently with C$_{1-3}$alkyl, cyano, hydroxy, dimethylamino, —O(C$_{1-4}$alkyl), —O(CH$_2$C$_6$H$_5$), —NH(C$_{1-4}$alkyl), —COO(C$_{1-4}$alkyl), —N(C$_{1-4}$alkyl)$_2$ pyrrolidino, morpholino, halogen, or C$_{1-3}$alkyl substituted by one or more fluorine atoms, or R$^1$ is C$_{1-2}$alkyl and R$^2$ is phenyl substituted at the 2- or 4-position with chloro, methyl, methoxy, or methoxycarbonyl;

$R^4$ is a group of formula (III)

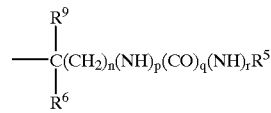
(III)

where n is 0, 1, 2 or 3;

p is the integer 0 or 1;

q is the integer 0 or 1;

r is the integer 0 or 1, provided that when q is 0 then r is 0;

$R^9$ is hydrogen or $C_{1-10}$alkyl;

$R^5$ is $C_{1-6}$alkyl, $C_{3-6}$cycloalkyl, phenyl, phenyl mono-, di or trisubstituted independently with $C_{1-4}$alkyl, hydroxy, $C_{1-6}$alkoxy, halogen, amino, mono- or di($C_{1-6}$alkyl)amino, nitro, carboxy, —COO($C_{1-4}$alkyl), carboxy$C_{1-6}$alkoxy, carboxy$C_{1-4}$alkyl, carboxymethylthio, heteroaryl, mono- or di($C_{1-6}$alkyl)aminoalkyl, or trifluoromethyl, trifluoromethoxy, $C_{1-4}$alkylthio, —$SO_v(C_{1-4}$alkyl), —$SO_vNH(C_{1-4}$alkyl), —$SO_vCF_3$ or —$SO_vC_6H_5$, —$(CH_2)_vNO_2$, —$(CH_2)_vCN$, —$(CH_2)_vCOOH$, —$(CH_2)_vCOO(C_{1-4}$alkyl), —$(CH_2)_vSCH_3$, —$(CH_2)_v$ $SOCH_3$, —$(CH_2)_vSO_3H$, $CH(C_{1-3}$alkyl) $SO_3H$, $CH(C_{1-3}$alkyl)$CO_2H$, $(CH_2)_vSO_2CH_3$, —$(CH_2)_v$ $CONH_2$, —$SCH_2COOH$, —$CONH(SO_2CH_3)$, —$CONH(SO_2CF_3)$—$(CH_2)_vN(C_{1-4}$alkyl)$_2$,—$(CH_2)_v$ $NH(SO_2CF_3)$—$CH_3)_vN(SO_2CF_3)$ ($C_{1-4}$alkyl), —$(CH_2)_vSO_2N(HCOC_{1-4}$alkyl)— $(CH_2)_v$ $SO_2N(C_{1-4}$alkyl), $CO(C_{1-4}$alkyl), —$(CH_2)_v$ $CONHSO_2(C_{1-4}$alkyl), —$(CH_2)_vCON(C_{1-4}$alkyl) $SO_2(C_{1-4}$alkyl), —$(CH_2)_vNHR^{10}$ or $(CH_2)_vOR^{11}$ substituents; heteroaryl (provided when $R_5$ is oxadiazole then $R^9$ is not hydrogen), heteroaryl substituted with halogen, $C_{1-6}$alkyl, hydroxy, nitro, cyano, carboxy, $C_{1-6}$alkoxy, benzoxy, —COO($C_{1-4}$alkyl), amino, mono- or di($C_{1-6}$alkyl)amino, phenyl or benzyl substituents; naphthyl; bicycloheteroaryl or bicycloheteroaryl N-substituted independently with hydroxy, carboxyalkyl, phenyl, heteroaryl, $C_{1-4}$alkoxy or cyano substituents, further provided when n is 1, p is 0, q is 0 and r is 0 then heteroaryl, substituted heteroaryl, bicycloheteroaryl and substituted bicycloheteroaryl are bound at the 3 position, still further provided that when n is 0, p is 1, q is 1 and r is 0 then heteraryl, substituted heteroaryl, bicycloheteroaryl and substituted bicycloheteroaryl are bound at the 2 position:

$R^{10}$ is hydrogen acetyl, $C_{1-4}$alkyl, $SO_3H$, —$SO_2CH_3$, —$SO_2CF_3$, —$SO_2C_6H_5$, $C_{1-4}$alkoxycarbonyl $R^{11}$ is hydrogen, $C_{1-6}$alkyl, $C_{3-6}$cycloalkyl, —$CH_2C_6H_5$, —$CH_2COOH$, —$CH_2$, —$CH_2CONH$ ($C_{1-4}$alkyl), —$CH_2CON(C_{1-4}$allkyl)$_2$ or

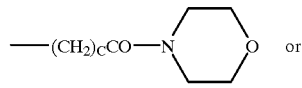
or

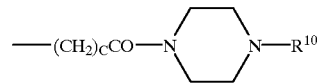

v 0, 1 or 2;

c is zero or 1

$R^3$ and $R^6$ together form a linking chain

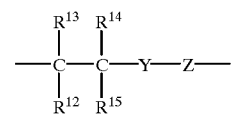

wherein the group Z is linked to the rest of the molecule at the carbon atom substituted by the group $R^9$ and wherein Z is $CH_2$, $C(CH_3)_2$, —$C(CH_3)$ or CO, Y is a group selected from S, SO, $SO_2$, CO or $CH_2$, $R^{12}$, $R^{13}$, $R^{14}$ and $R^{15}$ each represent hydrogen, or $R^{13}$ and $R^{14}$ together form a double bond and $R^{12}$ and $R^{15}$ are both hydrogen.

2. N-isopropyl-2-[2-oxo-3-(3S-phenylureido)-azepan-1-yl]-n-phenylacetamide and physiologically acceptable salts thereof.

3. A compound according to claim 1 wherein $R^1$ is isopropyl;

$R^2$ is phenyl or methoxyphenyl; and $R^9$ is H.

4. A compound according to claim 1 wherein $R^1$ is isopropyl:

$R^2$ is plienyl;

$R^1$ is H;

n is 0, p is 1, q is 1, r is 0or 1; and

Z is CH, or CO.

5. A compound according to claim 1 wherein $R^1$ is isopropyl;

$R^2$ is methoxyphenyl;

$R^9$ is H;

n is 1, p is 0, q is 0, r is 0; and

Z is CO.

6. (R)-1H-Indole-2-carboxylic acid [1-(isopropyl-phenyl-carbamoylmethyl)-2-oxo azepan-3-yl]-amide, (R)-{2-[1-(Isopropyl-phenyl-carbamoylmethyl)-2-oxo azepan-3-ylcarbamoyl]-indol-1-yl}-acetic acid, (R)-4-{2-[1-(Isopropyl phenyl-carbamoylmethyl)-2-oxo-azepan-3-ylcarbamoyl]-indol-1-yl }-butyric acid, (S)-1H-Indole-2-carboxylic acid [1-(Isopropyl-phenyl-carbamoylmethyl)-2-oxo-azepan-3-yl]-amide, (S)-{2-[1-(Isopropyl-phenyl-carbamoylmethyl)-2-oxo-azepan-3-ylcarbamoyl]-indol-1-yl}-acetic acid, N-Isopropyl-2-[2-oxo-3-(3S-phenylurcido)-azepan-1-yl]-n-phenylacctamide, N-Isopropyl-2-[2-oxo-3-(3R-phenylurcido)-azepan-1-yl]-n-phenylacetamide, 3-{(3R-[1-(Isopropylphenylcarbamoylmethy)-2-oxoazepan-3-yl]-ureido } benzoic acid; or 4-{3R [1-(Isopropylphenylcarbamoylmethy)-2-oxoazepan-3-yl]-ureido} benzoic acid or physiologically acceptable salts thereof.

7. A method for the treatment of conditions where modification of the effects of CCK and/or gastrin is of therapeutic benefit, comprising administering to the patient an therapeutically effective amount of a compound as claimed in claim 1 or a pharmaceutically acceptable salt thereof.

8. A pharmaceutical composition comprising a compound as claimed in claim 1 or a pharmaceutically acceptable salt thereof together with one or more pharmaceutically acceptable carriers.

* * * * *